(12) United States Patent
Piens et al.

(10) Patent No.: US 9,689,015 B2
(45) Date of Patent: Jun. 27, 2017

(54) DE-MANNOSYLATION OF PHOSPHORYLATED N-GLYCANS

(75) Inventors: Kathleen Camilla Telesphore Alida Maria Piens, Ghent (BE); Wouter Vervecken, Landskouter (BE)

(73) Assignee: Oxyrane UK Limited, Manchester (GB)

(*) Notice: Subject to any disclaimer, the term of this patent is extended or adjusted under 35 U.S.C. 154(b) by 0 days.

(21) Appl. No.: 13/876,730

(22) PCT Filed: Sep. 29, 2011

(86) PCT No.: PCT/IB2011/002780
§ 371 (c)(1),
(2), (4) Date: Mar. 28, 2013

(87) PCT Pub. No.: WO2012/042387
PCT Pub. Date: Apr. 5, 2012

(65) Prior Publication Data
US 2013/0295603 A1    Nov. 7, 2013

Related U.S. Application Data

(60) Provisional application No. 61/387,924, filed on Sep. 29, 2010.

(51) Int. Cl.
*C12P 21/06* (2006.01)
*C12N 15/09* (2006.01)
*C12P 21/04* (2006.01)
*C12N 9/00* (2006.01)
*C12N 1/00* (2006.01)
*C12P 21/00* (2006.01)
*C12N 15/80* (2006.01)

(52) U.S. Cl.
CPC ........... *C12P 21/005* (2013.01); *C12N 15/80* (2013.01); *C12Y 302/01113* (2013.01); *Y02P 20/52* (2015.11)

(58) Field of Classification Search
CPC ........ C12N 9/58; C12N 15/09; C12N 9/2494; C12N 15/80; C12P 21/005; Y02P 20/52; C12Y 302/01113
USPC ....... 435/68.1, 69.1, 69.4, 69.7, 183, 254.11, 435/254.2
See application file for complete search history.

(56) References Cited

U.S. PATENT DOCUMENTS

| | | |
|---|---|---|
| 4,307,717 A | 12/1981 | Hymes et al. |
| 4,352,883 A | 10/1982 | Lim |
| 4,353,888 A | 10/1982 | Sefton |
| 4,407,957 A | 10/1983 | Lim |
| 4,704,362 A | 11/1987 | Itakura et al. |
| 4,837,148 A | 6/1989 | Cregg |
| 4,879,231 A | 11/1989 | Stroman et al. |
| 4,882,279 A | 11/1989 | Cregg |
| 4,883,666 A | 11/1989 | Sabel et al. |
| 4,929,555 A | 5/1990 | Cregg et al. |
| 4,968,733 A | 11/1990 | Miller et al. |
| 4,976,859 A | 12/1990 | Wechs |
| 5,084,350 A | 1/1992 | Chang et al. |
| 5,158,881 A | 10/1992 | Aebischer et al. |
| 5,272,070 A | 12/1993 | Lehrman et al. |
| 5,284,761 A | 2/1994 | Aebischer et al. |
| 5,585,089 A | 12/1996 | Queen et al. |
| 5,798,113 A | 8/1998 | Dionne et al. |
| 5,800,828 A | 9/1998 | Dionne et al. |
| 6,110,703 A | 8/2000 | Egel et al. |
| 6,265,185 B1 | 7/2001 | Muller et al. |
| 6,699,658 B1 | 3/2004 | Wittrup et al. |
| 6,803,225 B2 | 10/2004 | Contreras et al. |
| 6,872,392 B2 | 3/2005 | Nakamura et al. |
| 7,029,872 B2 | 4/2006 | Gerngross |
| 7,259,007 B2 | 8/2007 | Bobrowicz et al. |
| 7,262,287 B2 | 8/2007 | Kang et al. |
| 7,326,681 B2 | 2/2008 | Gerngross |
| 7,390,884 B2 | 6/2008 | Segal et al. |
| 7,422,742 B2 | 9/2008 | Greenfeder et al. |
| 7,422,890 B2 | 9/2008 | Gopalakrishnakone et al. |
| 7,431,927 B2 | 10/2008 | Couto et al. |
| 7,442,772 B2 | 10/2008 | Goddard et al. |
| 7,449,308 B2 * | 11/2008 | Gerngross et al. .......... 435/69.1 |
| 7,488,591 B2 | 2/2009 | Miura et al. |
| 7,785,856 B2 | 8/2010 | LeBowitz |
| 8,026,083 B2 | 9/2011 | Callewaert |
| 8,597,906 B2 | 12/2013 | Callewaert |
| 9,206,408 B2 | 12/2015 | Callewaert |

(Continued)

FOREIGN PATENT DOCUMENTS

| | | |
|---|---|---|
| AU | 2012206984 | 8/2012 |
| EP | 1408117 | 4/2004 |

(Continued)

OTHER PUBLICATIONS

Callewaert et al., Use of HDEL-tagged Trichoderma reesei mannosyl oligosaccharide 1,2-alpha-D-mannosidase for N-glycan engineering in Pichia pastoris. FEBS Letters. 503: 173-178, 2001.*
Witkowski et al. Biochemistry 38:11643-11650, 1999.*
Seffernick et al. J. Bacteriol. 183(8):2405-2410, 2001.*
Vervecken et al., In Vivo Synthesis of Mammalian-Like, Hybrid-Type N-Glycans in Pichia pastoris. Applied and environmental microbiology. 70: 2639-2646, 2004.*
Jacobs et al. Engineering complex-type N-glycosylation in Pichia pastoris using GlycoSwitch technology. Nature Protocols. vol. 4 No. 1, 58-70, Published online Dec. 18, 2008.*
Inoue et al., Molecular cloning and nucleotide sequence of the 1,2-α-D mannosidase gene, msdS, from Aspergillus saitoi and expression of the gene in yeast cells. Biochimica et Biophysica Acta. 1253, 141-145, 1995.*
Pourcq et al., Engineering of glycosylation in yeast and other fungi: current state and perspectives. Appl Microbiol Biotechnol. 87:1617-1631. Published online: Jun. 29, 2010.*

(Continued)

*Primary Examiner* — Ganapathirama Raghu
(74) *Attorney, Agent, or Firm* — Fish & Richardson P.C.

(57) ABSTRACT

Methods for demannosylating phosphorylated N-glycans on a glycoprotein are described that use a mannosidase capable of hydrolyzing a terminal alpha-1,2 mannose linkage when the underlying mannose is phosphorylated.

13 Claims, 21 Drawing Sheets

(56) References Cited

U.S. PATENT DOCUMENTS

| | | | |
|---|---|---|---|
| 9,222,083 B2 | 12/2015 | Callewaert | |
| 9,249,399 B2 | 2/2016 | Vervecken | |
| 9,347,050 B2 | 5/2016 | Piens et al. | |
| 2002/0127219 A1 | 9/2002 | Okkels et al. | |
| 2002/0137125 A1 | 9/2002 | Zhu | |
| 2003/0147868 A1 | 8/2003 | Treco et al. | |
| 2003/0186374 A1 | 10/2003 | Hufton et al. | |
| 2004/0018588 A1 | 1/2004 | Contreras et al. | |
| 2004/0018590 A1 | 1/2004 | Gerngross et al. | |
| 2005/0014270 A1 | 1/2005 | Picataggio et al. | |
| 2005/0064539 A1 | 3/2005 | Chiba et al. | |
| 2005/0170452 A1 | 8/2005 | Wildt et al. | |
| 2005/0265988 A1 | 12/2005 | Choi et al. | |
| 2006/0014264 A1 | 1/2006 | Sauer et al. | |
| 2006/0030521 A1 | 2/2006 | Defrees et al. | |
| 2006/0040353 A1 | 2/2006 | Davidson et al. | |
| 2006/0148039 A1 | 7/2006 | Kobayashi et al. | |
| 2006/0286637 A1 | 12/2006 | Hamilton | |
| 2007/0037248 A1 | 2/2007 | Bobrowicz et al. | |
| 2008/0171359 A1 | 7/2008 | Botes et al. | |
| 2009/0069232 A1* | 3/2009 | Callewaert | C12P 21/005 514/14.6 |
| 2009/0186011 A1 | 7/2009 | Vellard et al. | |
| 2010/0291059 A1 | 11/2010 | Sakuraba et al. | |
| 2011/0201540 A1 | 8/2011 | Callewaert | |
| 2011/0207676 A1 | 8/2011 | Callewaert | |
| 2012/0135461 A1* | 5/2012 | Cook et al. | 435/68.1 |
| 2013/0053550 A1 | 2/2013 | Geysens | |
| 2013/0096281 A1 | 4/2013 | Rychaert et al. | |
| 2013/0158239 A1 | 6/2013 | Callewaert | |
| 2013/0190253 A1 | 7/2013 | Callewaert | |
| 2013/0195835 A1 | 8/2013 | Callewaert | |
| 2013/0243746 A1 | 9/2013 | Vervecken | |
| 2013/0267473 A1 | 10/2013 | Piens | |
| 2013/0295603 A1 | 11/2013 | Piens | |
| 2015/0031081 A1 | 1/2015 | Vervecken | |
| 2015/0337273 A1 | 11/2015 | Geysens et al. | |
| 2016/0251693 A1 | 9/2016 | Piens | |
| 2016/0279254 A1 | 9/2016 | Vervecken | |

FOREIGN PATENT DOCUMENTS

| | | |
|---|---|---|
| FR | 2954349 | 6/2011 |
| JP | 57-054588 | 4/1982 |
| JP | 2002-369679 | 12/2002 |
| JP | 2004-313074 | 11/2004 |
| KR | 20040062304 | 7/2004 |
| WO | WO 92/19195 | 11/1992 |
| WO | WO 95/05452 | 2/1995 |
| WO | WO 96/04378 | 2/1996 |
| WO | WO 96/21038 | 7/1996 |
| WO | WO 98/01473 | 1/1998 |
| WO | WO 98/01535 | 1/1998 |
| WO | WO 98/48025 | 10/1998 |
| WO | WO 99/36569 | 7/1999 |
| WO | WO 99/37758 | 7/1999 |
| WO | WO 01/49830 | 7/2001 |
| WO | WO 01/88143 | 11/2001 |
| WO | WO 02/18570 | 3/2002 |
| WO | WO 03/029456 | 4/2003 |
| WO | WO 03/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2005/100584 | 10/2005 |
| WO | WO 2005/106010 | 11/2005 |
| WO | WO 2008/100816 | 8/2008 |
| WO | WO 2008/120107 | 10/2008 |
| WO | WO 2009/105357 | 8/2009 |
| WO | 2009/137721 | 11/2009 |
| WO | WO 2010/099195 | 9/2010 |
| WO | WO 2011/039634 | 4/2011 |
| WO | WO 2011/061629 | 5/2011 |
| WO | WO 2012/042387 | 4/2012 |
| WO | WO2012042386 A2 | 4/2012 |
| WO | WO 2013/098651 | 7/2013 |

OTHER PUBLICATIONS

Chiba et al., Production in yeast of α-galactosidase A, a lysosomal enzyme applicable to enzyme replacement therapy for Fabry disease. Glycobiology vol. 12 No. 12 pp. 821-828, 2002.*

Devos et al., Practical limits of function prediction. Proteins: Structure, Function, and Genetics. 2000, vol. 41: 98-107.*

Whisstock et al., Prediction of protein function from protein sequence. Q. Rev. Biophysics., 2003, vol. 36 (3): 307-340.*

Hosokawa et al., EDEM1 accelerates the trimming of a1,2-linked mannose on the C branch of N-glycans. Glycobiology, 2010, vol. 20 (5): 567-575.*

"Arxula adeninivorans," Wikipedia [online] Jan. 13, 2010 [retrieved on Jan. 31, 2010]. Retrieved from the Internet: <URL: http://en.wikipedia.org/wiki/Arxula_adeninivorans>, 2 pages.

"Eukaryotes Genomes—Yarrowia Lipolytica," The European Bioinformatics Institute [online] [retrieved on Jun. 26, 2012]. Retrieved from the Internet: <URL: http://www.ebi.ac.uk/2can/genomes/eukaryotes/Yarrowia_lipolytica.html>, 1 page.

Aebi et al., "Cloning and characterization of the ALG3 gene of *Saccharomyces cerevisiae*," *Glycobiology*, vol. 6, No. 4, (1996), pp. 439-444.

Akcapinar et al., "Effect of codon optimization on the expression of Trichoderma reesei endoglucanase 1 in Pichia pastoris." *Biotechnol Prog.*, Sep.-Oct. 2011; 27(5):1257-1263. doi: 10.1002/btpr.663. Epub Jul. 2011.

Akeboshi et al., "Production of Recombinant Beta-Hexosaminidase A, a Potential Enzyme for Replacement Therapy for Tay-Sachs and Sandhoff Diseases, in the Methylotrophic Yeast Ogataea minuta", *Appl. Environ. Microbiol.*, 73( 15):4805-4812 (2007).

Alessandrini et al., "Alterations of Glucosylceramide-b-Glucosidase Levels in the Skin of Patients with Psoriasis Vulgaris," *J. Invest. Dermatol*, 23(6):1030-1036, 2004.

Bagiyan et al., "The Action of α-Mannosidase from *Oerskovia* sp. on the Mannose-Rich O-Linked Sugar Chains of Glycoproteins," *Eur. J. Biochem.*, 249(1):286-292, 1997.

Baharaeen and Vishniac, "A fixation method for visualization of yeast ultrastructure in the electron microscope ," *Mycopathologia*, 77(1):19-22, 1982.

Ballou, "Isolation, characterization, and properties of *Saccharomyces cerevisiae* mnn mutants with nonconditional protein glycosylation defects," *Methods in Enzymology*, vol. 185, (1990) pp. 440-470.

Barnay-Verdier et al., "Identification and characterization of two alpha-1,6-mannosyltransferases, Anl1p and Och1p, in the yeast yarrowia lipolytica", *Microbiology*, 150:2185-2195 (2004).

Barth and Gaillardin, "Physiology and genetics of the dimorphic fungus Yarrowia lipolytica," *FEMS Microbiology Reviews*, 19(4):219-237, Apr. 1997 [print], Jan. 2006 [online].

Bennetzen and Hall, "Codon Selection in Yeast," *J. Biol. Chem.*, 257(6):3026-3031, 1982.

Bentley et al., "Complete genome sequence of the model actinomycete Streptomyces coelicolor A3(2)," *Nature*, 417:141-147, (May 2002).

Bobrowicz et al., "Engineering of an artificial glycosylation pathway blocked in core oligosaccharide assembly in the yeast Pichia pastoris: production of complex humanized glycoproteins with terminal galactose," *Glycobiology*, 14(9):757-766 (2004).

Boisrame et al. "Sls1p, an endoplasmic reticulum component, is involved in the protein translocation process in the yeast Yarrowia lipolytica," *J. Biol. Chem.* 271(20):11668-75, 1996.

Bretthauer, "Genetic engineering of Pichia pastoris to humanize N-glycosylation of proteins," *TRENDS in Biotechnology*, 21(11):459-462 (Nov. 2003).

Burda et al., "Ordered assembly of the asymmetrically branched lipid-linked oligosaccharide in the endoplasmic reticulum is ensured by the substrate specificity of the individual glycosyltransferases", *Glycobiology*, 9(6):617-625 (1999).

(56) References Cited

OTHER PUBLICATIONS

Burton and Harding, "Hydrophobic charge induction chromatography: salt independent protein adsorption and facile elution with aqueous buffers.," *J. Chromatogr. A* 814(1-2):71-81, Jul. 1998.
Callewaert et al, "Use of HDEL-tagged Trichoderma reesei mannosyl oligosaccharide 1,2-alpha-D-mannosidase for N-glycan engineering in Pichia pastoris.," *FEBS Lett.*, 503(2-3):173-178, (Aug. 2001).
Callewaert et al., "Ultrasensitive profiling and sequencing of N-linked oligosaccharides using standard DNA-sequencing equipment," *Glycobiology* 11(4):275-281, Apr. 2001.
Carter et al., "Humanization of an anti-p185HER2 antibody for human cancer therapy," *Proc Natl Acad Sci USA*, 89(10): 4285-4289, (May 1992).
Chiba et al., "Production in yeast of alpha-galactosidase A, a lysosomal enzyme applicable to enzyme replacement therapy for Fabry disease," *Glycobiology*, 12(12):821-828 (2002).
Choe-Min-Hui: "Structural analysis of N-linked oligosaccharides assembled on recombinant proteins secreted from Yarrowia lipolytica Yloch1 and Yloch1 Ylmnn4 mutants," Thesis, Chungnam National University: Department of Microbiology, Republic of Korea, pp. 1-39, XP008160421, Retrieved from the Internet: URL: http://www.riss.kr/search/detail/DetailView.do?p_mat_type=75f99de66db18cf6&control_no=4cbf0006e9061fb5ffe0bdc3ef48d419 (2006).
Choi et al. "Use of combinatorial genetic libraries to humanize N-linked glycosylation in the yeast Pichia pastoris," *Proc. Natl. Acad. Sci. USA*, 100(9):5022-5027, Apr. 2003.
Cipollo and Trimble, "The accumulation of Man(6)GlcNAc(2)-PP-dolichol in the *Saccharomyces cerevisiae* Deltaalg9 mutant reveals a regulatory role for the Alg3p alpha1,3-Man middle-arm addition in downstream oligosaccharide-lipid and glycoprotein glycan processing," *J Biol Chem.*, 275(6):4267-4277, (Feb. 2000).
Cobucci-Ponzano et al., "The molecular characterization of a novel GH38 alpha-mannosidase from the crenarchaeon Sulfolobus solfataricus revealed its ability in de-mannosylating glycoproteins," *Biochimie.*, 92(12):1895-1907, (Aug. 2010).
Codon usage table: Yarrowia lipolytica CLIB122 [gbpln]: 5967 CDS's (2945919 codons), *Codon Usage Database* [online], [retrieved on Jul. 10, 2012]. Retrieved from the Internet:< URL: http://www.kazusa.or.jp/codon/cgi-bin/showcodon.cgi?species=284591>, 1 page.
Connock et al., "A systematic review of the clinical effectiveness and cost-effectiveness of enzyme replacement therapies for Fabry's disease and mucopolysaccharidosis type 1," *Health Technol Assess.*, 10(20):iii-iv, ix-113, 2006.
Database Accession No. P41546, UniProt (online), "RecName: Full Transcriptionmanal Activator HAC1"; XP002509286, Nojima et al., Nov. 1, 1995, 3 pages.
Database UniProt[Online] Aug. 1, 1998 (Aug. 1, 1998), "SubName: Full= Putative secreted protein;" XP002628929 retrieved from EBI accession No. UNIPROT:O69822 Database accession No. 069822, 3 pages.
Database UniProt[Online] Jul. 11, 2006 (Jul. 11, 2006), "SubName: Full= Alpha-1, 2-mannosidase, putative; Flags: Precursor;" XP002628931 retrieved from EBI accession No. UNIPROT:Q1ASW5 Database accession No. Q1ASW5, 2 pages.
Database UniProt[Online] Apr. 29, 2008 (Apr. 29, 2008), "SubName: Full= Putative uncharacterized protein;" XP002628930 retrieved from EBI accession No. UNIPROT:B1BZG6 Database accession No. B1BZG6, 2 pages.
Davies et al, "Nomenclature for sugar-binding subsites in glycosyl hydrolases," *Biochem. J.*, 321:557-559 (1997).
Fickers et al. "New disruption cassettes for rapid gene disruption and marker rescue in the yeast Yorrowia lipolytica," *J. Microbiol. Methods*. 55(3):727-737, Dec. 2003.
Fickers et al., "Carbon and nitrogen sources modulate lipase production in the yeast Yarrowia lipolytica," *J. of Applied Microbiology*, vol. 96, No. 4 (2004), pp. 742-749.
Fickers, P. et al. "Hydrophobic substrate utilization by the yeast Yarrowia lipolytica and its potential applications," *FEMS Yeast Research*, Apr. 2005, vol. 5, No. 6-7, pp. 527-543.
Freire et al. "Efficient monitoring of enzymatic conjugation reaction by surface-enhanced laser desorption/ionization time of flight mass spectrometry for process optimization," *Bioconjug. Chem.* 17(2):559-564, 2006.
Fujita and Takegawa, "Chemoenzymatic Synthesis of Neoglycoproteins Using Transglycosylation with Endo-Beta-N-acetylglucosaminidase A," *Biochem. Biophys. Res. Commun.*, 282(3):678-682, (Apr. 2001).
Gao et al. "UpGene: Application of a web-based DNA codon optimization algorithm," *Biotechnol. Prog.*, 20(2): 443-448, 2004.
Gellissen, et al., "New yeast expression platforms based on methylotrophic Hansenula polymorpha and Pichia pastoris and on dimorphic Arxula adeninivorans and Yarrowia lipolytica—A comparison," *FEMS Yeast Res.*, 5(11): 1079-1096, 2005.
Genbank Acccession No. XM502922 GI:50550898, "Yarrowia lipolytica YALI0D17028p (YALI0D17028g) mRNA, complete cds," Oct. 29, 2008, 2 pages.
Genbank Acccession No. XM503217 GI:50551486, "Yarrowia lipolytica YALI0D24101p (YALI0D24101g) mRNA, complete cds," Oct. 29, 2008, 2 pages.
Genbank Accession No. AAF34579 GI:6979644, "1,2-a-D-mannosidase [Trichoderma reesei]" Feb. 16, 2000, 1 page.
Genbank Accession No. AAO78636.1 GI:29340846, putative alpha-1,2-mannosidase [Bacteroides thetaiotaomicron VPI-5482] Feb. 8, 2011, 2 pages.
Genbank Accession No. AAO79070.1 GI:29341282, "putative alpha-1,2-mannosidase [Bacteroides thetaiotaomicron VPI-5482]," Feb. 8, 2011, 2 pages.
Genbank Accession No. AAO79099.1, "putative alpha-1,2-mannosidase [Bacteroides thetaiotaomicron VPI-5482]," Feb. 8, 2011, 2 pages.
Genbank Accession No. AF212153 GI:6979643, "Hypocrea jecorina 1,2-a-D-mannosidase (MDS1) mRNA, complete cds," Feb. 16, 2000, 2 pages.
GenBank Accession No. AF441127 GI:16974782, "Yarrowia lipolytica Mnn9p (mnn9) gene, complete cds," Apr. 11, 2003, 2 pages.
GenBank Accession No. AJ563920 GI:38488499, "Yarrowia lipolytica och1 gene for alpha 1,6 mannosyltransferase," Nov. 20, 2003, 2 pages.
GenBank Accession No. AJ865333 GI:56266607, "Trypanosoma brucei brucei glcasella gene for glucosidase II alpha subunit precursor," Oct. 25, 2005, 2 pages.
GenBank Accession No. BAA08634 GI:1171477, "alpha-mannosidase [Aspergillus saitoi]" Feb. 10, 1999, 1 page.
GenBank Accession No. NP-630514 GI:21224735, "hypothetical protein SCO6428 [Streptomyces coelicolor A3(2)]," Jan. 19, 2012, 3 pages.
GenBank Accession No. Np812442 GI:29348939, "alpha-1,2-mannosidase [Bacteroides thetaiotaomicron VPI-5482]" Jan. 20, 2012, 2 pages.
Genbank Accession No. XM499811 GI:50543289, "Yarrowia lipolytica YALI0A06589p (YALI0A06589g) mRNA, complete cds," Oct. 29, 2008, 2 pages.
GenBank Accession No. XM500574 GI:50546093, "Yarrowia lipolytica YALI0B06600p (YALI0B06600g) mRNA, complete cds," Oct. 29, 2008, 2 pages.
Genbank Accession No. XM500811 GI:50546682, "Yarrowia lipolytica YALI0B12716p (YALI0B12716g) mRNA, complete cds," Oct. 29, 2008, 2 pages.
GenBank Accession No. XM503488 GI:50552026, "Yarrowia lipolytica YALI0E03190p (YALI0E03190g) mRNA, complete cds," Oct. 29, 2008, 2 pages.
GenBank Accession No. YP003013376 YP003013376, "alpha-1,2-mannosidase [*Paenibacillus* sp. JDR-2]" Jun. 15, 2012, 3 pages.
GenBank Accession No. YP003120664 GI:256420011, "alpha-1,2-mannosidase [Chitinophaga pinensis DSM 2588]," Jun. 18, 2012, 2 pages.

(56) References Cited

OTHER PUBLICATIONS

GenBank Accession No. YP003584502 GI:295133826, "alpha-1,2-mannosidase [Zunongwangia profunda SM-A87]," Nov. 21, 2011, 2 pages.
GenBank Accession No. Z49631 GI:1015863, "S.cerevisiae chromosome X reading frame ORF YJR131w," Aug. 11, 1997, 2 pages.
GenBank Accession No. ZP01061975 GI:86143590, "putative alpha-1,2-mannosidas [Leeuwenhoekiella blandensis MED217]," Nov. 9, 2010, 1 page.
GenBank Accession No. ZP01885202 GI:149279069, "putative alpha-1,2-mannosidase [*Pedobacter* sp. BAL39]," Nov. 9, 2010, 1 page.
GenBank Accession No. ZP02866543 GI:169349605, "hypothetical protein CLOSPI00343 [Clostridium spiroforme DSM 1552]," Nov. 9, 2010, 2 pages.
GenBank Accession No. ZP03677957 GI: 224537418, "hypothetical protein BACCELL02296 [Bacteroides cellulosilyticus DSM 14838]," Nov. 10, 2010, 1 page.
GenBank Accession No. ZP04848482 GI:253571075, "conserved hypothetical protein [*Bacteroides* sp. 116]" Jun. 9, 2010, 2 pages.
GenBank Accession No. ZP05522540 GI:256784109, "secreted protein [Streptomyces lividans TK24]," Dec. 9, 2010, 2 pages.
GenBank Accession No. ZP06527366 GI:289767988, "secreted protein [Streptomyces lividans TK24]" Oct. 26, 2010, 3 pages.
GenBank Accession No. ZP07083984 GI:300774115, "probable alpha-1,2-mannosidase [Sphingobacterium spiritivorum ATCC 33861]," Dec. 1, 2010, 1 page.
Gentzsch and Tanner, "The PMT gene family: protein O-glycosylation in *Saccharomyces cerevisiae* is vital," *Embo J*, 15(21):5752-5759, (1996).
Gerngross, "Advances in the production of human therapeutic proteins in yeasts and filamentous fungi," *Nature Biotech.*, 22(11):1409-1414, (2004).
Ghaemmaghami et al., "Global analysis of protein expression in yeast." *Nature*. vol. 425, No. 6959 (Oct. 2003) pp. 737-741.
Gonzalez and Jordan, "The alpha-mannosidases: Phylogeny and adaptive diversification," *Mol Biol Evol.*, 17(2):292-300, (Feb. 2000).
Gossen and Bujard, "Studying gene function in eukaryotes by conditional gene inactivation," *Ann. Rev. Genetics* 36:153-173, (2002).
Grinna and Robbins, "Substrate specificities of rat liver microsomal glucosidases which process glycoproteins," *J. Biol. Chem.*, 255(6):2255-2258, (1980).
Guarente et al., "A GAL10-CYC1 hybrid yeast promoter identifies the GAL4 regulatory region as an upstream site," *Proc. Natl. Acad. Sci. USA* 79(23):7410-7414, (1982).
Hamilton and Gerngross, "Glycosylation engineering in yeast: the advent of fully humanized yeast," *Curr Opin Biotechnol.*, 18(5):387-392, (Oct. 2007).
Hamilton et al, "Production of complex human glycoproteins in yeast.," *Science*, 301(5637):1244-1246, Aug. 2003.
Henderson and Finn, "Human tumor antigens are ready to fly," *Advances in Immunology*, 62:217-256 (1996).
Hermans et al., "Human lysosomal alpha-glucosidase: functional characterization of the glycosylation sites," *Biochem J.*, 289 ( Pt 3):681-686, (Feb. 1993).
Hinnen et al. "Transformation of yeast," *Proc. Nat. Acad. Sci. USA* 75(4):1929-1933, (1978).
Howard et al., "Identification of the Active Site Nucleophile in Jack Bean alpha-Mannosidase Using 5-Fluoro-beta-L-Gulosyl Fluoride," *J. Biol. Chem.*, 273(4):2067-2072, 1998.
Hudson and Kortt, "High avidity scFv multimers; diabodies and triabodies," *J. Immunol. Methods*, 231(1-2):177-189, (1999).
Huston et al. "Engineered antibodies take center stage," *Hum. Antibodies*, 10(3-4):127-142, (2001).
Ichishima et al., "Molecular and enzymic properties of recombinant 1,2-alpha-mannosidase from Aspergillus saitoi overexpressed in Aspergillus oryzae cells," *Biochem. J.*, 339: 589-597, (1999).

Ito et al., "Transformation of intact yeast cells treated with alkali cations," *J. Bacteriol.*, 153(1):163-168, (1983).
Kornfeld and Kornfeld, "Assembly of asparagine-linked oligosaccharides," *Annu Rev Biochem.*, 54:631-664, (1985).
Kotula and Curtis, "Evaluation of foreign gene codon optimization in yeast: expression of a mouse IG kappa chain," *Biotechnology (N Y).*, 9(12):1386-1389, (1991).
Kuroda et al., "Production of Man5GlcNAc2-type sugar chain by the methylotrophic yeast Ogataea minuta," *FEMS Yeast Res.*, 6:1052-1062 (2006).
Laroy et al., "Glycome mapping on DNA sequencing equipment," *Nature Protocols*, 1: 397-405 (2006).
Lee and Park, "Enzymatic in vitro glycosylation using peptide-N-glycosidase F," *Enzyme and Microbial Technology*, 30(6):716-720, (2002).
Liao et al., "Cloning, expression, purification, and characterization of the human broad specificity lysosomal acid alpha-mannosidase," *J. Biol Chem.*, 271(45)28348-28358, (Nov. 1996).
Lobsanov et al., "Modulation of activity by Arg407: structure of a fungal alpha-1,2-mannosidase in complex with a substrate analogue," *Acta Crystallogr D Biol Crystallogr.*, 64(Pt 3):227-236, (2008).
Luer and Hatton, "Vancomycin administration into the cerebrospinal fluid: a review ," *Annals of Pharmacotherapy*, 27:912-921, 1993.
Madzak et al., "Strong hybrid promoters and integrative expression/secretion vectors for quasi-constitutive expression of heterologous proteins in the yeast Yarrowia lipolytica," *J Mol Microbiol Biotechnol.*, 2(2):207-216, (Apr. 2000).
Madzak et al., "Heterologous Protein Expression and Secretion in the Non-conventional Yeast Yarrowia lipolytica: A Review," *J. Biotechnol.*, 109:63-81 (2004).
Maras et al., "Molecular cloning and enzymatic characterization of a Trichoderma reesei 1, 2-alpha-D-mannosidase," *J. Biotechnol*, 77: 255-263 (2000).
Martinet et al., "Protection of mice against a lethal influenza challenge by immunization with yeast-derived recombinant influenza neuraminidase," *Eur J Biochem.*, 247(1):332-338, (Jul. 1997).
Merkle et al., Cloning, expression, purification, and characterization of the murine lysosomal acid alpha-mannosidase, *Biochim Biophys Acta.*, 1336(2):132-146, (Aug. 1997).
Moreau et al. "Cell-free transfer of membrane lipids. Evidence for lipid processing," *J. Biol. Chem.* 266(7):4329-4333, (1991).
Moreau et al. "Trafficking of lipids from the endoplasmic reticulum to the Golgi apparatus in a cell-free system from rat liver," *J. Biol. Chem.*, 266(7):4322-4328, (1991).
Mori et al., "Signalling from endoplasmic reticulum to nucleus: transcription factor with a basic-leucine zipper motif is required for the unfolded protein-response pathway," *Genes Cells*, vol. 1, No. 9 (Sep. 1996), pp. 803-817.
Newman and Ferro-Novick, "Characterization of new mutants in the early part of the yeast secretory pathway isolated by a [3H]mannose suicide selection," *J. Cell Biol.*, 105(4):1587-1594, (1987).
Orlean et al., "Cloning and sequencing of the yeast gene for dolichol phosphate mannose synthase, an essential protein," *J. Biol. Chem.*, vol. 263, (Nov. 1988), pp. 17499-17507.
Paulik et al., "Cell-free transfer of the vesicular stomatitis virus G protein from an endoplasmic reticulum compartment of baby hamster kidney cells to a rat liver Golgi apparatus compartment for Man8-9 to Man5 processing," *Arch. Biochem. Biophys.*, 367(2):265-273, (1999).
Platt and Lachmann, "Treating lysosomal storage disorders: Current practice and future prospects," *Biochim Biophys Acta*, 1793(4):737-745, 2009.
Poljak, "Production and structure of diabodies," *Structure*, 2(12):1121-1123, (1994).
Protein Data Bank, "Structure of the GH92 Family Glycosylhydrolase CCMAN5" Deposition: Sep. 29, 2010 [retrieved on Jul. 17, 2012]. Retrieved from the Internet: < URL: http://www.pdb.org/pdb/explore/explore.do?structureId=2XSG>, 2 pages.
Rexach and Schekman, "Distinct biochemical requirements for the budding, targeting, and fusion of ER-derived transport vesicles," *J. Cell Biol.*, 114(2):219-229, (1991).

(56) References Cited

OTHER PUBLICATIONS

Richard et al., "Tagging morphogenetic genes by insertional mutagenesis in the yeast Yarrowia lipolytica," *J Bacteriol.*, 183(10):3098-3107, (May 2001).
Smith and Waterman, "Comparison of biosequences," *Adv. Appl. Math.*, 2(4):482-489, (Dec. 1981).
Song et al., "Characterization of Genes Involved in N-glycosylation in Yarrowia lipolytica," *Yeast*, 20:S147 (2003).
Song et al., "Engineering of the Yeast Yarrowia lipolytica for the Production of Glycoproteins Lacking the Outer-Chain Mannose Residues of N-Glycans," *Appl Environ Microbiol.*, vol. 73, No. 14 (Jul. 2007), pp. 4446-4454.
Sreekrishna et al., "Invertase gene (SUC2) of *Saccharomyces cerevisiae* as a dominant marker for transformation of Pichia pastoris," *Gene*, 59(1):115-125, (1987).
Stocks, "Intrabodies: production and promise," *Drug Discov. Today* 9(22):960-966, (Nov. 2004).
Tremblay and Herscovics, "Cloning and expression of a specific human alpha 1,2-mannosidase that trims Man9GlcNAc2 to Man8GlcNAc2 isomer B during N-glycan biosynthesis," *Glycobiology.*, 9(10):1073-1078, (Oct. 1999).
UniProtKB/Swiss-Prot: P06280.1 GI:113499, "RecName: Full=Alpha-galactosidase A; AltName: Full=Alpha-D-galactosidase A; AltName: Full=Alpha-D-galactoside galactohydrolase; AltName: Full=Melibiase; AltName: INN=Agalsidase; Flags: Precursor," Jun. 13, 2012, 26 pages.
UniProtKB/Swiss-Prot: P15291.5 GI:116241264, "RecName: Full=Beta-1,4-galactosyltransferase 1; Short=Beta-1,4-GalTase 1; Short=Beta4Gal-T1; Short=b4Gal-T1; AltName: Full=UDP-Gal:beta-GlcNAc beta-1,4-galactosyltransferase 1; AltName: Full=UDP-galactose:beta-N-acetylglucosamine beta-1,4-galactosyltransferase . . . " Jun. 13, 2012, 10 pages.
UniProtKB/Swiss-Prot: P26572.2 GI:311033399, "RecName: Full=Alpha-1,3-mannosyl-glycoprotein 2-beta-N-acetylglucosaminyltransferase; AltName: Full=N-glycosyl-oligosaccharide-glycoprotein N-acetylglucosaminyltransferase I; Short=GNT-I; Short=GlcNAc-T I," Apr. 18, 2012, 6 pages.
UniProtKB/Swiss-Prot: P27809.1 GI:127214, "RecName: Full=Glycolipid 2-alpha-mannosyltransferase; AltName: Full=Alpha-1,2-mannosyltransferase," Jun. 13, 2012, 8 pages.
UniProtKB/Swiss-Prot: P38069.1 GI:586137, "RecName: Full=Alpha-1,2-mannosyltransferase MNN2; AltName: Full=Calcium resistance and vanadate sensitivity protein 4; AltName: Full=Mannan synthesis protein MNN2," Jun. 13, 2012, 5 pages.
UniProtKB/Swiss-Prot: Q09326.1 GI:1169978, "RecName: Full=Alpha-1,6-mannosyl-glycoprotein 2-beta-N-acetylglucosaminyltransferase; AltName: Full=Beta-1,2-N-acetylglucosaminyltransferase II; AltName: Full=GlcNAc-T II; Short=GNT-II; AltName: Full=Mannoside acetylglucosaminyltransferase 2; AltName: Full=N-g . . . ," Jun. 13, 2012, 3 pages.
UniProtKB/Swiss-Prot: Q24451.2 GI:32130434, "RecName: Full=Alpha-mannosidase 2; AltName: Full=Golgi alpha-mannosidase II; Short=AMan II; Short=Man II; AltName: Full=Mannosyl-oligosaccharide 1,3-1,6-alpha-mannosidase," Apr. 18, 2012, 13 pages.
UniProtKB/Swiss-Prot: Q9Y7X5.1 GI:74698597, "RecName: Full=Uncharacterized protein C365.14c," May 16, 2012, 2 pages.
Vandersall-Nairn et al., "Cloning, expression, purification, and characterization of the acid α-mannosidase from Trypanosoma cruzi," *Glycobiology*, 8(12):1183-1194, (1998).
Verostek et al., "Glycoprotein biosynthesis in the alg3 *Saccharomyces cerevisiae* mutant. I. Role of glucose in the initial glycosylation of invertase in the endoplasmic reticulum," *The Journal of Biological Chemistry*, vol. 268, (Jun. 5, 1993), pp. 12095-12103.
Verostek et al., "Glycoprotein biosynthesis in the alg3 *Saccharomyces cerevisiae* mutant. II. Structure of novel Man6-10GlcNAc2 processing intermediates on secreted invertase," *The Journal of Biological Chemistry*, vol. 268, pp. 12104-12115, (Jun. 5, 1993).
Vervecken et al. "In Vivo Synthesis of Mammalian-Like, Hybrid-Type N-Glycans in Pichia pastoris," *Appl. Environ. Microb.*, 70(5):2639-2646, (May 2004).
Vocadlo et al., "Mechanistic insights into glycosidase chemistry," *Curr. Opin. Chem. Biol.*, 12:539-555 (2008).
Ward et al., "Characterization of Humanized Antibodies Secreted by *Aspergillus niger*," *Appl. Environ. Microbiol.*, 70(5):2567-2576, (May 2004).
Wheeler et al. "Intrabody and Intrakine Strategies for Molecular Therapy," *Mol. Ther.*, 8(3):355-366, (Sep. 2003).
Yang et al., "Cell-surface display of the active mannanase in Yarrowia lipolytica with a novel surface-display system," *Biotechnol Appl Biochem*, vol. 54, No. 3 (Oct. 2009), pp. 171-176.
Yue et al., "Construction of a new plasmid for surface display on cells of Yarrowia lipolytica," *J Microbiol Methods*, vol. 72, No. 2 (Feb. 2008), pp. 116-123.
Zhu and Zhang, "SCPD: a promotor database of the yeast *Saccharomyces cerevisiae*," *Bioinformatics*, 15(7-8):607-611, (1999).
Zhu et al., "Mechanistic insights into a Ca2+-dependent family of alpha-mannosidases in a human gut symbiont," *Nat. Chem. Biol.*, 6(2):125-132. Epub Dec. 27, 2009 (2010).
Zimm et al., "Cerebrospinal fluid pharmacokinetics of intraventricular and intravenous aziridinylbenzoquinone," *Cancer Research*, 44(4):1698-1701, Apr. 1984.
International Search Report and Written Opinion for PCT/IB2011/002780 mailed Jun. 8, 2012, 11 pages.
International Preliminary Report on Patentability for PCT/IB2011/002780, mailed Jan. 21, 2013, 12 pages.
Choi, et al., "Structural analysis of N-linked oligosaccharides assembled on recombinant proteins secreted from Yarrowia lipolytica Yloch1 and Yloch1 Ylmnn4 mutants.," XXIIth International Conference on Yeast Genetics and Molecular Biology, 09—Protein biosynthesis, maturation, modification and degradation, Yeast, 22:S131, 9-35, 2005.
Aravind and Koonin, "The fukutin family—predicted enzymes modifying cell-surface molecules," Curr Biol., 9(22):R836-R837, Nov. 18, 1999.
Bijvoet et al., "Recombinant human acid alpha-glucosidase: high level production in mouse milk, biochemical characteristics, correction of enzyme deficiency in GSDII KO mice," Hum Mol Genet., 7(11):1815-1824, Oct. 1998.
Cardone et al., "Abnormal mannose-6-phosphate receptor trafficking impairs recombinant alpha-glucosidase uptake in Pompe disease fibroblasts," Pathogenetics, 1(1):6, Dec. 1, 2008.
De Pourcq et al, "Engineering Yarrowia lipolytica to produce glycoproteins homogeneously modified with the universal Man3GlcNAc2 N-glycan core," PLoS One, 7(6):e39976, 12 pages, Epub Jun. 29, 2012.
Ettinger et al., "Intrathecal methotrexate overdose without neurotoxicity: case report and literature review," Cancer, 41(4):1270-1273, Apr. 1978.
Le Dall et al., "Multiple-copy integration in the yeast Yarrowia lipolytica," Curr Genet., 26(1):38-44, Jul. 1994.
Moreland et al., "Lysosomal acid alpha-glucosidase consists of four different peptides processed from a single chain precursor," J Biol Chem., 280(8):6780-6791, Epub Nov. 1, 2004.
Nakadai et al., "Purification and Properties of Alkaline Proteinase from Aspergillus oryzae," Agr. Biol. Chem., 37(12):2685-2694, 1973.
Park et al, "Essential role of YIMPO1, a novel Yarrowia lipolytica homologue of *Saccharomyces cerevisiae* MNN4, in mannosylphosphorylation of N- and O-linked glycans," Appl Environ Microbiol., 77(4):1187-1195, Epub Dec. 23, 2010.
Peberdy et al., "Protein secretion by fungi," Applied Micology and Biotechnology, Agriculture and Food Production, 1:73-114, 2001.
Tiels et al., "A bacterial glycosidase enables mannose-6-phosphate modification and improved cellular uptake of yeast-produced recombinant human lysosomal enzymes," Nat Biotechnol., 30(12):1225-1231, Epub Nov. 18, 2012.

(56) References Cited

OTHER PUBLICATIONS

Van Hove et al., "High-level production of recombinant human lysosomal acid alpha-glucosidase in Chinese hamster ovary cells which targets to heart muscle and corrects glycogen accumulation in fibroblasts from patients with Pompe disease," Proc Natl Acad Sci U S A., 93(1):65-70, Jan. 9, 1996.

Wu et al., Asparagine-linked glycosylational modifications in yeast, Cell Engineering, 3:215-232, 2002.

Zhu et al., "Glycoengineered acid alpha-glucosidase with improved efficacy at correcting the metabolic aberrations and motor function deficits in a mouse model of Pompe disease," Mol Ther., 17(6):954-963, Epub Mar. 10, 2009.

Abe et al., "In vitro oligosaccharide synthesis using intact yeast cells that display glycosyltransferases at the cell surface through cell wall-anchored protein Pir.," Glycobiology, 13(2):87-95, print Feb. 2003, epub Nov. 2002.

Ackerman et al., "Highly avid magnetic bead capture: an efficient selection method for de novo protein engineering utilizing yeast surface display," Biotechnol Prog., 25(3):774-783, May-Jun. 2009.

Almeciga et al., "Production of an active recombinant human N-acetylgalactosamine-6-sulfate sulfatase enzyme in Pichia pastoris," Molecular Genetics and Metabolism, 111(2):S19, Abstract 11, Jan. 27, 2014.

Andrés et al., "Use of the cell wall protein Pir4 as a fusion partner for the expression of Bacillus sp. BP-7 xylanase A in Saccharomyces cerevisiae," Biotechnol Bioeng, 89(6): 690-697, Mar. 2005.

Boder and Wittrup, "Yeast surface display for screening combinatorial polypeptide libraries," Nat. Biotechnol., 15, 553-557, Jun. 1997.

Boder et al. "Directed evolution of antibody fragments with monovalent femtomolar antigen-binding affinity," Proc Natl Acad Sci U S A., 97(20):10701-5, Sep. 2000.

Brady, "Enzyme replacement for lysosmal diseases," Annu. Rev. Med., 57:283-296, 2006.

Brady, "The lipid storage diseases: new concepts and control," Ann Intern Med., 82(2):257-61, Feb. 1975.

Carlson et al., "Function and structure of a prokaryotic formylglycine-generating enzyme," J Biol Chem., 283(29):20117-20125, Epub Apr. 4, 2008.

Chao et al., "Isolating and engineering human antibodies using yeast surface display," Nat. Protoc., 1(2):755-768, 2006.

Chiba et al., "Production of human compatible high mannose-type (Man5GlcNAc2) sugar chains in Saccharomyces cerevisiae," J Biol Chem., 273(41):26298-26304, Oct. 9, 1998.

Cho et al., "Structure of the extracellular region of HER2 alone and in complex with the Herceptin," Nature, 421(6924):756-760, Feb. 2003.

Davidow et al., "Cloning and sequencing of the alkaline extracellular protease gene of Yarrowia lipolytica," J. Bacteriol., 169(10):4621-4629, Oct. 1987.

Dragosits et al., "The effect of temperature on the proteome of recombinant Pichia pastoris," J. Proteome Res., 8(3):1380-1392, Mar. 2009.

Ekici et al., "Unconventional serine proteases: variations on the catalytic Ser/His/Asp triad configuration," Protein Sci., 17(12):2023-2037, Epub Sep. 29, 2008.

Fournier et al., "Scarcity of ars sequences isolated in a morphogenesis mutant of the yeast Yarrowia lipolytica," Yeast, 7(1):25-36, Jan. 1991.

Fujii, "Antibody Affinity Maturation by Random Mutagenesis," Antibody Engineering, vol. 248, pp. 345-359, 2004.

Gasser et al., "Engineering of Pichia pastoris for improved production of antibody fragments," Biotechnol. Bioeng., 94(2):353-361, Jun. 2006.

GenBank Accession No. AAO78636, "putative alpha-1,2-mannosidase [Bacteroides thetaiotaomicron VPI-5482]," 1 page, Oct. 24, 2007.

GenBank Accession No. NP630514, "secreted protein [Streptomyces coelicolor A3(2)]," 2 pages, Sep. 26, 2008.

Grubb et al., "New strategies for enzyme replacement therapy for lysosomal storage diseases," Rejuvenation Res., 13(2-3):229-236, Apr.-Jun. 2010.

Hedstrom, "Serine protease mechanism and specificity," Chem Rev., 102(12):4501-4524, Dec. 2002.

Jaafar et al., "Isolation of the MNN9 gene of Yarrowia lipolytica (YlMNN9) and phenotype analysis of a mutant ylmnn9 Delta strain," Yeast, 20(7):633-644, May 2003.

Klis et al., "Cell wall construction in Saccharomyces cerevisiae," Yeast, 23(3):185-202, 2006.

Landgrebe et al., "The human SUMF1 gene, required for post-translational sulfatase modification, defines a new gene family which is conserved from pro- to eukaryotes," Gene., 316:47-56, Oct. 16, 2003.

Liang et al., "The crystal structures of two cuticle-degrading proteases from nematophagous fungi and their contribution to infection against nematodes," FASEB J., 24(5):1391-1400, Epub Dec. 9, 2009.

Lin et al., "Display of a functional hetero-oligomeric catalytic antibody on the yeast cell surface," App. Microbiol Biotechol., 62(2-3): 226-232, print Aug. 2003, Epub Mar. 2003.

Lobsanov et al., "Structure of Penicillium citrinum alpha 1,2-mannosidase reveals the basis for differences in specificity of the endoplasmic reticulum and Golgi class I enzymes," J Biol Chem., 277(7):5620-5630, Epub Nov. 19, 2001.

Matsuoka et al., "Analysis of regions essential for the function of chromosomal replicator sequences from Yarrowia lipolytica," Mol. Gen. Genet., 237(3):327-333, Mar. 1993.

Morya et al., "In silico characterization of alkaline proteases from different species of Aspergillus," Appl Biochem Biotechnol., 166(1):243-257, Epub Nov. 10, 2011.

Nicaud et al., "Protein expression and secretion in the yeast Yarrowia lipolytica," FEMS Yeast Res., 2(3):371-379, Aug. 2002.

Perona and Craik et al., "Structural basis of substrate specificity in the serine proteases," Protein Sci., 4(3):337-360, Mar. 1995.

Pignède et al., "Characterization of an extracellular lipase encoded by LIP2 in Yarrowia lipolytica," J. Bacteriol., 182(10):2802-10, May 2000.

Rakestraw and Wittrup, "Contrasting secretory processing of simultaneously expressed heterologous proteins in Saccharomyces cerevisiae," Biotechnol. Bioeng., 93(5):896-905, Apr. 2006.

Rawlings and Barrett, "Evolutionary families of peptidases," Biochem J., 290 ( Pt 1):205-218, Feb. 15, 1993.

Rodriguez et al., "Production of recombinant human N-acetylgalactosamine-6-sulfate enzyme in Pichia pastoris," Molecular Genetics and Metabolism, 108(2):S79-S80, Abstract 197, Feb. 1, 2013.

Ruiz-Herrera and Sentandreu, "Different effectors of dimorphism in Yarrowia lipolytica," Arch. Microbiol., 178(6): 477-483, print Dec. 2002, Epub Oct. 2002.

Ryckaert et al., "Isolation of antigen-binding camelid heavy chain antibody fragments (nanobodies) from an immune library displayed on the surface of Pichia pastoris," J Biotechnol., 145(2):93-98, Epub Oct. 2009, print Jan. 2010.

Shusta et al., "Increasing the secretory capacity of Saccharomyces cerevisiae for production of single-chain antibody fragments," Nat. Biotechnol., 16(8): 773-777, Aug. 1998.

Shusta et al., "Yeast polypeptide fusion surface display levels predict thermal stability and soluble secretion efficiency," J. Mol. Biol., 292(5):949-956, Oct. 1999.

Siezen et al., "Subtilases: the superfamily of subtilisin-like serine proteases," Protein Sci., 6(3):501-523, Mar. 1997.

Swennen et al., "Secretion of active anti-Ras single-chain Fv antibody by the yeasts Yarrowia lipolytica and Kluyveromyces lactis," Microbiology, 148(Pt 1):41-50, Jan. 2002.

Tajima et al., "Use of a modified alpha-N-acetylgalactosaminidase in the development of enzyme replacement therapy for Fabry disease," Am J Hum Genet., 85(5):569-580 Epub Oct. 22, 2009.

Tanino et al., "Construction of a Pichia pastoris cell-surface display system using Flo1p anchor system," Biotechnol. Prog., 22(4): 989-993, Jul.-Aug. 2006.

(56) References Cited

OTHER PUBLICATIONS

Ueda et al., "Cell surface engineering of yeast: construction of arming yeast with biocatalyst," *J. Biosci. Bioeng.*, 90(2): 125-136, 2000.
VanAntwerp and Wittrup, "Fine affinity discrimination by yeast surface display and flow cytometry," *Biotechnol. Prog.*, 16(1): 31-7, Jan.-Feb. 2000.
Vega et al., "Partial characterization of α-mannosidase from Yarrowia lipolytica," *J Basic Microbiol.*, 28(6):371-379, ePub Jan. 10, 2007.
Vernis et al., "An origin of replication and a centromere are both needed to establish a replicative plasmid in the yeast Yarrowia lipolytica," *Mol. Cell Biol.*, 17(4): 1995-2004, Apr. 1997.
Wang and Shusta, "The use of scFv-displaying yeast in mammalian cell surface selections," *J. Immunol. Methods*, 304(1-2):30-42, Sep. 2005.
Wang et al., "A new yeast display vector permitting free scFv amino termini can augment ligand binding affinities," *Protein Eng. Des. Sel.*, 18(7): 337-343, print Jul. 2005, Epub Jun. 2005.
Wang et al., "Construction of a novel Pichia pastoris cell-surface display system based on the cell wall protein Pir1," *Curr. Microbiol.*, 56(4): 352-357, Apr. 2008.
Wright et al., "Structure of subtilisin BPN' at 2.5 angström resolution," *Nature*, 221(5177):235-242, Jan. 18, 1969.
Yeung and Wittrup, "Quantitative screening of yeast surface-displayed polypeptide libraries by magnetic bead capture," *Biotechnol. Prog.*, 18(2):212-220, Mar.-Apr. 2002.
Ying et al., "Soluble monomeric IgG1 Fc," *J Biol Chem.*, 287(23):19399-19408, Epub Apr. 19, 2012.
Zhu et al., "Mechanistic insights into a Ca2+-dependent family of alpha-mannosidases in a human gut symbiont," *Nat. Chem. Biol.*, 6(2):125-132. Supplementary Information, 25 pages. Epub 2009 Dec. 27, 2010.
"Glycoside Hydrolase Family 38," cazy.org [online] captured Sep. 11, 2010. Retrieved from the Internet: <URL: http://www.cazy.org/GH38.html>, 1 page.
"Glycoside Hydrolase Family 47," cazy.org [online] captured Sep. 12, 2010. Retrieved from the Internet: <URL: http://www.cazy.org/GH47.html>, 1 page.
"Glycoside Hydrolase Family 92," cazy.org [online] captured Sep. 12, 2010. Retrieved from the Internet: <URL: http://www.cazy.org/GH92.html>, 1 page.
Bourbonnais et al., "Production of full-length human pre-elafin, an elastase specific inhibitor, from yeast requires the absence of a functional yapsin 1 (Yps1p) endoprotease," *Protein Expr Purif.*, 20(3):485-491, Dec. 2000.
Cantarel et al., "The Carbohydrate-Active EnZymes database (CAZy): an expert resource for Glycogenomics," *Nucleic Acids Res.*, 37(Database issue):D233-D238, Epub Oct. 5, 2008.
De Pourcq et al., "Engineering the yeast Yarrowia lipoytica for the production of therapeutic proteins homogeneously glycosylated with Man8GIcNAc2 and Man5GIcNAc2," *Microbial Cell Factories*, 11:53, 1-12, May 1, 2012.
Gagnon-Arsenault et al., "Activation mechanism, functional role and shedding of glycosylphosphatidylinositol-anchored Yps1p at the *Saccharomyces cerevisiae* cell surface," *Mol Microbiol.*, 69(4):982-993, Epub Jun. 28, 2008.
Gagnon-Arsenault et al., "Fungal yapsins and cell wall: a unique family of aspartic peptidases for a distinctive cellular function," *FEMS Yeast Res.*, 6(7):966-978, Nov. 2006.
Gatlin et al., "Automated identification of amino acid sequence variations in proteins by HPLC/microspray tandem mass spectrometry," *Anal Chem.*, 72(4):757-763, Feb. 15, 2000.
GenBank Accession No. XP503768, GI: 50552716, "YALI0E10175p [Yarrowia lipolytica CLIB122]," Oct. 29, 2008, 2 pages.
GenBank, "Yarrowia lipolytica CLIB122 [gbpln]: 5967 CDS's (2945919 codons)," Codon Usage Database, [online], Jun. 15, 2007 [retrieved on Aug. 15, 2014]. Retrieved from the Internet: <URL: http://www.kazusa.or.jp/codon/cgi-bin/showcodon.cgi?species=284591>, 1 page.
Gilbert, "Glycoside Hydrolase Family 92," CAZypedia [online], Mar. 4, 2010. Retrieved from the Internet: <URL: http://www.cazypedia.org/index.php/Glycoside_Hydrolase_Family_92>, 3 pages.
Henrissat, "A classification of glycosyl hydrolases based on amino acid sequence similarities," *Biochem J.*, 280 ( Pt 2):309-316, Dec. 1, 1991.
Komeda et al., "Construction of protease-deficient Candida boidinii strains useful for recombinant protein production: cloning and disruption of proteinase A gene (PEP4) and proteinase B gene (PRBI)," *Biosci Biotechnol Biochem.*, 66(3):628-631, Mar. 2002.
Kuroda et al., "Antibody expression in protease-deficient strains of the methylotrophic yeast Ogataea minuta," *FEMS Yeast Res.*, 7(8):1307-1316. Epub Aug. 22, 2007.
Li et al., "Optimization of humanized IgGs in glycoengineered Pichia pastoris," *Nat. Biotechnol.*, 24(2):210-215, Epub Jan. 22, 2006.
Liu et al., "Disruption of the OCH1 and MNN1 genes decrease N-glycosylation on glycoprotein expressed in Kluyveromyces lactis," *J Biotechnol.*, 143(2):95-102, Epub Jun. 24, 2009.
Mast and Moremen, "Family 47 alpha-mannosidases in N-glycan processing," *Methods Enzymol.*, 415:31-46, 2006.
Mille et al., "Identification of a new family of genes involved in beta-1,2-mannosylation of glycans in Pichia pastoris and Candida albicans," *J Biol Chem.*, 283(15):9724-9736. Epub Jan. 30, 2008.
Penttilä et al., "Expression of two Trichoderma reesei endoglucanases in the yeast *Saccharomyces cerevisiae*," *Yeast.*, 3(3):175-185, Sep. 1987.
Potgieter et al., "Production of monoclonal antibodies by glycoengineered Pichia pastoris," *J Biotechnol.*, Feb. 23, 2009;139(4):318-325, Epub Dec. 27, 2008.
Rose, "Glycoside Hydrolase Family 38," CAZypedia [online], Feb. 2, 2010. Retrieved from the Internet: <URL: http://www.cazypedia.org/index.php/Glycoside_Hydrolase_Family_38>, 3 pages.
Swennen et al., "Folding proteome of Yarrowia lipolytica targeting with uracil permease mutants," *J Proteome Res.*, 9(12):6169-6179, Epub Nov. 12, 2010.
Swiss Protein Accession No. P15291, Nov. 30, 2010, 9 pages.
Swiss Protein Accession No. P26572, Nov. 30, 2010, 4 pages.
Swiss Protein Accession No. P38069, Nov. 30, 2010, 3 pages.
Swiss Protein Accession No. Q09326, Nov. 30, 2010, 3 pages.
Swiss Protein Accession No. Q24451, Nov. 30, 2010, 12 pages.
van den Elsen et al., "Structure of Golgi alpha-mannosidase II: a target for inhibition of growth and metastasis of cancer cells," *EMBO J.*, 20(12):3008-3017, Jun. 15, 2001.
Vervecken et al., "Modification of the N-glycosylation pathway to produce homogeneous, human-like glycans using GlycoSwitch plasmids," *Methods Mol Biol.*, 389:119-138, 2007.
YALI0A16819g YALI0A16819p[Yarrowia lipolytica CLIB122] Gene ID: 2906333, created on Jul. 24, 2004, 2 pages.
YALI0C10135g YALI0C10135p[Yarrowia lipolytica CLIB122] Gene ID: 7009445, created on Oct. 29, 2008, 2 pages.
YALI0D10835g YALI0D10835p[Yarrowia lipolytica CLIB122] Gene ID: 2910442, created on Jul. 24, 2004, 2 pages.
YALI0E10175g YALI0E10175p[Yarrowia lipolytica CLIB122] Gene ID: 2912589, created on Jul. 28, 2004, 2 pages.
YALI0E20823g YALI0E20823p[Yarrowia lipolytica CLIB122] Gene ID: 2911836, created on Jul. 28, 2004, 2 pages.
YALI0E22374g YALI0E22374p[Yarrowia lipolytica CLIB122] Gene ID: 2912981, created on Jul. 28, 2004, 2 pages.
YALI0E24981g YALI0E24981p[Yarrowia lipolytica CLIB122 Gene ID: 2912672, created on Jul. 28, 2004, 2 pages.
YALI0E34331g YALI0E34331p[Yarrowia lipolytica CLIB122] Gene ID: 2912367, created on Jul. 28, 2004, 2 pages.
Yao et al., "Degradation of HSA-AX15(R13K) when expressed in Pichia pastoris can be reduced via the disruption of YPS1 gene in this yeast," *J Biotechnol.*, Jan. 15, 2009;139(2):131-136. Epub Oct. 8, 2008.
Cregg et al., "Transformation," *Molecular Biology: Pichia Protocols*, Chapter 3, Humana Press, Totowa, N.J., pp. 27-39 (1998).

(56) References Cited

OTHER PUBLICATIONS

Dierks et al., "Multiple sulfatase deficiency is caused by mutations in the gene encoding the human C(alpha)-formylglycine generating enzyme," *Cell*, 113(4):435-444, May 16, 2003.
Dierks et al., "Sequence determinants directing conversion of cysteine to formylglycine in eukaryotic sulfatases," *EMBO J.*, 18(8):2084-2091, Apr. 15, 1999.
Diez-Roux and Ballabio, "Sulfatases and human disease," *Annu Rev Genomics Hum Genet.*, 6:355-379, 2005.
Floudas, "Computational methods in protein structure prediction," Biotechnology and Bioengineering, 97(2): 207-213, Jun. 1, 2007.
Fraldi et al., "Multistep, sequential control of the trafficking and function of the multiple sulfatase deficiency gene product, SUMF1 by PDI, ERGIC-53 and ERp44," *Hum Mol Genet.*, 17(17):2610-2621, Epub May 28, 2008.
Gande et al., "Paralog of the formylglycine-generating enzyme—retention in the endoplasmic reticulum by canonical and noncanonical signals," *FEBS J.*, 275(6):1118-1130, Epub Feb. 6, 2008.
GenBank Accession No. BAA00258.1 GI:217809, "alkaline protease, partial [Aspergillus oryzae]," Dec. 20, 2002, 2 pages.
GenBank Accession: CAC87611.1, "ERp44 protein [*Homo sapiens*]," 2 pages, Oct. 7, 2008.
Grove et al., "In vitro characterization of AtsB, a radical SAM formylglycine-generating enzyme that contains three [4Fe-4S] clusters," *Biochemistry*, 47(28):7523-7538, Epub Jun. 18, 2008.
Guo et al., "Protein tolerance to random amino acid change," *Proc Natl Acad Sci U S A.*, 101(25):9205-9210, Epub Jun. 14, 2004.
InterPro—Protein sequence anaylsis and classification, "Species: Sulfatase-modifying factor enzyme (IPR005532)," EMBL-EBI, [online]. Retrieved from the Internet: <URL: http://www.ebi.ac.uk/interpro/entry/IPR005532/taxonomy;jsessionid=A50B4C8B868FB85867E9D179F3959BED>, 2 pages, retrieved on Nov. 3, 2015.
Mariappan et al., "ERp44 mediates a thiol-independent retention of formylglycine-generating enzyme in the endoplasmic reticulum," *J Biol Chem.*, 283(10):6375-6383, Epub Jan. 4, 2008.
NCBI Reference Sequence: NP000909.2, "protein disulfide-isomerase precursor [*Homo sapiens*]," Mar. 24, 2012, 4 pages.
NCBI Reference Sequence: XP502492.1, "YALI0D06589p [Yarrowia lipolytica CLIB122]," 2 pages, Oct. 29, 2008.
NCBI Reference Sequence: XP502939.1, "YALI0D17424p [Yarrowia lipolytica CLIB122]," 2 pages, Oct. 29, 2008.
Nett et al., "A combinatorial genetic library approach to target heterologous glycosylation enzymes to the endoplasmic reticulum or the Golgi apparatus of Pichia pastoris," *Yeast.*, 28(3):237-252, Epub Jan. 6, 2011.
Rabuka et al., "Site-specific chemical protein conjugation using genetically encoded aldehyde tags," *Nat Protoc.*, 7(6):1052-1067, May 10, 2012.
Roeser et al., "A general binding mechanism for all human sulfatases by the formylglycine-generating enzyme," *Proc Natl Acad Sci U S A.*, 103(1):81-86, Epub Dec. 20, 2005.
Sakuma et al., "HpSumf1 is involved in the activation of sulfatases responsible for regulation of skeletogenesis during sea urchin development," *Dev Genes Evol.*, 221(3):157-166, Epub Jun. 27, 2011.
Sardiello et al., "Sulfatases and sulfatase modifying factors: an exclusive and promiscuous relationship," *Hum Mol Genet.*, 14(21):3203-3217, Epub Sep. 20, 2005.
Voznyi et al., "A fluorimetric enzyme assay for the diagnosis of MPS II (Hunter disease)," *J Inherit Metab Dis.*, 24(6):675-680, Nov. 2001.

Zito et al., "Sulphatase activities are regulated by the interaction of sulphatase-modifying factor 1 with SUMF2," *EMBO Rep.*, 6(7):655-660, Jul. 2005.
U.S. Appl. No. 13/499,061, filed Sep. 6, 2012, Callewaert.
U.S. Appl. No. 13/620,259, filed Sep. 14, 2012, Callewaert.
U.S. Appl. No. 13/620,306, filed Sep. 14, 2012, Callewaert.
U.S. Appl. No. 13/876,769, filed Mar. 28, 2013, Piens.
U.S. Appl. No. 14/773,234, filed Sep. 4, 2015, Vervecken, pending.
GenBank Accession No. AA034683, "mi41c04.r1 Soares mouse embryo NbME13.5 14.5 Mus musculus cDNA clone Image:466086 5-, mRNA sequence," Aug. 23, 1996, 2 pages.
GenBank Accession No. BAJ83907, "sulfatase modifying factor 1 [Hemicentrotus pulcherrimus]," Nov. 10, 2011, 2 pages.
GenBank Accession No. ELW48757.1, GI: 444707484, "Sulfatase-modifying factor 1 [Tupaia chinensis]," Jan. 31, 2013, 2 pages.
GenBank Accession No. ENN77245.1, GI: 478257082, "hypothetical protein YQE06075, partial [Dendroctonus ponderosae]," Apr. 10, 2013, 2 pages.
GenBank Accession No. NP001069544, "sulfatase-modifying factor 1 precursor [Bos taurus]," Jan. 23, 2012, 2 pages.
GenBank Accession No. NP215226.1, "unnamed protein product [Mycobacterium tuberculosis H37Rv]," Jan. 19, 2012, 2 pages.
GenBank Accession No. NP631591.1, "hypothetical protein SCO7548 [Streptomyces coelicolor A3(2)]," Jan. 19, 2012, 2 pages.
GenBank Accession No. XP001374411, GI: 126336367, "Predicted: sulfatase-modifying factor 1-like [*Monodelphis domestica*]," May 31, 2011, 1 page.
GenBank Accession No. XP003642070.1, GI: 363738801, "Predicted: sulfatase-modifying factor 1-like [Gallus gallus]," Dec. 16, 2011, 1 pages.
GenBank Accession No. XP005511340.1, GI: 543740918, "Predicted: sulfatase-modifying factor 1 [Columba livia]," Sep. 15, 2013, 2 pages.
GenBank Accession No. XP504265.1, GI: 50553708, "YALI0E22374p [Yarrowia lipolytica CLIB122]," Oct. 29, 2008, 2 pages.
Kim et al., "Functional characterization of the Hansenula polymorpha HOC1, OCH1, and OCR1 genes as members of the yeast OCH1 mannosyltransferase family involved in protein glycosylation," J Biol Chem., 281(10):6261-6272, Epub Jan. 10, 2006.
UniProtKB/Swiss-Prot: P01588, "Erythropoietin precursor (Epoetin)," Jul. 21, 1986, 7 pages.
UniProtKB/Swiss-Prot: P04062, "Glucosylceramidase precursor (Beta-glucocerebrosidase) (Acid beta-glucosidase) (D-glucosyl-N-acylsphingosine glucohydrolase) (Alglucerase) (Imiglucerase)," Nov. 1, 1986, 31 pages.
Database Geneseq, "Aspergillus oryzae alkaline protease, SEQ ID 1.", retrieved from EBI accession No. GSP:ARW11112, Database accession No. ARW11112, 1 page, Aug. 7, 2008.
García-Gómez et al., "Advantages of a proteolytic extract by Aspergillus oryzae from fish flour over a commercial proteolytic preparation," Food Chemistry, 112(3):604-608, Feb. 1, 2009.
Moreland et al., "Species-specific differences in the processing of acid α-glucosidase are due to the amino acid identity at position 201," Gene, 491(1):25-30, Jan. 1, 2012.
Herscovics., "Processing glycosidases of Saccharomyces cerevisiae," Biochimica Biophysica. Acta., 1426(2):275-285, Jan. 6, 1999.
Korean Grounds for Rejection in Korean Patent Application No. 10-2009-7022979, dated Feb. 10, 2017, 4 pages with English translation.
Korean Grounds for Rejection in Korean Patent Application No. 10-2015-7035851, dated Feb. 10, 2017, 4 pages with English translation.

(56) References Cited

OTHER PUBLICATIONS

Odani et al., "Cloning and analysis of the MNN4 gene required for phosphorylation of N-linked oligosaccharides in Saccharomyces cerevisiae," *Glycobiology.*, 6(8):805-810, Dec. 1996.

Odani et al., "Mannosylphosphate transfer to cell wall mannan is regulated by the transcriptional level of the MNN4 gene in Saccharomyces cerevisiae," *FEBS Letters.*, 420(2-3):186-190, Dec. 29, 1997.

\* cited by examiner

FIGURE 1A

ATGAAGCTTTCCACCATCCTCTTCACAGCCTGCGCTACCCTGGCTGCCGCCCAGCAGGGAGCCT
CTCGACCCGGACCCCGAGATGCCCAGGCTCACCCCGGACGACCTCGAGCTGTGCCCACCCAGTGTG
ACGTGCCCCCCAACTCTCGATTCGACTGTGCCCCCGACAAGGCCATCACCCAGGAGCAGTGCGAGG
CCCGAGGCTGTTGTTACATCCCCGCTAAGCAGGGCCTGCAGGGCGCTCAGATGGGCCAGCCCTGGT
GTTTCTTCCCCCCCTCTTACCCCTCCTACAAGCTGGAGAACCTGTCCTCTTCGGAGATGGGCTACAC
CGCCACCCTGACCCGAACCACCCCCACCTTTTTCCCCAAGGACATCCTGACCCTGCGACTGGACGTG
ATGATGGAGACCGAGAACCGACTGCACTTCACCATCAAGGACCCCGCCAACCGACGATACGAGGT
GCCCCTGGAGACCCCCACGTGCACTCTCGAGCCCCTTCCCCCCTGTACTCTGTGGAGTTCTCTGAG
GAGCCCTTCGGCGTGATCGTGCGACGACAGCTGGACGGCCGAGTGCTGCTGAACACCACCGTGGCC
CCCCTGTTCTTCGCCGACCAGTTCCTGCAGCTGTCTACCTCTCTGCCCTCTCAGTACATCACCGGCCT
GGCCGAGCACCTGTCCCCCCTGATGCTGTCCACCTCTTGGACTCGAATCACCCTGTGGAACCGAGA
CCTGGCCCCCACCCCCGGTGCCAACCTGTACGGCTCTCACCCCTTCTACCTGGCCCTGGAGGACGGC
GGCTCTGCCCACGGCGTGTTTCTGCTGAACTCTAACGCCATGGACGTGGTGCTGCAGCCCTCTCCCG
CCCTGTCTTGGCGATCTACCGGCGGCATCCTGGACGTGTACATCTTCCTGGGCCCTGAGCCCAAGTC
TGTGGTCCAGCAGTACCTGGACGTGGTCGGATACCCCTTCATGCCCCCCTACTGGGGCCTGGGCTTC
CACCTGTGTCGATGGGGCTACTCTTCTACCGCCATCACCCGACAGGTGGTGGAGAACATGACCCGA
GCCCACTTCCCCCTGGACGTGCAATGGAACGACCTGGACTACATGGACTCTCGACGAGACTTCACC
TTCAACAAGGACGGCTTCCGAGACTTCCCCGCCATGGTCCAGGAGCTGCACCAGGGAGGACGACG
ATACATGATGATCGTGGACCCCGCCATCTCTTCTTCCGGACCCGCCGGATCTTACCGACCCTACGAC
GAGGGCCTGCGACGAGGCGTGTTCATCACCAACGAGACCGGCCAGCCCCTGATCGGCAAGGTGTG
GCCCGGCTCTACCGCCTTCCCCGACTTCACCAACCCCACCGCCCTGGCTTGGTGGGAGGACATGGT
GGCCGAGTTCCACGACCAGGTGCCCTTCGACGGCATGTGGATCGACATGAACGAGCCCTCTAACTT
CATCCGAGGCTCTGAGGACGGCTGTCCCAACAACGAGCTGGAGAACCCCCCCTACGTGCCCGGCGT
GGTGGGCGGAACCCTGCAGGCCGCCACCATCTGTGCCTCTTCGCACCAGTTTCTGTCTACCCACTAC
AACCTGCACAACCTGTACGGACTGACCGAGGCCATTGCCTCTCACCGAGCCCTGGTGAAGGCCCGA
GGCACCCGACCCTTCGTGATCTCTCGATCTACCTTCGCCGGCCACGGCCGATACGCCGGACACTGG
ACCGGCGATGTGTGGTCCTCTTGGGAGCAGCTGGCCTCTTCTGTGCCCGAGATCCTGCAGTTCAACC
TGCTGGGCGTGCCCCTGGTGGGCGCCGACGTGTGTGGCTTCCTGGGCAACACCTCTGAGGAGCTGT
GTGTTCGATGGACCCAGCTCGGCGCCTTCTACCCTTTCATGCGAAACCACAACTCCCTGCTGTCTCT
GCCCCAGGAGCCCTACTCGTTCTCTGAGCCCGCTCAGCAGGCCATGCGAAAGGCTCTGACCCTGCG
ATACGCCCTGCTGCCCCACCTGTACACCCTGTTCCACCAGGCCACGTGGCTGGAGAGACCGTGGC
CCGACCCCTGTTCCTGGAGTTCCCTAAGGACTCTTCTACCTGGACCGTGGACCATCAGCTGCTGTGG
GGCGAGGCCCTCCTGATCACCCCCGTGCTGCAGGCCGGCAAGGCTGAGGTGACCGGCTACTTCCCT
CTGGGCACCTGGTACGACCTGCAGACCGTGCCTGTGGAGGCCCTGGGATCTCTGCCCCCTCCTCCCG
CCGCTCCCCGAGAGCCCGCCATCCACTCTGAGGGCCAGTGGGTGACCCTGCCCGCTCCCCTGGACA
CCATCAACGTGCACCTGCGAGCCGGCTACATCATCCCTCTGCAGGGACCCGGCCTGACCACCACCG
AGTCTCGACAGCAGCCCATGGCCCTGGCCGTGGCTCTGACCAAGGGCGGAGAGGCCCGAGGCGAG
CTGTTCTGGGACGATGGCGAGTCTCTGGAGGTGCTGGAGCGAGGCGCCTACACCCAGGTGATCTTT
CTGGCCCGAAACAACACCATCGTGAACGAGCTGGTGCGAGTGACCTCTGAGGGCGCTGGTCTGCAG
CTCCAGAAGGTGACCGTCCTGGGCGTGGCCACCGCTCCCCAGCAGGTCCTGTCTAACGGCGTGCCC
GTGTCTAACTTCACCTACTCTCCCGACACCAAGGTGCTGGACATCTGTGTGTCTCTGCTGATGGGCG
AGCAGTTCCTGGTGTCTTGGTGTTAAC

FIGURE 1B

MKLSTILFTACATLAAAQQGASRPGPRDAQAHPGRPRAVPTQCDVPPNSRFDCAPDK
AITQEQCEARGCCYIPAKQGLQGAQMGQPWCFFPPSYPSYKLENLSSSEMGYTATLTRT
TPTFFPKDILTLRLDVMMETENRLHFTIKDPANRRYEVPLETPHVHSRAPSPLYSVEFSE
EPFGVIVRRQLDGRVLLNTTVAPLFFADQFLQLSTSLPSQYITGLAEHLSPLMLSTSWTR
ITLWNRDLAPTPGANLYGSHPFYLALEDGGSAHGVFLLNSNAMDVVLQPSPALSWRST
GGILDVYIFLGPEPKSVVQQYLDVVGYPFMPPYWGLGFHLCRWGYSSTAITRQVVENM
TRAHFPLDVQWNDLDYMDSRRDFTFNKDGFRDFPAMVQELHQGGRRYMMIVDPAISS
SGPAGSYRPYDEGLRRGVFITNETGQPLIGKVWPGSTAFPDFTNPTALAWWEDMVAEF
HDQVPFDGMWIDMNEPSNFIRGSEDGCPNNELENPPYVPGVVGGTLQAATICASSHQF
LSTHYNLHNLYGLTEAIASHRALVKARGTRPFVISRSTFAGHGRYAGHWTGDVWSSWE
QLASSVPEILQFNLLGVPLVGADVCGFLGNTSEELCVRWTQLGAFYPFMRNHNSLLSLP
QEPYSFSEPAQQAMRKALTLRYALLPHLYTLFHQAHVAGETVARPLFLEPPKDSSTWT
VDHQLLWGEALLITPVLQAGKAEVTGYFPLGTWYDLQTVPVEALGSLPPPPAAPREPAI
HSEGQWVTLPAPLDTINVHLRAGYIIPLQGPGLTTTESRQQPMALAVALTKGGEARGEL
FWDDGESLEVLERGAYTQVIFLARNNTIVNELVRVTSEGAGLQLQKVTVLGVATAPQQ
VLSNGVPVSNFTYSPDTKVLDICVSLLMGEQFLVSWC*

FIGURE 3-1

>DsbA-6xHis-CcMan5 (107bp - 5167bp, direct) 5061bp From pLSAHCcMan5
ATGAAAAAGATTTGGCTGGCGCTGGCTGGTTTAGTTTTAGCGTTTAGCGCATCGGCCGG
CCATCACCATCATCACCACGTGGGGCCCGGCTCGGACGAAGTGGATGCACCGGAACCTC
CGAGCGCAGATTATGCAAGCCTGGTTGATGTTTTGTTGGCACCGAAGGTGATTTTGGT
AATGATATGCCTGCAGCACAGGCACCGAATGGTCTGGCAAAAGTTAATCCGCGTACCAC
ACCGGGTCGTAATAATACCGGTTATGATTATGCCCAGAGCAAAATTAGCGGTTTTACCC
ATACCAATCTGGATGGTGTTGGTGGTAGCGGTGGTGGTGGTGATCTGCTGGTTGTTCCG
ACCAGCGGTAGCTATACCGCACGTCCGGGTACAGGCACCTATGCACATCCGTTTAGCCA
TGATGATGAAGATGCAGGTCCGGGTTTTATAGCGTTGGTCTGGGTAATGTTGCAGGCA
CCGATGGTGCAATTACCGGTGCTCCGGGTACAATTGAAGCAGAAGTTGCAGCAGCAACC
CGTAGCGGTGTTCATCGTTATGCATTTCCGGCAGGTAGCACCCCGAGCCTGGTTGTTGA
TCTGGAAACCAATAATACCAGCCGTCGTAGCAGCAGCGTTCAGGTTGAAACCCGTGCAG
ATGGCACCGTTGAACTGAGCGGTCAGGTTACCGGCTATTTTATAATGCAGCCTATACC
CTGTATTATACCGCACGCACCCTGCAGCCTGCAACCGTTCAGACCTGGGGTGATGATGA
TCGTCTGGTTGATGCAACCGCACAGGATGGTGTTGATACCGGTGCAATTCTGACCTTTG
ATCCGGCAGATGCCGGTGAAATTGGTCTGCAGGTTACCCTGTCTCCGGTTAGCGTTGAA
CAGGCACGTATTGATCAGCAGGTTGAACTGGGTGATCTGAGCTTTGATGCAATTCGTGA
TCGTACCCGTGCAGAATGGAATGCAACCCTGGGTCGTGTTGCAATTGATGCAAGCACCG
CAACCGATCCGACCGGTGAACTGCAGCGTCTGTTTATACCCATCTGTATCGCATGTTT
GCAATGCCGATGAATGCAACCAGCACCAGCGGCACCTATCGTGGTGTTGATGGTGCAGT
TCATGCAGCACAGGGCTTTACCTATTATGATAGCTGGGCAACCTGGGATGATTTTCGCA
AATTTAGCGTGATTGCCTATATTGATCCGGCACTGTATCGTGATATGGTTCAGAGCCTG
GTTTACCTGTTTGCAGATGCAGAAGCAACCGGTACAGGCGGTGGTCTGGGTGGTTTTGT
TCATAGCGTTCCGACCGTTCGTTGGGAACGTAGCAGCGTTGTTGTTGCAGATGCAATTG
CCAAAGGCTTTGATGGTTTTGATCGTCTGGATGAAGCATATCCGGCACTGCAGCGCCTG
GTTGGTCAGTATAGCGCAGATGAACTGCGTCGTGGTTATGTTGCAGGTAATCCGGGTGC
AAGCGTTCAGCGTGGTTATGATCAGTATGGTCTGAGCGTTATTGCCGATGAACTGGGTC
TGACCGAAGAAGCAGAAACCCTGCGCGAACAGGCAAGCTGGCCGATTGAAAAACTGACC
AAACCGGGTGCATGGACCGCAGCAGATGGTACACAGGTTGGTCTGCTGACACCGCGTGC
AGCCGATGGTAGCTGGCAGAGCGCAGATCATGCCAAATTTGAAGCAGCAGGTCTGTATC
AGGGCACCCTGTGGCAGTATCATTGGTATGATGCCTATGATATGGATGCACTGGTTGAA
GCAATGGGTGGTCATGAAGCAGCCCGTCTGGGTATGCGTCATATGTTTGGTGAACATGC
ACCGGATGATGGTAAAGCAATGCTGCATAGCAATGCCAATGAAATTGATCTGCAGGCAC
CGTACCTGTTTAATTATACCGGTGAACCGAGCCTGACCCAGAAATGGGCACGTGCAATT
TATACCAAAGAAACCTGGAATCGCTATATTGCAACCGGTAGCAGCTCTGCAGTTCCGTC
AGGTGGTGGTGAATTTACACCTCCGCTGAAAACCAAAGTTTATCGTCTGGACCCTCGTG
GTATGCTGCCGACCATGGATAATGATGCAGGTACAATGAGCACCATGTTTGTTGCAGCA
GCCGTTGGTCTGTTTCCGGTTACCGCAGGTAGCAGCCAGTTTCAGGTTGGTAGCCCGTT
TTTTGATAGCACCACCATTACCTATGATGATGGTAGCGCATTTACCGTTACCGCAGATG
GTGTTAGCGAAGATGCCTTTTATGTTCAGAGCGCAACCCTGGATGGTGCAACCTTTGGT
AATACCTGGGTTGATTATGCAACCGTTGTTGGTGGTGCAGATCTGGCATTTCGTATGGG
TGAACAGCCGAGCGATTGGGGCACCGATACCGCACCGGCATTTAGCATGAGCACCGCCA
CCGATGAACCGGCAGAAGGTCCTCGCGTTAGCGCAGAACCGACCACCGTGCAGACCGGT
GATGGTGGTGCACTGGATGCAACCGTTACCCTGACACTGGATGGCGCACGTCTGGCAGC

FIGURE 3-2

```
ACCGGCAGGTACAGATCTGGTTACCAGCGGTGCAGCAAGCGTTGTTGGTCTGCCGGATG
GTGTTACCGCAGCAGTTACCGTTGCAAGCCCGACCGCACTGACCGTTAGCCTGACCGGC
ACCGCATCAGCAGATGCACGTTTTTTGTGCATCTGCGTGATGCAGCACTGGCCGATGG
TGTTGCAGCCGCAAGCCTGCAGGGTCAGGGTGTTAGCGTTCGTTCTCCGCTGCGTCTGA
GCGTTGCAAGCGCAGAACGTGATGCACTGGCAGCACTGGTTGATGATGCCGTTCTGGTT
CGTCATGGTAATTATAGCAGCGTTACCTTTGATCGTTTAGCACCGCTCTGACAAAAGCA
CAGGAAGCACTGGGCGACGAAGCAGCAACCAGCATTGCACTGCGTTTTGCAGCAGATCG
TCTGGGTGCAGCAGCAGATGCACTGGATCTGACCGGTGGTGGTTATCGTACCCTGGAAG
CAGAACAGAGCGAAGCATGGTCTGGTGGTGAACTGAAAAATGAAGCCAATAGCAGCAGC
GGTAATCTGGGTGGTGTTCGTAGCGGTAGCTGGGTTCAGTATCGCGATATGACCTTTGA
AACCGCAGCCGGTGATACACCTCCGCGTTTTCTGACCGTTCGTTATGATACCAGCTTTG
CACCGACCGATACCCCGAGCACCGTTCGTGTTCATGCCGGTGATGTTTCTGGTCCGGTT
GTTGCAACCGTTGATCTGAAAGGCACCAGCGGTTGGGGTAAATATACCGAAGTTACCGC
AGAACTGGGTGATGTTCAGGCCCTGGTTGATGCCCAGGTTGTTACCTTTGAACTGCTGG
CACCGAGCGGTCGTAGCTGGGTTGGTAATTTTGATTGGTTTCGCTTTAGCGCAGAAGAT
CCGGCAGCACCGGGTCAGCCTGGTGAAAGCCCGACCGTTACCATTGAAGCCGAAGATTG
GACCGCAAGCAGCGGTCGTGGTCTGAAAAAAGAAAGCAGCACCTGGACCAGCGGTCCGG
TGACCAATGTTGGTGGTACAGCAGATGGTGATTGGATTGCCTATGGTGAAGTTGATCTG
GGTGAACTGCCGCTGGGCGAACTGAGCGTTCATTATGTGCATAATAGCAATCGCAGCGG
TAATAATAGCGCACTGAGCGTTTATCTGGATGCATTTGATCCGGCTAATCCGGGTGAAC
CGTTTGTTACCGTTCCGCTGCCGACCACCGGTAGCAGTTGGACCGCAGATGGCACAGCC
ACCGTTGTTCTGCCGGAAACCGTGCAGGGCACCCATGAAGTTTTTGTTCGTCTGAGCAC
CGAACCGTATGCAGATCATCCGTATGTTGCAAATCTGGATAGCCTGACCTTTGCACCGG
GTGGTCCGACCAGCGTTGTGGTTGAAAGCGAAGCCTGGACCAGCAATTCTGGTCGTGGC
CTGAAAAATGAATCTTCTACCTGGACCTCTGGTCCGGTTACAAATGTGGGTGGCACCGC
TGATGGCGATTGGCTGGCATATGGCGAAATTGATCTGGGCAGCGCAGCACTGGATCAGC
TGTCTGTGCATTATGTTCATAATTCTAATCGCTCTGGTCGTAATTCTGCACTGTCTGTG
TATCTGGATGCCTTTGATCCGGCAAATCCGGGTGAACCGTTTGTGACAGTGCCGCTGGC
AAATACCGGTAGCTCTTGGACCACCGATGGTACTGCAGTTGTGGATCTGCCGTCTACCG
TTCGTGGTAAACATCAGGTTTGGGTTCGTCTGTCTACCGAAGCATATGCCGATCATCCG
TATGTGGCCAATCTGGATTCTATGCGCTTTTTTACCGATGCATATGATGTTGAAGTTCC
TCCGACCGATACAGCAGCACTGGCAGCCGTTGTTGATGCAGCAGGTACACCGGAAGCAG
AAATTGCACGTTATGGTCGTATTGATGCCCGTGTTTTTACCCGTGAACTGGCAGCAGCA
CGTAGCGTTCTGGCCGATGCCGGTGCAACACAGGCACAGGCAGATGAACGTGCTCGTCG
TCTGGGTCTGGCAACCGATCAGCTGGTTCCGGCAGAACGTCGTCGTCTGGAAAATCTGG
TTGCCAGCGCAGAAGCACTGACCGACGAAGGTTATTCTCCGGAAAGCTGGCAGGCATTT
CGTACCGCACTGGCTGCTGCAACCGGCACCCTGGATGATGCAGCAGCATCTGATGAAGC
ACTGCATGATGCACGTCTGGCGCTGCAGGGTGCAGTTGATGCACTGGAAGAACCGGCAG
ATGTTGTTCTGGTTGAAGTTGAGTTTCTCCGCGTTGTCTGGCAGGTAAACCGTATGTT
GCCGTTCGTGCAGTTAATGTTTCTGATGCAGCCGTTGATGTTGAACTGGCAAGCTCTCT
GGGCACCCGTAGCTTTGTTGGTGTGGCACCGGGTGCGAGCGCATATCAGAGCTTTGCAG
CCCGTAGCGCAACCGGTGATCTGGATGTTACCGTGACCGCAACCGGTGCAGATGGTACT
CAGACCGTTGAACAGGTTGTGACCGTTCCGAGCTGTAGCTAATAA
```

FIGURE 4 -1

DsbA-6xHis-CcMan4(107bp - 5494bp, direct) 5388bp from
pLSAHCcMan4
```
 ATGAAAAAGATTTGGCTGGCGCTGGCTGGTTTAGTTTTAGCGTTTAGCGCATCGGCCGG
 CCATCACCATCATCACCACGTGGGGCCCGGCTCGGACGAAGTGGATGCAGAACCGGGTG
 ATTTTAGCAGCAGCTTTGAATCTGGCGATCCGGCAGCACTGCCGACCACCGTTGCAGAA
 CGTGATGGTGCACCGTGGCAGGCAAATGTTGGTAGCTTTACCGCAGGTCTGCCTGGTAG
 CGTTCTGGGTCAGCTGAAAGGTGTTACCGCAAGCGCACAGAATCTGCCGAATGAAGGTG
 CAGCAAATCTGGCAGATGGTAGCAGCGGCACCAAATGGCTGGCATTTGCAAGCACCGGT
 TGGGTTCGTTATGAATTTGCAGAACCGGTTAGCTTTGTTGCATATACCATGACCAGCGG
 TGATGATGCCGCAGGTCGTGATCCGAAAACCTGGACCGTTGAAGGTAGCAATGATGGTT
 CTACCTGGGCAGCACTGGATCGTCGTACCGATGAAGATTTTCCGAATCGTCAGCAGACC
 CGTACCTTTGAACTGGAAGCACCGACCGCAGCATATACCTATCTGCGTCTGAATGTTAC
 CGCAAATAGCGGTGATAGCATTGTTCAGCTGGCAGGTTGGGATCTGAGCGCAGATCTGT
 CTGCAGGTCCGAGCGCAGCACCGATGACCACCAAAGTTGGCACCGGTCCGCGTGTTAGC
 TTTACCAATAAAGCCGGTGTTGGTTTAGCGGTCTGCATAGCCTGCGTTATGATGGTAG
 CCATCTGGCCGATGGTGAAACCTATGCAACCAATGTGCTGTATGATGATGTTGATGTTG
 TGGTTGGTGAAGATACCCGTCTGAGCTATACCATTTTCCGGAACTGCTGGATGATCTG
 CAGTATCCGAGCACCTATGCAGCAGTTGATGTTCTGTTTACCGATGGCACCTATCTGAG
 CGATCTGGGTGCACGTGATGCACATGAAACCGTTGCAACCGCACAGGCACAGGGTGAAG
 GTAAAATTCTGTATGCCGATCAGTGGAATAGCGTTCGTGTTGATCTGGGTGATGTTGCA
 GAAGGTAAAACCGTTGATCAGGTTCTGCTGGGTTATGATAATCCGGGTGGTCATGCAGG
 CACCAAATTTGCAGGTTGGCTGGATGATGTTGAAATTACCGCAGAACCGGCAACCATTG
 ATGGTAGCTCACTGGCAAATTATGTTGATACCCGTCGTGGCACCCTGGCAAGCGGTAGC
 TTTAGCCGTGGTAATAATATTCCGGCAACCGCAACCCCGAATGGTTTTAATTTTTGGAC
 CCCGTATACCAATGCAAGCAGCCAGAGCTGGCTGTATGAATATCATAAAGCCAATAATG
 CGAATAATAAACCGGTTCTGCAGGGTTTTGGTATTAGCCATGAACCGAGCCCGTGGATG
 GGTGATCGTAATCAGCTGACCTTTCTGCCGAGCACCGCAAGCGGTACACCGGATGCAAC
 CCTGAGCACCCGTGGTCTGGAATTTGATCATGCAGATGAAACCGCACGTCCGGATTATT
 ATGGTGTGACCTTTACCAATGGTAGCGCAATTGAAGCAACCCCGACCGATCATGGTGCA
 GTTCTGCGTTTTAGCTATCCGGGTGCAAAAGGTCATGTTCTGGTGGATAAAGTTGATGG
 TAGCAGTAAACTGACCTATGATCAGGCAACCGGCACCATTAGCGGTTGGGTTGAAAATG
 GTAGCGGTCTGAGCGTTGGTCGTACCCGTATGTTTGTTGCAGGCACCTTTGATCGTAGC
 CCGACCGCAGTTGGCACAGCAGCAGGTAATCGTGCAGATGCACGTTTTGCAACCTTTGA
 AACCAGCAGCGATAAAACCGTGGAACTGCGTGTTGCAACCAGCTTTATTAGCCTGGATC
 AGGCACGTAAAATCTGGATCTGGAAGTTACCGGTAAAACCTTTACCGAAGTTAAAGCA
 GCAGCAGCACAGGCATGGAATGATCGTCTGGGTGTTATTGAAGTTGAAGGTGCAAGCGA
 AGATCAGCTGGTTACCCTGTATAGCAATCTGTATCGCCTGAATCTGTATCCGAATAGCC
 AGTTTGAAAATACCGGCACCGCACAGGAACCGGTTTATCGTTACGCATCTCCGGTTAGC
 GCAACCACCGGTAGCGCAACCGATACCCAGACCAATGCCAAAATTGTGGATGGCAAAAT
 TTATGTGAATAATGGCTTTTGGGATACCTATCGTACCGCATGGCCTGCATATAGCCTGC
 TGTATCCGGAACTGGCAGCAGAACTGGTTGATGGTTTTGTTCAGCAGTATCGTGATGGT
 GGTTGGATTGCACGTTGGAGCAGTCCGGGTTATGCAGATCTGATGACCGGTACAAGCTC
 TGATGTTGCATTTGCAGATGCCTATCTGAAAGGTAGCCTGCCGACCGGTACAGCACTGG
 AAGCATATGATGCAGCACTGCGTAATGCAACCGTTGCACCTCCAGCAATGCAGTTGGT
 CGTAAAGGTCTGCAGACAAGCCCGTTTCTGGGTTTTACACCGGAAAGCACCCATGAAAG
```

FIGURE 4-2

```
CGTTAGCTGGGGTCTGGAAGGTCTGGTTAATGATTTTGGCATTGGCAATATGGCTGCAG
CACTGGCAGAAGATCCGGCAACACCGGAAGAACGTCGTGAAACCCTGCGTGAAGAAGC
GCATATTTTCTGGAACGTGCCACCCATTATGTTGAACTGTTTGATCCGGAAGTGGATTT
TTTTGTTCCGCGTCATGAAGATGGTACATGGGCAGTTGATCCGGAAACCTATGATCCGG
AAGCATGGGGTGGTGGTTATACCGAAACCAATGGCTGGAATTTTGCATTTCATGCACCG
CAGGATGGTCAGGGTCTGGCAAATCTGTATGGTGGTAAACAGGGTCTGGAAGATAAACT
GGATGAATTTTTTAGCACACCGGAAAAGGTGCAGGTAATGGTGGTATTCATGAACAGC
GTGAAGCACGTGATGTTCGTATGGGTCAGTGGGGTATGAGCAATCAGGTTAGCCATCAT
ATTCCGTGGCTGTATGATGCAGCCGGTGCTCCGAGCAAAGCACAGGAAAAAGTTCGCGA
AGTTACCCGTCGTCTGTTTGTTGGTAGCGAAATTGGTCAGGGTTATCCGGGTGATGAAG
ATAATGGTGAAATGTCCTCCTGGTGGATTTTTGCAAGCCTGGGTTTTTATCCGCTGCAG
GTTGGTAGCGATCAGTATGCAGTTGGTTCTCCGCTGTTTGATAAAGCAACCGTTCATCT
GCCGGATGGTGATCTGGTTGTTAATGCCGAAAATAATAGCGTGGATAATGTGTATGTTC
AGAGCCTGGCAGTTGATGGTGAAGCACGTACCAGCACCAGCCTGAGCCAGGCAGATCTG
AGCGGTGGCACCACCCTGGATTTTGTTATGGGTCCGGAACCGAGCGATTGGGGCACCGG
TGAAGATGATGCACCTCCGTCACTGACCGAAGGTGATGAACCTCCGACACCGGTTCAGG
ATGCAACCACCGCAGGCCTGGGCACCACCACCGTTGCCGATGGTGATGCCACCACCTCT
GCAGCAGCCCTGACCGATAATACCAGCGGCACCCGTACCACCTTTGCAACCACCACCCC
GAGCATTACATGGGCAGGTAATGGCATTCGTCCGACCGTTGGTAGCTATACCCTGACCT
CTGGTGCAAGCGGCACCGCAAGCCCGTCTGCATGGACCCTGGAAGGTTCTGATGATGGC
GAAACCTGGACCACACTGGATGAACGTAGCGGTGAACAGTTTCGTTGGGCACTGCAGAC
CCGTCCGTTTACCGTTGCCGAACCGACCGCATTTGCACGTTATCGTGTTACCGTTACCG
CAACCAGCGGTTCTGGTGCACTGAGCCTGGCAGAAGTTGAACTGCTGGCAGATCCGAAA
GAAAGCGGTGCAGAAGAACTGACCCTGTCTGCAGCACCGGATCGTGATGGCGTTACCGG
TCGTGAAGTTAGCGGTTCTTTTGCAACCCTGACCGGTGTTGAAGGTGATGTTGCCGCAC
TGGATGTTCAGGTTGCATTTGGTGATGGTAGCGAACCGGTTGCAGGTACACTGCGTGCC
GGTGCATTTGGTGGTTATGCAGTTGATGCAGCACATACCTGGACCGCACCGGGTGTTTA
TCCGGTTACCGTGACCGTTAGCGGTGAAGGTATTGAAACCGTTAGCGCAAGCAGCTATG
TTAGCGTTAGCCTGCTGCGTGAAGGTTCTCTGCTGGCAGCATATGATAATGTGTGCATT
GGTGATGCAGGTACAACCGTTGGTTCTTGTGATGGTCAGGGCGTTTTTTTTGATCGTGC
ACAGCTGGCAGCAAAAGGTTTTGTGCAGGGTGAACGTGCAACCGTTCCGGGTACAGATC
TGGCATTTGATGTTCCGGCAGTTCCGGCTGGTCAGCCTGATAATGCAACCGGTGATGGT
CAGACCATTGAACTGGATGTTCCGGCTGATGCAGAACAGCTGAGCGTTATTGGCACCGG
CACCGAAAAAATCAGCAGGCAACCGGTACACTGACCTTTGATGATGGTTCTACCCAGC
CGATTGATCTGAGCTTTGGTGATTGGAGCGGTGCAGCACGTAATCCGGTGTTTGGTAAT
ATTCCGGTTGCAGTTACCGATAGCCGTCTGCGTGGTGGTTCTCCGCAGACCGGTACACC
GGCAGCATTTTTGCCACCGCACCGATTACCCTGCCGGAAGGTAAACGTCCGGTTAGCC
TGACCCTGCCGGATCAGCCTGGTGAACTGAGCCGTGATGGTCGTATTCATGTTGTTGCA
GTTGCACATGATGGCACCTTTGCAGAACATCCTGCACTGGAAGTGACCGCAGCAGAAGG
TGTTACCCTGGCAGTTGGTCAGACCTCAGATGTTGCACTGGCACAGGTTGCCGGTGGTC
GTGAAGGTGCAGATCTGCGTGCCGCAGTTACCTGGGTGATGGTTCTGATGTGGCAGCC
GGTGCCGTTACCGATGGTAGCGTTAGCGGTAGCCATGCATATACCGCAGCAGGCACCTA
TACCGCATATGTTGTTGTGGATGATGGTTGGACCAGCCAGGTTGTTGAAGTTCCGGTGA
CCGTTACAGAAGCCGAACCGGCACTGGCCGTTGATGTCACCGTTAGCACCCGTTGCCTG
GCAGGTAAAGCATATGTTGCAGTGCGTGCAGAAAATGGTGAAGATGTTCCGCTGGCAAT
TCGTCTGGTTACCCCGTTTGGCACCAAAGAAGTTGCAGCAGTTGCTCCGGGAGCCAATG
CATATCAGAGCTTTGCAACCCGTGTTACCGCAGTTGAAGCAGGCACCGTTACCGTTGAA
```

FIGURE 4-3

GCCACCCGTGGCACCGGTGATGAAGAAGTTACCGCCAGCATTCAGGCAGATTATGCAGC
CGTTACCTGCGGTTAATAA

FIGURE 5
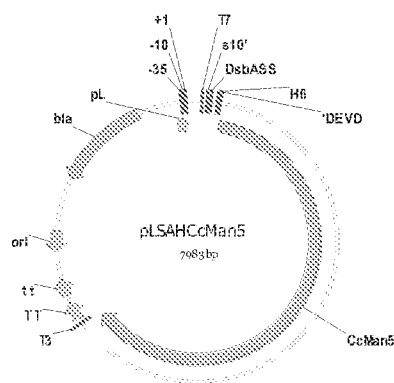
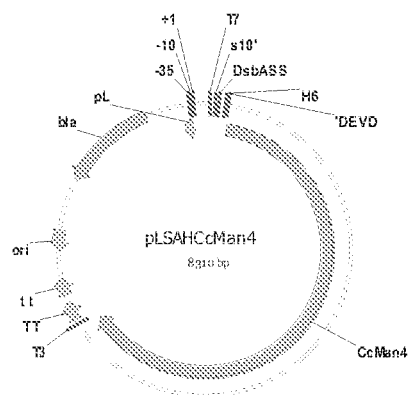

FIGURE 15

```
  1 mhlpslsls1 talaiaspsa ayphfgssqp vlhsssdttq sradaikaaf shawdgylqy
 61 afphdelhpv sngygdsrng wgasavdals tavimrnati vnqildhvgk idysktnttv
121 slfettiryl ggmlsgydll kgpvsdlvqn sskidvlltq sknladvlkf afdtpsgvpy
181 nnlnitsggn dgaktnglav tgtlalewtr lsdltgdtty adlsqkaesy llnpqpksae
241 pfpglvgsni nisngqftda qvswnggdds yyeylikmyv ydpkrfglyk drwvaaaqst
301 mqhlashpss rpdltflasy nngtlqlssq hltcfdggsf llggtvlnrt dfinfgldlv
361 sgchdtynst ltgigpesfs wdtsdipssq qslyekagfy itsgayilrp eviesfyyaw
421 rvtgqetyrd wiwsafsavn dycrtssgfs gltdvnaang gsrydnqesf lfaevmkysy
481 mafaedaawq vqpgsgnqfv fnteahpvrv sst
``` under development. The biological activity of many of these biopharmaceuticals is dependent on their post-translational modification (e.g., phosphorylation or glycosylation). A yeast-based expression system combines the ease of genetic manipulation and fermentation of a microbial organism with the capability to secrete and to modify proteins. However, recombinant glycoproteins produced in yeast cells exhibit mainly heterogeneous high-mannose and hyper-mannose glycan structures, which can be detrimental to protein function, downstream processing, and subsequent therapeutic use, particularly where glycosylation plays a biologically significant role.

SEQUENCE LISTING

```
<160> NUMBER OF SEQ ID NOS: 5

<210> SEQ ID NO 1
<211> LENGTH: 2743
<212> TYPE: DNA
<213> ORGANISM: Artificial Sequence
<220> FEATURE:
<223> OTHER INFORMATION: Yarrowia codon optimized sequence encoding
      alpha glucosidase

<400> SEQUENCE: 1
atgaagcttt ccaccatcct cttcacagcc tgcgctaccc tggctgccgc ccagcaggga      60
gcctctcgac ccgaccccg  agatgcccag gctcaccccg gacgacctcg agctgtgccc     120
acccagtgtg acgtgccccc caactctcga ttcgactgtg cccccgacaa ggccatcacc     180
caggagcagt gcgaggcccg aggctgttgt tacatccccg ctaagcaggg cctgcagggc     240
gctcagatgg gccagccctg tgtttcttc  ccccctctt  acccctccta caagctggag     300
```

```
aacctgtcct cttcggagat gggctacacc gccaccctga cccgaaccac ccccacctttt    360 ttccccaagg acatcctgac cctgcgactg gacgtgatga tggagaccga gaaccgactg    420
cacttcacca tcaaggaccc cgccaaccga cgatacgagg tgcccctgga gacccccac    480 gtgcactctc gagccccttc ccccctgtac tctgtggagt tctctgagga gcccttcggc    540
gtgatcgtgc gacgacagct ggacggccga gtgctgctga acaccaccgt ggcccccctg    600
ttcttcgccg accagttcct gcagctgtct acctctctgc cctctcagta catcaccggc    660
ctggccgagc acctgtcccc cctgatgctg tccacctctt ggactcgaat caccctgtgg    720
aaccgagacc tggcccccac ccccggtgcc aacctgtacg gctctcaccc cttctacctg    780
gccctggagg acggcggctc tgcccacggc gtgtttctgc tgaactctaa cgccatggac    840
gtggtgctgc agccctctcc cgccctgtct tggcgatcta ccggcggcat cctggacgtg    900
tacatcttcc tgggccctga gcccaagtct gtggtccagc agtacctgga cgtggtcgga    960
taccccttca tgcccccta ctggggcctg gcttccacc tgtgtcgatg gggctactct   1020
tctaccgcca tcacccgaca ggtggtggag aacatgaccc gagcccactt ccccctggac   1080
gtgcaatgga acgacctgga ctacatggac tctcgacgag acttcacctt caacaaggac   1140
ggcttccgag acttccccgc catggtccag gagctgcacc agggaggacg acgatacatg   1200
atgatcgtgg accccgccat ctcttcttcc ggacccgccg gatcttaccg accctacgac   1260
gagggcctgc gacgaggcgt gttcatcacc aacgagaccg gccagcccct gatcggcaag   1320
gtgtggcccg gctctaccgc cttccccgac ttcaccaacc ccaccgccct ggcttggtgg   1380
gaggacatgg tggccgagtt ccacgaccag gtgcccttcg acggcatgtg gatcgacatg   1440
aacgagccct ctaacttcat ccgaggctct gaggacggct gtcccaacaa cgagctggag   1500
aaccccccct acgtgcccgg cgtggtgggc ggaaccctgc aggccgccac catctgtgcc   1560
tcttcgcacc agtttctgtc tacccactac aacctgcaca acctgtacgg actgaccgag   1620
gccattgcct ctcaccgagc cctggtgaag gcccgaggca cccgaccctt cgtgatctct   1680
cgatctacct tcgccggcca cggccgatac gccggacact ggaccggcga tgtgtggtcc   1740
tcttgggagc agctggcctc ttctgtgccc gagatcctgc agttcaacct gctgggcgtg   1800
cccctggtgg gcgccgacgt gtgtggcttc ctgggcaaca cctctgagga gctgtgtgtt   1860
cgatggaccc agctcggcgc cttctaccct ttcatgcgaa accacaactc cctgctgtct   1920
ctgccccagg agccctactc gttctctgag cccgctcagc aggccatgcg aaaggctctg   1980
accctgcgat acgccctgct gccccacctg tacacccctgt tccaccaggc ccacgtggct   2040
ggagagaccg tggcccgacc cctgttcctg gagttcccta aggactcttc tacctggacc   2100
gtggaccatc agctgctgtg gggcgaggcc ctcctgatca cccccgtgct gcaggccggc   2160
aaggctgagg tgaccggcta cttccctctg ggcacctggt acgacctgca gacgtgcct   2220 gtggaggccc tgggatctct gcccctcct cccgccgctc ccgagagcc cgccatccac   2280 tctgagggcc agtgggtgac cctgcccgct ccccctggaca ccatcaacgt gcacctgcga   2340
gccggctaca tcatccctct gcagggaccc ggcctgacca ccaccgagtc tcgacagcag   2400
cccatgcccc tggccgtggc tctgaccaag ggcgagagg cccgaggcga gctgttctgg   2460
gacgatggcg agtctctgga ggtgctggag cgaggcgcct acacccaggt gatctttctg   2520
gcccgaaaca caccatcgt gaacgagctg gtgcgagtga cctctgaggg cgctggtctg   2580
cagctccaga aggtgaccgt cctgggcgtg gccaccgctc cccagcaggt cctgtctaac   2640
ggcgtgcccg tgtctaactt cacctactct cccgacacca aggtgctgga catctgtgtg   2700
```
tctctgctga tgggcgagca gttcctggtg tcttggtgtt aac                          2743

<210> SEQ ID NO 2
<211> LENGTH: 913
<212> TYPE: PRT
<213> ORGANISM: Artificial Sequence
<220> FEATURE:
<223> OTHER INFORMATION: Fusion of Yarrowia LIP2 signal sequence to
      human alpha glucosidase

<400> SEQUENCE: 2

```
Met Lys Leu Ser Thr Ile Leu Phe Thr Ala Cys Ala Thr Leu Ala Ala
 1               5                  10                  15

Ala Gln Gln Gly Ala Ser Arg Pro Gly Pro Arg Asp Ala Gln Ala His
            20                  25                  30

Pro Gly Arg Pro Arg Ala Val Pro Thr Gln Cys Asp Val Pro Pro Asn
        35                  40                  45

Ser Arg Phe Asp Cys Ala Pro Asp Lys Ala Ile Thr Gln Glu Gln Cys
    50                  55                  60

Glu Ala Arg Gly Cys Cys Tyr Ile Pro Ala Lys Gln Gly Leu Gln Gly
65                  70                  75                  80

Ala Gln Met Gly Gln Pro Trp Cys Phe Phe Pro Pro Ser Tyr Pro Ser
                85                  90                  95

Tyr Lys Leu Glu Asn Leu Ser Ser Ser Glu Met Gly Tyr Thr Ala Thr
            100                 105                 110

Leu Thr Arg Thr Thr Pro Thr Phe Phe Pro Lys Asp Ile Leu Thr Leu
        115                 120                 125

Arg Leu Asp Val Met Met Glu Thr Glu Asn Arg Leu His Phe Thr Ile
    130                 135                 140

Lys Asp Pro Ala Asn Arg Arg Tyr Glu Val Pro Leu Glu Thr Pro His
145                 150                 155                 160

Val His Ser Arg Ala Pro Ser Pro Leu Tyr Ser Val Glu Phe Ser Glu
                165                 170                 175

Glu Pro Phe Gly Val Ile Val Arg Arg Gln Leu Asp Gly Arg Val Leu
            180                 185                 190

Leu Asn Thr Thr Val Ala Pro Leu Phe Phe Ala Asp Gln Phe Leu Gln
        195                 200                 205

Leu Ser Thr Ser Leu Pro Ser Gln Tyr Ile Thr Gly Leu Ala Glu His
    210                 215                 220

Leu Ser Pro Leu Met Leu Ser Thr Ser Trp Thr Arg Ile Thr Leu Trp
225                 230                 235                 240

Asn Arg Asp Leu Ala Pro Thr Pro Gly Ala Asn Leu Tyr Gly Ser His
                245                 250                 255

Pro Phe Tyr Leu Ala Leu Glu Asp Gly Gly Ser Ala His Gly Val Phe
            260                 265                 270

Leu Leu Asn Ser Asn Ala Met Asp Val Val Leu Gln Pro Ser Pro Ala
        275                 280                 285

Leu Ser Trp Arg Ser Thr Gly Gly Ile Leu Asp Val Tyr Ile Phe Leu
    290                 295                 300

Gly Pro Glu Pro Lys Ser Val Val Gln Gln Tyr Leu Asp Val Val Gly
305                 310                 315                 320

Tyr Pro Phe Met Pro Pro Tyr Trp Gly Leu Gly Phe His Leu Cys Arg
                325                 330                 335

Trp Gly Tyr Ser Ser Thr Ala Ile Thr Arg Gln Val Val Glu Asn Met
            340                 345                 350
```

-continued

Thr Arg Ala His Phe Pro Leu Asp Val Gln Trp Asn Asp Leu Asp Tyr
        355                 360                 365

Met Asp Ser Arg Arg Asp Phe Thr Phe Asn Lys Asp Gly Phe Arg Asp
    370                 375                 380

Phe Pro Ala Met Val Gln Glu Leu His Gln Gly Gly Arg Arg Tyr Met
385                 390                 395                 400

Met Ile Val Asp Pro Ala Ile Ser Ser Gly Pro Ala Gly Ser Tyr
                405                 410                 415

Arg Pro Tyr Asp Glu Gly Leu Arg Arg Gly Val Phe Ile Thr Asn Glu
                420                 425                 430

Thr Gly Gln Pro Leu Ile Gly Lys Val Trp Pro Gly Ser Thr Ala Phe
        435                 440                 445

Pro Asp Phe Thr Asn Pro Thr Ala Leu Ala Trp Trp Glu Asp Met Val
    450                 455                 460

Ala Glu Phe His Asp Gln Val Pro Phe Asp Gly Met Trp Ile Asp Met
465                 470                 475                 480

Asn Glu Pro Ser Asn Phe Ile Arg Gly Ser Glu Asp Gly Cys Pro Asn
                485                 490                 495

Asn Glu Leu Glu Asn Pro Tyr Val Pro Gly Val Val Gly Gly Thr
            500                 505                 510

Leu Gln Ala Ala Thr Ile Cys Ala Ser Ser His Gln Phe Leu Ser Thr
        515                 520                 525

His Tyr Asn Leu His Asn Leu Tyr Gly Leu Thr Glu Ala Ile Ala Ser
    530                 535                 540

His Arg Ala Leu Val Lys Ala Arg Gly Thr Arg Pro Phe Val Ile Ser
545                 550                 555                 560

Arg Ser Thr Phe Ala Gly His Gly Arg Tyr Ala Gly His Trp Thr Gly
                565                 570                 575

Asp Val Trp Ser Ser Trp Glu Gln Leu Ala Ser Ser Val Pro Glu Ile
            580                 585                 590

Leu Gln Phe Asn Leu Leu Gly Val Pro Leu Val Gly Ala Asp Val Cys
        595                 600                 605

Gly Phe Leu Gly Asn Thr Ser Glu Glu Leu Cys Val Arg Trp Thr Gln
    610                 615                 620

Leu Gly Ala Phe Tyr Pro Phe Met Arg Asn His Asn Ser Leu Leu Ser
625                 630                 635                 640

Leu Pro Gln Glu Pro Tyr Ser Phe Ser Glu Pro Ala Gln Gln Ala Met
                645                 650                 655

Arg Lys Ala Leu Thr Leu Arg Tyr Ala Leu Leu Pro His Leu Tyr Thr
            660                 665                 670

Leu Phe His Gln Ala His Val Ala Gly Glu Thr Val Ala Arg Pro Leu
        675                 680                 685

Phe Leu Glu Phe Pro Lys Asp Ser Ser Thr Trp Thr Val Asp His Gln
    690                 695                 700

Leu Leu Trp Gly Glu Ala Leu Leu Ile Thr Pro Val Leu Gln Ala Gly
705                 710                 715                 720

Lys Ala Glu Val Thr Gly Tyr Phe Pro Leu Gly Thr Trp Tyr Asp Leu
                725                 730                 735

Gln Thr Val Pro Val Glu Ala Leu Gly Ser Leu Pro Pro Pro Ala
            740                 745                 750

Ala Pro Arg Glu Pro Ala Ile His Ser Glu Gly Gln Trp Val Thr Leu
        755                 760                 765

| | | | | | | | | | | | |
|---|---|---|---|---|---|---|---|---|---|---|---|
|Pro|Ala|Pro|Leu|Asp|Thr|Ile|Asn|Val|His|Leu|Arg|Ala|Gly|Tyr|Ile|
|770| | | |775| | | |780| | | | | | | |

Ile Pro Leu Gln Gly Pro Gly Leu Thr Thr Thr Glu Ser Arg Gln Gln
785                 790                 795                 800

Pro Met Ala Leu Ala Val Ala Leu Thr Lys Gly Gly Glu Ala Arg Gly
                805                 810                 815

Glu Leu Phe Trp Asp Asp Gly Glu Ser Leu Glu Val Leu Glu Arg Gly
            820                 825                 830

Ala Tyr Thr Gln Val Ile Phe Leu Ala Arg Asn Asn Thr Ile Val Asn
        835                 840                 845

Glu Leu Val Arg Val Thr Ser Glu Gly Ala Gly Leu Gln Leu Gln Lys
    850                 855                 860

Val Thr Val Leu Gly Val Ala Thr Ala Pro Gln Gln Val Leu Ser Asn
865                 870                 875                 880

Gly Val Pro Val Ser Asn Phe Thr Tyr Ser Pro Asp Thr Lys Val Leu
                885                 890                 895

Asp Ile Cys Val Ser Leu Leu Met Gly Glu Gln Phe Leu Val Ser Trp
            900                 905                 910

Cys

<210> SEQ ID NO 3
<211> LENGTH: 5060
<212> TYPE: DNA
<213> ORGANISM: Artificial Sequence
<220> FEATURE:
<223> OTHER INFORMATION: Nucleotide sequence encoding fusion of DsbA
      signal sequence to Cellulosimicrobium cellulans
      mannosidase 5

<400> SEQUENCE: 3

```
atgaaaaaga tttggctggc gctggctggt ttagttttag cgtttagcgc atcggccggc      60
catcaccatc atcaccacgt ggggcccggc tcggacgaag tggatgcacc ggaacctccg     120
agcgcagatt atgcaagcct ggttgatgtt tttgttggca ccgaaggtga ttttggtaat     180
gatatgcctg cagcacaggc accgaatggt ctggcaaaag ttaatccgcg taccacaccg     240
ggtcgtaata taccggtta tgattatgcc cagagcaaaa ttagcggttt tacccatacc     300
aatctggatg tgttggtgg tagcggtggt ggtggtgatc tgctggttgt tccgaccagc     360
ggtagctata ccgcacgtcc gggtacaggc acctatgcac atccgtttag ccatgatgat     420
gaagatgcag tcccgggttt ttatagcgtt ggtctgggta atgttgcagg caccgatggt     480
gcaattaccg gtgctccggg tacaattgaa gcagaagttg cagcagcaac ccgtagcggt     540
gttcatcgtt atgcatttcc ggcaggtagc accccgagcc tggttgttga tctggaaacc     600
aataatacca gccgtcgtag cagcagcgtt caggttgaaa ccgtgcaga tggcaccgtt     660
gaactgagcg gtcaggttac cggctatttt tataatgcag cctataccct gtattatacc     720
gcacgcaccc tgcagcctgc aaccgttcag acctgggtg atgatgatcg tctggttgat     780
gcaaccgcac aggatggtgt tgataccggt gcaattctga cctttgatcc ggcagatgcc     840
ggtgaaattg gtctgcaggt taccctgtct ccggttagcg ttgaacaggc acgtattgat     900
cagcaggttg aactgggtga tctgagcttt gatgcaattc gtgatcgtac ccgtgcagaa     960
tggaatgcaa ccctgggtcg tgttgcaatt gatgcaagca ccgcaaccga tccgaccggt    1020
gaactgcagc gtctgtttta tacccatctg tatcgcatgt ttgcaatgcc gatgaatgca    1080
accagcacca gcggcaccta tcgtggtgtt gatggtgcag ttcatgcagc acagggcttt    1140
```

-continued

| | |
|---|---|
| acctattatg atagctgggc aacctgggat gattttcgca aatttagcgt gattgcctat | 1200 |
| attgatccgg cactgtatcg tgatatggtt cagagcctgg tttacctgtt tgcagatgca | 1260 |
| gaagcaaccg gtacaggcgg tggtctgggt ggttttgttc atagcgttcc gaccgttcgt | 1320 |
| tgggaacgta gcagcgttgt tgttgcagat gcaattgcca aaggctttga tggttttgat | 1380 |
| cgtctggatg aagcatatcc ggcactgcag cgcctggttg gtcagtatag cgcagatgaa | 1440 |
| ctgcgtcgtg gttatgttgc aggtaatccg ggtgcaagcg ttcagcgtgg ttatgatcag | 1500 |
| tatggtctga gcgttattgc cgatgaactg ggtctgaccg aagaagcaga aaccctgcgc | 1560 |
| gaacaggcaa gctggccgat tgaaaaactg accaaaccgg gtgcatggac cgcagcagat | 1620 |
| ggtacacagg ttggtctgct gacaccgcgt gcagccgatg gtagctggca gagcgcagat | 1680 |
| catgccaaat ttgaagcagc aggtctgtat cagggcaccc tgtggcagta tcattggtat | 1740 |
| gatgcctatg atatggatgc actggttgaa gcaatgggtg gtcatgaagc agcccgtctg | 1800 |
| ggtatgcgtc atatgtttgg tgaacatgca ccggatgatg gtaaagcaat gctgcatagc | 1860 |
| aatgccaatg aaattgatct gcaggcaccg tacctgttta attataccgg tgaaccgagc | 1920 |
| ctgacccaga aatgggcacg tgcaatttat accaaagaaa cctggaatcg ctatattgca | 1980 |
| accggtagca gctctgcagt tccgtcaggt ggtggtgaat tacacctcc gctgaaaacc | 2040 |
| aaagtttatc gtctggaccc tcgtggtatg ctgccgacca tggataatga tgcaggtaca | 2100 |
| atgagccacca tgtttgttgc agcagccgtt ggtctgtttc cggttaccgc aggtagcagc | 2160 |
| cagtttcagg ttggtagccc gttttttgat agcaccacca ttacctatga tgatggtagc | 2220 |
| gcatttaccg ttaccgcaga tggtgttagc gaagatgcct tttatgttca gagcgcaacc | 2280 |
| ctggatggtg caacctttgg taatacctgg gttgattatg caaccgttgt tggtggtgca | 2340 |
| gatctggcat tcgtatggg tgaacagccg agcgattggg gcaccgatac cgcaccggca | 2400 |
| tttagcatga gcaccgccac cgatgaaccg gcagaaggtc ctcgcgttag cgcagaaccg | 2460 |
| accaccgtgc agaccggtga tggtggtgca ctggatgcaa ccgttacccct gacactggat | 2520 |
| ggcgcacgtc tggcagcacc ggcaggtaca gatctggtta ccagcggtgc agcaagcgtt | 2580 |
| gttggtctgc cggatggtgt taccgcagca gttaccgttg caagcccgac cgcactgacc | 2640 |
| gttagcctga ccggcaccgc atcagcagat gcacgttttt ttgtgcatct gcgtgatgca | 2700 |
| gcactggccg atggtgttgc agccgcaagc ctgcagggtc agggtgttag cgttcgttct | 2760 |
| ccgctgcgtc tgagcgttgc aagcgcagaa cgtgatgcac tggcagcact ggttgatgat | 2820 |
| gccgttctgg ttcgtcatgg taattatagc agcgttacct ttgatcgttt agcaccgctc | 2880 |
| tgacaaaagc acaggaagca ctgggcgacg aagcagcaac cagcattgca ctgcgttttg | 2940 |
| cagcagatcg tctgggtgca gcagcagatg cactggatct gaccggtggt ggttatcgta | 3000 |
| ccctggaagc agaacagagc gaagcatggt ctggtggtga actgaaaaat gaagccaata | 3060 |
| gcagcagcgg taatctgggt ggtgttcgta gcggtagctg ggttcagtat cgcgatatga | 3120 |
| cctttgaaac cgcagccggt gatacacctc cgcgttttct gaccgttcgt tatgatacca | 3180 |
| gctttgcacc gaccgatacc ccgagcaccg ttcgtgttca tgccggtgat gtttctggtc | 3240 |
| cggttgttgc aaccgttgat ctgaaaggca ccagcgttgg ggtaaatat accgaagtta | 3300 |
| ccgcagaact gggtgatgtt caggccctgg ttgatgccca ggttgttacc tttgaactgc | 3360 |
| tggcaccgag cggtcgtagc tgggttggta attttgattg gtttcgcttt agcgcagaag | 3420 |
| atccggcagc accgggtcag cctggtgaaa gcccgaccgt taccattgaa gccgaagatt | 3480 |
| ggaccgcaag cagcggtcgt ggtctgaaaa agaaaagcag cacctggacc agcggtccgg | 3540 |

```
tgaccaatgt tggtggtaca gcagatggtg attggattgc ctatggtgaa gttgatctgg    3600
gtgaactgcc gctgggcgaa ctgagcgttc attatgtgca taatagcaat cgcagcggta    3660
ataatagcgc actgagcgtt tatctggatg catttgatcc ggctaatccg ggtgaaccgt    3720 tgttaccgt tccgctgccg accaccggta gcagttggac cgcagatggc acagccaccg     3780
ttgttctgcc ggaaaccgtg cagggcaccc atgaagtttt tgttcgtctg agcaccgaac    3840
cgtatgcaga tcatccgtat gttgcaaatc tggatagcct gacctttgca ccgggtggtc    3900
cgaccagcgt tgtggttgaa agcgaagcct ggaccagcaa ttctggtcgt ggcctgaaaa    3960
atgaatcttc tacctggacc tctggtccgg ttacaaatgt gggtggcacc gctgatggcg    4020
attggctggc atatggcgaa attgatctgg gcagcgcagc actggatcag ctgtctgtgc    4080
attatgttca taattctaat cgctctggtc gtaattctgc actgtctgtg tatctggatg    4140
cctttgatcc ggcaaatccg ggtgaaccgt tgtgacagt gccgctggca ataccggta     4200 gctcttggac caccgatggt actgcagttg tggatctgcc gtctaccgtt cgtggtaaac    4260
atcaggtttg ggttcgtctg tctaccgaag catatgccga tcatccgtat gtggccaatc    4320
tggattctat gcgctttttt accgatgcat atgatgttga agttcctccg accgatacag    4380
cagcactggc agccgttgtt gatgcagcag gtacaccgga agcagaaatt gcacgttatg    4440
gtcgtattga tgcccgtgtt tttacccgtg aactggcagc agcacgtagc gttctggccg    4500
atgccggtgc aacacaggca caggcagatg aacgtgctcg tcgtctgggt ctggcaaccg    4560
atcagctggt tccggcagaa cgtcgtcgtc tggaaaatct ggttgccagc gcagaagcac    4620
tgaccgacga aggttattct ccggaaagct ggcaggcatt tcgtaccgca ctggctgctg    4680
caaccggcac cctggatgat gcagcagcat ctgatgaagc actgcatgat gcacgtctgg    4740
cgctgcaggg tgcagttgat gcactggaag aaccggcaga tgttgttctg gttgaagttg    4800
aagtttctcc gcgttgtctg gcaggtaaac cgtatgttgc cgttcgtgca gttaatgttt    4860
ctgatgcagc cgttgatgtt gaactggcaa gctctctggg cacccgtagc tttgttggtg    4920
tggcaccggg tgcgagcgca tatcagagct ttgcagcccg tagcgcaacc ggtgatctgg    4980
atgttaccgt gaccgcaacc ggtgcagatg gtactcagac cgttgaacag gttgtgaccg    5040
ttccgagctg tagctaataa                                                 5060
```

<210> SEQ ID NO 4
<211> LENGTH: 5388
<212> TYPE: DNA
<213> ORGANISM: Artificial Sequence
<220> FEATURE:
<223> OTHER INFORMATION: Nucleotide sequence encoding fusion of DsbA
      signal sequence to Cellulosimicrobium cellulans mannosidase 4

<400> SEQUENCE: 4

```
atgaaaaaga tttggctggc gctggctggt ttagttttag cgtttagcgc atcggccggc     60
catcaccatc atcaccacgt ggggcccggc tcggacgaag tggatgcaga accgggtgat    120
tttagcagca gctttgaatc tggcgatccg gcagcactgc cgaccaccgt tgcagaacgt    180
gatggtgcac cgtggcaggc aaatgttggt agctttaccg caggtctgcc tggtagcgtt    240
ctgggtcagc tgaaaggtgt taccgcaagc gcacagaatc tgccgaatga aggtgcagca    300
aatctggcag atggtagcag cggcaccaaa tggctggcat tgcaagcac cggttgggtt    360 cgttatgaat ttgcagaacc ggttagcttt gttgcatata ccatgaccag cggtgatgat    420
gccgcaggtc gtgatccgaa aacctggacc gttgaaggta gcaatgatgg ttctacctgg    480
```

```
gcagcactgg atcgtcgtac cgatgaagat tttccgaatc gtcagcgac  ccgtaccttt   540 gaactggaag caccgaccgc agcatatacc tatctgcgtc tgaatgttac cgcaaatagc   600
ggtgatagca ttgttcagct ggcaggttgg gatctgagcg cagatctgtc tgcaggtccg   660
agcgcagcac cgatgaccac caaagttggc accggtccgc gtgttagctt taccaataaa   720
gccggtgttg gttttagcgg tctgcatagc ctgcgttatg atggtagcca tctggccgat   780
ggtgaaacct atgcaaccaa tgtgctgtat gatgatgttg atgttgtggt tggtgaagat   840
acccgtctga gctataccat ttttccggaa ctgctggatg atctgcagta tccgagcacc   900
tatgcagcag ttgatgttct gtttaccgat ggcacctatc tgagcgatct gggtgcacgt   960
gatgcacatg aaaccgttgc aaccgcacag gcacagggtg aaggtaaaat tctgtatgcc  1020
gatcagtgga atagcgttcg tgttgatctg ggtgatgttg cagaaggtaa aaccgttgat  1080
caggttctgc tgggttatga taatccgggt ggtcatgcag gcaccaaatt tgcaggttgg  1140
ctggatgatg ttgaaattac cgcagaaccg gcaaccattg atggtagctc actggcaaat  1200
tatgttgata cccgtcgtgg cacctggca agcggtagct ttagccgtgg taataatatt  1260
ccggcaaccg caaccccgaa tggttttaat ttttggaccc cgtataccaa tgcaagcagc  1320
cagagctggc tgtatgaata tcataaagcc aataatgcga ataataaacc ggttctgcag  1380
ggttttggta ttagccatga accgagcccg tggatgggtg atcgtaatca gctgaccttt  1440
ctgccgagca ccgcaagcgg tacaccggat gcaaccctga gcaccgtgg tctggaattt  1500 gatcatgcag atgaaaccgc acgtccggat tattatggtg tgaccttac caatggtagc  1560 gcaattgaag caaccccgac cgatcatggt gcagttctgc gttttagcta tccgggtgca  1620
aaaggtcatg ttctggtgga taaagttgat ggtagcagta aactgaccta tgatcaggca  1680
accggcacca ttagcggttg ggttgaaaat ggtagcggtc tgagcgttgg tcgtacccgt  1740
atgtttgttg caggcacctt tgatcgtagc ccgaccgcag ttggcacagc agcaggtaat  1800
cgtgcagatg cacgttttgc aacctttgaa accagcagcg ataaaaccgt ggaactgcgt  1860
gttgcaacca gctttattag cctggatcag gcacgtaaaa atctggatct ggaagttacc  1920
ggtaaaacct ttaccgaagt taaagcagca gcagcacagg catggaatga tcgtctgggt  1980
gttattgaag ttgaaggtgc aagcgaagat cagctggtta ccctgtatag caatctgtat  2040
cgcctgaatc tgtatccgaa tagccagttt gaaaatccg gcaccgcaca ggaaccggtt  2100
tatcgttacg catctccggt tagcgcaacc accggtagcg caaccgatac ccagaccaat  2160
gccaaaattg tggatggcaa aatttatgtg aataatggct tttgggatac ctatcgtacc  2220
gcatggcctg catatagcct gctgtatccg gaactggcag cagaactggt tgatggtttt  2280
gttcagcagt atcgtgatgg tggttggatt gcacgttgga gcagtccggg ttatgcagat  2340
ctgatgaccg gtacaagctc tgatgttgca tttgcagatg cctatctgaa aggtagcctg  2400
ccgaccggta cagcactgga agcatatgat gcagcactgc gtaatgcaac cgttgcacct  2460
ccgagcaatg cagttggtcg taaaggtctg cagacaagcc cgtttctggg ttttacaccg  2520
gaaagcaccc atgaaagcgt tagctggggt ctggaaggtc tggttaatga ttttggcatt  2580
ggcaatatgg ctgcagcact ggcagaagat ccggcaacac cggaagaacg tcgtgaaacc  2640
ctgcgtgaag aaagcgcata tttctggaa cgtgccaccc attatgttga actgtttgat  2700
ccggaagtgg atttttttgt tccgcgtcat gaagatggta catgggcagt tgatccggaa  2760
acctatgatc cggaagcatg gggtggtggt tataccgaaa ccaatggctg gaattttgca  2820
```

```
tttcatgcac cgcaggatgg tcagggtctg gcaaatctgt atggtggtaa acagggtctg    2880
gaagataaac tggatgaatt ttttagcaca ccggaaaaag gtgcaggtaa tggtggtatt    2940
catgaacagc gtgaagcacg tgatgttcgt atgggtcagt ggggtatgag caatcaggtt    3000
agccatcata ttccgtggct gtatgatgca gccggtgctc cgagcaaagc acaggaaaaa    3060
gttcgcgaag ttacccgtcg tctgtttgtt ggtagcgaaa ttggtcaggg ttatccgggt    3120
gatgaagata tggtgaaat gtcctcctgg tggattttg caagcctggg ttttatccg     3180 ctgcaggttg gtagcgatca gtatgcagtt ggttctccgc tgtttgataa agcaaccgtt    3240
catctgccgg atggtgatct ggttgttaat gccgaaaata tagcgtgga taatgtgtat    3300 gttcagagcc tggcagttga tggtgaagca cgtaccagca ccagcctgag ccaggcagat    3360
ctgagcggtg gcaccaccct ggattttgtt atgggtccgg aaccgagcga ttggggcacc    3420
ggtgaagatg atgcacctcc gtcactgacc gaaggtgatg aacctccgac accggttcag    3480
gatgcaacca ccgcaggcct gggcaccacc accgttgccg atggtgatgc caccacctct    3540
gcagcagccc tgaccgataa taccagcggc acccgtacca cctttgcaac caccaccccg    3600
agcattacat gggcaggtaa tggcattcgt ccgaccgttg gtagctatac cctgacctct    3660
ggtgcaagcg gcaccgcaag cccgtctgca tggaccctgg aaggttctga tgatggcgaa    3720
acctggacca cactggatga acgtagcggt gaacagtttc gttgggcact gcagacccgt    3780
ccgtttaccg ttgccgaacc gaccgcattt gcacgttatc gtgttaccgt taccgcaacc    3840
agcggttctg gtgcactgag cctggcagaa gttgaactgc tggcagatcc gaaagaaagc    3900
ggtgcagaag aactgaccct gtctgcagca ccggatcgtg atggcgttac cggtcgtgaa    3960
gttagcggtt cttttgcaac cctgaccggt gttgaaggtg atgttgccgc actggatgtt    4020
caggttgcat ttggtgatgg tagcgaaccg gttgcaggta cactgcgtgc cggtgcattt    4080
ggtggttatg cagttgatgc agcacatacc tggaccgcac cgggtgttta tccggttacc    4140
gtgaccgtta gcgtgaaggg tattgaaacc gttagcgcaa gcagctatgt tagcgttagc    4200
ctgctgcgtg aaggttctct gctggcagca tatgataatg tgtgcattgg tgatgcaggt    4260
acaaccgttg gttcttgtga tggtcaggggc gttttttttg atcgtgcaca gctggcagca    4320
aaaggttttg tgcagggtga acgtgcaacc gttccgggta cagatctggc atttgatgtt    4380
ccggcagttc cggctggtca gcctgataat gcaaccggtg atggtcagac cattgaactg    4440
gatgttccgg ctgatgcaga acagctgagc gttattggca ccggcaccga aaaaaatcag    4500
caggcaaccg gtacactgac cttttgatgat ggttctaccc agccgattga tctgagctttt    4560 ggtgattgga gcggtgcagc acgtaatccg gtgtttggta atattccggt tgcagttacc    4620
gatagccgtc tgcgtggtgg ttctccgcag accggtacac cggcagcatt ttttgccacc    4680
gcaccgatta ccctgccgga aggtaaacgt ccggttagcc tgaccctgcc ggatcagcct    4740
ggtgaactga gccgtgatgg tcgtattcat gttgttgcag ttgcacatga tggcacctttt    4800 gcagaacatc ctgcactgga agtgaccgca gcagaaggtg ttaccctggc agttggtcag    4860
acctcagatg ttgcactggc acaggttgcc ggtggtcgtg aaggtgcaga tctgcgtgcc    4920
gcagttacct ggggtgatgg ttctgatgtg cagccggtg ccgttaccga tggtagcgtt    4980
agcggtagcc atgcatatac cgcagcaggc acctataccg catatgttgt tgtggatgat    5040
ggttggacca gccaggttgt tgaagttccg gtgaccgtta cagaagccga accggcactg    5100
gccgttgatg tcaccgttag cacccgttgc ctggcaggta aagcatatgt tgcagtgcgt    5160
gcagaaaatg gtgaagatgt tccgctggca attcgtctgg ttaccccgtt tggcaccaaa    5220
```

-continued

```
gaagttgcag cagttgctcc gggagccaat gcatatcaga gctttgcaac ccgtgttacc    5280
gcagttgaag caggcaccgt taccgttgaa gccacccgtg gcaccggtga tgaagaagtt    5340
accgccagca ttcaggcaga ttatgcagcc gttacctgcg gttaataa                 5388
```

<210> SEQ ID NO 5
<211> LENGTH: 513
<212> TYPE: PRT
<213> ORGANISM: Aspergillus saitoi

<400> SEQUENCE: 5

```
Met His Leu Pro Ser Leu Ser Leu Ser Leu Thr Ala Leu Ala Ile Ala
 1               5                  10                  15

Ser Pro Ser Ala Ala Tyr Pro His Phe Gly Ser Ser Gln Pro Val Leu
            20                  25                  30

His Ser Ser Asp Thr Thr Gln Ser Arg Ala Asp Ala Ile Lys Ala
        35                  40                  45

Ala Phe Ser His Ala Trp Asp Gly Tyr Leu Gln Tyr Ala Phe Pro His
    50                  55                  60

Asp Glu Leu His Pro Val Ser Asn Gly Tyr Gly Asp Ser Arg Asn Gly
65                  70                  75                  80

Trp Gly Ala Ser Ala Val Asp Ala Leu Ser Thr Ala Val Ile Met Arg
                85                  90                  95

Asn Ala Thr Ile Val Asn Gln Ile Leu Asp His Val Gly Lys Ile Asp
            100                 105                 110

Tyr Ser Lys Thr Asn Thr Thr Val Ser Leu Phe Glu Thr Thr Ile Arg
        115                 120                 125

Tyr Leu Gly Gly Met Leu Ser Gly Tyr Asp Leu Leu Lys Gly Pro Val
    130                 135                 140

Ser Asp Leu Val Gln Asn Ser Ser Lys Ile Asp Val Leu Leu Thr Gln
145                 150                 155                 160

Ser Lys Asn Leu Ala Asp Val Leu Lys Phe Ala Phe Asp Thr Pro Ser
                165                 170                 175

Gly Val Pro Tyr Asn Asn Leu Asn Ile Thr Ser Gly Gly Asn Asp Gly
            180                 185                 190

Ala Lys Thr Asn Gly Leu Ala Val Thr Gly Thr Leu Ala Leu Glu Trp
        195                 200                 205

Thr Arg Leu Ser Asp Leu Thr Gly Asp Thr Thr Tyr Ala Asp Leu Ser
    210                 215                 220

Gln Lys Ala Glu Ser Tyr Leu Leu Asn Pro Gln Pro Lys Ser Ala Glu
225                 230                 235                 240

Pro Phe Pro Gly Leu Val Gly Ser Asn Ile Asn Ile Ser Asn Gly Gln
                245                 250                 255

Phe Thr Asp Ala Gln Val Ser Trp Asn Gly Gly Asp Asp Ser Tyr Tyr
            260                 265                 270

Glu Tyr Leu Ile Lys Met Tyr Val Tyr Asp Pro Lys Arg Phe Gly Leu
        275                 280                 285

Tyr Lys Asp Arg Trp Val Ala Ala Gln Ser Thr Met Gln His Leu
    290                 295                 300

Ala Ser His Pro Ser Ser Arg Pro Asp Leu Thr Phe Leu Ala Ser Tyr
305                 310                 315                 320

Asn Asn Gly Thr Leu Gly Leu Ser Ser Gln His Leu Thr Cys Phe Asp
                325                 330                 335

Gly Gly Ser Phe Leu Leu Gly Gly Thr Val Leu Asn Arg Thr Asp Phe
```

-continued

```
            340                 345                 350
Ile Asn Phe Gly Leu Asp Leu Val Ser Gly Cys His Asp Thr Tyr Asn
            355                 360                 365

Ser Thr Leu Thr Gly Ile Gly Pro Glu Ser Phe Ser Trp Asp Thr Ser
            370                 375                 380

Asp Ile Pro Ser Ser Gln Gln Ser Leu Tyr Glu Lys Ala Gly Phe Tyr
385                 390                 395                 400

Ile Thr Ser Gly Ala Tyr Ile Leu Arg Pro Glu Val Ile Glu Ser Phe
                405                 410                 415

Tyr Tyr Ala Trp Arg Val Thr Gly Gln Glu Thr Tyr Arg Asp Trp Ile
            420                 425                 430

Trp Ser Ala Phe Ser Ala Val Asn Asp Tyr Cys Arg Thr Ser Ser Gly
            435                 440                 445

Phe Ser Gly Leu Thr Asp Val Asn Ala Ala Asn Gly Gly Ser Arg Tyr
            450                 455                 460

Asp Asn Gln Glu Ser Phe Leu Phe Ala Glu Val Met Lys Tyr Ser Tyr
465                 470                 475                 480

Met Ala Phe Ala Glu Asp Ala Ala Trp Gln Val Gln Pro Gly Ser Gly
                485                 490                 495

Asn Gln Phe Val Phe Asn Thr Glu Ala His Pro Val Arg Val Ser Ser
            500                 505                 510

Thr
```

DE-MANNOSYLATION OF PHOSPHORYLATED N-GLYCANS

CROSS-REFERENCE TO RELATED APPLICATIONS

This application is a National Stage application under 35 U.S.C. §371 of International Application No. PCT/IB2011/002780, having an International Filing Date of Sep. 29, 2011, which claims priority to U.S. Application Ser. No. 61/387,924, filed on Sep. 29, 2010. The disclosures of the prior applications are incorporated by reference in their entirety.

TECHNICAL FIELD

This invention relates to alpha-mannosidases that can hydrolyze the terminal α-1,2-mannose when the underlying mannose is phosphorylated.

BACKGROUND

High performance expression systems are required to produce most biopharmaceuticals (e.g., recombinant proteins) currently under development. The biological activity of many of these biopharmaceuticals is dependent on their post-translational modification (e.g., phosphorylation or glycosylation). A yeast-based expression system combines the ease of genetic manipulation and fermentation of a microbial organism with the capability to secrete and to modify proteins. However, recombinant glycoproteins produced in yeast cells exhibit mainly heterogeneous high-mannose and hyper-mannose glycan structures, which can be detrimental to protein function, downstream processing, and subsequent therapeutic use, particularly where glycosylation plays a biologically significant role.

SUMMARY

This document is based on the discovery of a mannosidase capable of hydrolyzing a terminal alpha-1,2 mannose linkage or moiety when the underlying mannose is phosphorylated.

In one aspect, this document features a method for demannosylating phosphorylated N-glycans on a glycoprotein. The method includes providing the glycoprotein having phosphorylated N-glycans; and contacting the glycoprotein with a mannosidase capable of hydrolyzing a terminal alpha-1,2 mannose linkage or moiety when the underlying mannose is phosphorylated. The mannosidase can be from *Aspergillus satoi* or *Cellulosimicrobium cellulans*. The method further can include isolating the glycoprotein containing the demannosylated phosphorylated N-glycan. The protein can be a human protein expressed in a fungal organism. For example, the fungal organism can be *Yarrowia lipolytica* or *Arxula adeninivorans*. The fungal organism also can be a methylotrophic yeast (e.g., *Pichia pastoris*, *Pichia methanolica*, *Oogataea minuta*, or *Hansenula polymorpha*) or a filamentous fungus (e.g., *Aspergillus caesiellus*, *Aspergillus candidus*, *Aspergillus carneus*, *Aspergillus clavatus*, *Aspergillus deflectus*, *Aspergillus flavus*, *Aspergillus fumigatus*, *Aspergillus glaucus*, *Aspergillus nidulans*, *Aspergillus niger*, *Aspergillus ochraceus*, *Aspergillus oryzae*, *Aspergillus parasiticus*, *Aspergillus penicilloides*, *Aspergillus restrictus*, *Aspergillus sojae*, *Aspergillus sydowi*, *Aspergillus tamari*, *Aspergillus terreus*, *Aspergillus ustus*, or *Aspergillus versicolor*). The protein can be a pathogen protein, a lysosomal protein, a growth factor, a cytokine, a chemokine, an antibody or antigen-binding fragment thereof, or a fusion protein. For example, the lysosomal protein can be a lysosomal enzyme such as a lysosomal enzyme associated with a lysosomal storage disorder (LSD). A LSD can be Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

This document also features a method of producing a target protein having demannosylated phosphorylated N-glycans in a fungal organism. The method includes providing a fungal cell genetically engineered to include a nucleic acid encoding a mannosidase capable of hydrolyzing a terminal alpha-1,2 mannose linkage or moiety when the underlying mannose is phosphorylated; and introducing into the cell a nucleic acid encoding a target protein.

This document also features an isolated fungal cell genetically engineered to produce glycoproteins that include demannosylated phosphorylated N-glycans. The fungal cell can be *Yarrowia lipolytica* or *Arxula adeninivorans*. The fungal cell also can be a methylotrophic yeast (e.g., *Pichia pastoris*, *Pichia methanolica*, *Oogataea minuta*, or *Hansenula polymorpha*) or a filamentous fungus (e.g., *Aspergillus caesiellus*, *Aspergillus candidus*, *Aspergillus carneus*, *Aspergillus clavatus*, *Aspergillus deflectus*, *Aspergillus flavus*, *Aspergillus fumigatus*, *Aspergillus glaucus*, *Aspergillus nidulans*, *Aspergillus niger*, *Aspergillus ochraceus*, *Aspergillus oryzae*, *Aspergillus parasiticus*, *Aspergillus penicilloides*, *Aspergillus restrictus*, *Aspergillus sojae*, *Aspergillus sydowi*, *Aspergillus tamari*, *Aspergillus terreus*, *Aspergillus ustus*, or *Aspergillus versicolor*). The fungal cell further can include a nucleic acid encoding a polypeptide capable of promoting mannosyl phosphorylation. The fungal cell can be genetically engineered to be deficient in OCH1 activity. The fungal cell further can include a nucleic acid encoding a polypeptide capable of promoting mannosyl phosphorylation, and wherein the fungal cell is genetically engineered to be deficient in OCH1 activity.

A fungal cell further can include a nucleic acid encoding a target protein, wherein the target protein is a glycoprotein. The target protein can be a human protein. The target protein can be a pathogen protein, a lysosomal protein, a growth factor, a cytokine, a chemokine, an antibody or antigen-binding fragment thereof, or a fusion protein. The lysosomal protein can be a lysosomal enzyme. The target protein can be a protein associated with a LSD such as Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

A polypeptide capable of promoting mannosyl phosphorylation can be a MNN4 polypeptide (e.g., a *Yarrowia liplytica, S. cerevisiae, Ogataea minuta, Pichia pastoris*, or *C. albicans* polypeptide). The polypeptide capable of promoting mannosyl phosphorylation can be a *P. pastoris* PNO1 polypeptide.

In yet another aspect, this document features a substantially pure culture of *Yarrowia lipolytica, Pichia pastoris, Hansenula polymorpha, Ogataea minuta, Pichia methanolica, Arxula adeninivorans*, or *Aspergillus niger* cells, a substantial number of which are genetically engineered to produce glycoproteins that contain demannosylated phosphorylated N-glycans. The cells further can include a nucleic acid encoding a polypeptide capable of promoting mannosyl phosphorylation. The cells can be genetically engineered to be deficient in OCH1 activity. The cells further can include a nucleic acid encoding a polypeptide capable of promoting mannosyl phosphorylation, and can be genetically engineered to be deficient in OCH1 activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 1A is a depiction of the codon optimized nucleotide sequence of human alpha glucosidase (GAA) with lip2 pre sequence in bold (SEQ ID NO:1). FIG. 1B is a depiction of the amino acid sequence of human GAA with lip2 pre sequence in bold, where the * represents the stop codon (SEQ ID NO: 2).

FIG. 3 is a depiction of the nucleotide sequence of the open reading frame (ORF) of DsbA-CcMan5 (SEQ ID NO:3).

FIG. 4 is a depiction of the nucleotide sequence of the ORF of DsbA-CcMan4 (SEQ ID NO: 4)

FIG. 5 is a schematic of the plasmids pLSAHCcMan5 and pLSAHCcMan4.

FIG. 15 is a depiction of the amino acid sequence of a mannosidase from *Aspergillus saitoi* (SEQ ID NO: 5).

DETAILED DESCRIPTION

Figure 2:
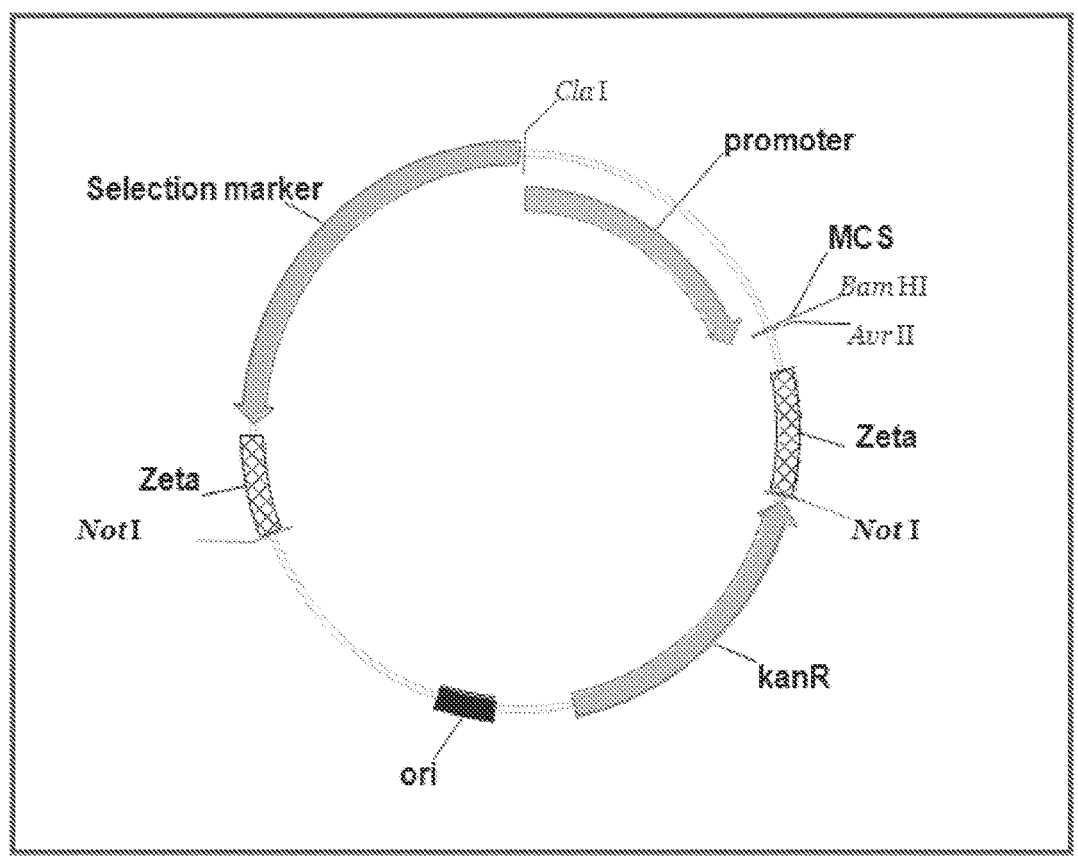
FIG. 2 is a schematic of a *Y. lipolytica* expression vector used for cloning of huGAA.

In general, this document provides methods and materials for hydrolyzing a terminal alpha-1,2 mannose linkage or moiety when the immediately underlying mannose is phosphorylated. The methods and materials described herein are particularly useful for producing agents for treating patients with lysosomal storage disorders (LSDs), a diverse group of hereditary metabolic disorders characterized by the accumulation of storage products in the lysosomes due to impaired activity of catabolic enzymes involved in their degradation. The build-up of storage products leads to cell dysfunction and progressive clinical manifestations. Deficiencies in catabolic enzymes can be corrected by enzyme replacement therapy (ERT), provided that the administered enzyme can be targeted to the lysosomes of the diseased cells. Lysosomal enzymes typically are glycoproteins that are synthesized in the endoplasmic reticulum (ER), transported via the secretory pathway to the Golgi, and then recruited to the lysosomes. Using the methods and materials described herein, a microbial based production process can be used to obtain therapeutic proteins with demannosylated phosphorylated N-glycans. Thus, the methods and materials described herein are useful for preparing glycoproteins for the treatment of metabolic disorders such as LSDs.

Mannosidases

This document provides isolated nucleic acids encoding mannosidases that can hydrolyze a terminal alpha-1,2 mannose linkage or moiety when the underlying mannose is phosphorylated. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

"Polypeptide" and "protein" are used interchangeably herein and mean any peptide-linked chain of amino acids, regardless of length or post-translational modification. Typically, a polypeptide described herein (e.g., a mannosidase or a demannosylated target protein) is isolated when it constitutes at least 60%, by weight, of the total protein in a preparation, e.g., 60% of the total protein in a sample. In some embodiments, a polypeptide described herein consists of at least 75%, at least 90%, or at least 99%, by weight, of the total protein in a preparation.

An "isolated nucleic acid" refers to a nucleic acid that is separated from other nucleic acid molecules that are present in a naturally-occurring genome, including nucleic acids that normally flank one or both sides of the nucleic acid in a naturally-occurring genome (e.g., a yeast genome). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The term "exogenous" as used herein with reference to nucleic acid and a particular host cell refers to any nucleic acid that does not occur in (and cannot be obtained from) that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast y.

A nucleic acid encoding a mannosidase can have at least 70% sequence identity (e.g., at least 80%, 85%, 90%, 95%, 97%, 98%, 99%, or 100% sequence identity) to a nucleotide sequence set forth in SEQ ID NO: 3 or SEQ ID NO:4. In some embodiments, nucleic acids described herein can encode mannosidase polypeptides that have at least 70% (e.g., at least 75, 80, 85, 90, 95, 99, or 100 percent) identity to an amino acid sequence set forth in SEQ ID NOs: 5. The percent identity between a particular amino acid sequence and the amino acid sequence set forth in SEQ ID NO:5 can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length mannosidase polypeptide amino acid sequence followed by multiplying the resulting value by 100.

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given mannosidase polypeptide can be modified such that optimal expression in a particular species (e.g., bacteria or fungus) is obtained, using appropriate codon bias tables for that species.

Hybridization also can be used to assess homology between two nucleic acid sequences. A nucleic acid sequence described herein, or a fragment or variant thereof, can be used as a hybridization probe according to standard hybridization techniques. The hybridization of a probe of interest (e.g., a probe containing a portion of an *Aspergillus saitoi* nucleotide sequence) to DNA or RNA from a test source is an indication of the presence of DNA or RNA (e.g., an *Aspergillus saitoi* nucleotide sequence) corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

Other mannosidase polypeptide candidates suitable for use herein can be identified by analysis of nucleotide and polypeptide sequence alignments. For example, performing a query on a database of nucleotide or polypeptide sequences can identify homologs and/or orthologs of mannosidase polypeptides. Sequence analysis can involve BLAST, Reciprocal BLAST, or PSI-BLAST analysis of nonredundant databases using known mannosidase amino acid sequences. Those polypeptides in the database that have greater than 40% sequence identity can be identified as candidates for further evaluation for suitability as a mannosidase polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated.

This document also provides (i) biologically active variants and (ii) biologically active fragments or biologically active variants thereof, of the mannosidases described herein. Biologically active variants of mannosidases can contain additions, deletions, or substitutions relative to the amino acid sequence set forth in SEQ ID NOs: 5 or the amino acid sequence encoded by the nucleotide sequences set forth in SEQ ID NOs: 3 and 4. Proteins with substitutions will generally have not more than 50 (e.g., not more than one, two, three, four, five, six, seven, eight, nine, ten, 12, 15, 20, 25, 30, 35, 40, or 50) conservative amino acid substitutions. A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a non-conservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Additions (addition variants) include fusion proteins containing: (a) a mannosidase encoded by the nucleic acid sequences set forth in SEQ ID NOs: 3 or 4 or the mannosidase having the amino acid sequence set forth in SEQ ID NOs: 5 or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltose-binding protein (MBP)). Heterologous sequences also can be proteins useful as diagnostic or detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or endoplasmic reticulum or Golgi apparatus retention signals. Heterologous sequences can be of varying length and in some cases can be a longer sequences than the full-length target proteins to which the heterologous sequences are attached.

Biologically active fragments or biologically active variants of the mannosidases have at least 40% (e.g., at least: 50%; 60%; 70%; 75%; 80%; 85%; 90%; 95%; 97%; 98%; 99%; 99.5%, or 100% or even greater) of the mannosidase activity (e.g., demannosylating) of the wild-type, full-length, mature protein.

The mannosidases described herein can be used to produce demannosylated target molecules. The methods can be performed in vitro or in vivo.

Methods of Demannosylating Glycoproteins

As described herein, glycoproteins containing phosphorylated N-glycans can be demannosylated using a mannosidase that can hydrolyze a terminal alpha-1,2 mannose linkage or moiety when the underlying mannose is phosphorylated. Non-limiting examples of such mannosidases include a mannosidase from *Aspergillus satoi* (As) (also known as *Aspergillus phoenicis*) or a mannosidase from *Cellulosimicrobium cellulans* (e.g., CcMan4). The amino acid sequence of the *Aspergillus satoi* mannosidase is set forth in SEQ ID NO:5 (see FIG. 15) and in GenBank Accession No. BAA08634. A CcMan4 polypeptide is encoded by the nucleotide sequence set forth in SEQ ID NO: 4 (see FIG. 4).

The *Aspergillus satoi* mannosidase and a *Cellulosimicrobium cellulans* mannosidase (e.g., CcMan4) can be recombinantly produced. Isolated nucleic acid molecules encoding mannosidase polypeptides can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids also can be obtained by mutagenesis of, e.g., a naturally occurring DNA.

To recombinantly produce a mannosidase polypeptide, a vector is used that contains a promoter operably linked to nucleic acid encoding the mannosidase polypeptide. As used herein, a "promoter" refers to a DNA sequence that enables a gene to be transcribed. The promoter is recognized by RNA polymerase, which then initiates transcription. Thus, a promoter contains a DNA sequence that is either bound directly by, or is involved in, the recruitment, of RNA polymerase. A promoter sequence can also include "enhancer regions," which are one or more regions of DNA that can be bound with proteins (namely, the trans-acting factors, much like a set of transcription factors) to enhance transcription levels of genes (hence the name) in a gene-cluster. The enhancer, while typically at the 5' end of a coding region, can also be separate from a promoter sequence and can be, e.g., within an intronic region of a gene or 3' to the coding region of the gene.

As used herein, "operably linked" means incorporated into a genetic construct (e.g., vector) so that expression control sequences effectively control expression of a coding sequence of interest.

Expression vectors can be introduced into host cells (e.g., by transformation or transfection) for expression of the encoded polypeptide, which then can be purified. Expression systems that can be used for small or large scale production of mannosidase polypeptides include, without limitation, microorganisms such as bacteria (e.g., *E. coli*) transformed with recombinant bacteriophage DNA, plasmid DNA, or cosmid DNA expression vectors containing the nucleic acid molecules, and fungal (e.g., *S. cerevisiae, Yarrowia lipolytica, Arxula adeninivorans, Pichia pastoris, Hansenula polymorpha,* or *Aspergillus*) transformed with recombinant fungal expression vectors containing the nucleic acid molecules. Useful expression systems also include insect cell systems infected with recombinant virus expression vectors (e.g., baculovirus) containing the nucleic acid molecules, and plant cell systems infected with recombinant virus expression vectors (e.g., tobacco mosaic virus) or transformed with recombinant plasmid expression vectors (e.g., Ti plasmid) containing the nucleic acid molecules. Mannosidase polypeptides also can be produced using mammalian expression systems, which include cells (e.g., immortalized cell lines such as COS cells, Chinese hamster ovary cells, HeLa cells, human embryonic kidney 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter).

Typically, recombinant mannosidase polypeptides are tagged with a heterologous amino acid sequence such FLAG, polyhistidine (e.g., hexahistidine), hemagluttanin (HA), glutathione-S-transferase (GST), or maltose-binding protein (MBP) to aid in purifying the protein. Other methods for purifying proteins include chromatographic techniques such as ion exchange, hydrophobic and reverse phase, size exclusion, affinity, hydrophobic charge-induction chromatography, and the like (see, e.g., Scopes, Protein Purification: Principles and Practice, third edition, Springer-Verlag, New York (1993); Burton and Harding, *J. Chromatogr. A* 814: 71-81 (1998)).

To produce demannosylated glycoproteins, a target molecule containing a terminal alpha-1,2 mannose linkage or moiety where the underlying mannose is phosphorylated is contacted under suitable conditions with a mannosidase or a cell lysate containing a recombinantly produced mannosidase. Suitable mannosidases are described above. The cell lysate can be from any genetically engineered cell, including a fungal cell, a plant cell, or animal cell. Non-limiting examples of animal cells include nematode, insect, plant, bird, reptile, and mammals such as a mouse, rat, rabbit, hamster, gerbil, dog, cat, goat, pig, cow, horse, whale, monkey, or human.

Upon contacting the target molecule (e.g., a glycoprotein) with the purified mannosidase or cell lysate, the terminal alpha-1,2 mannose linkage can be hydrolyzed to produces a demannosylated target molecule.

Suitable methods for obtaining cell lysates that preserve the activity or integrity of the mannosidase activity in the lysate can include the use of appropriate buffers and/or inhibitors, including nuclease, protease and phosphatase inhibitors that preserve or minimize changes in N-glycosylation activities in the cell lysate. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for obtaining lysates containing enzymatic activities are described in, e.g., Ausubel et al. Current Protocols in Molecular Biology (Supplement 47), John Wiley & Sons, New York (1999); Harlow and Lane, Antibodies: A Laboratory Manual Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W. B. Saunders, Philadelphia, (1999).

A cell lysate can be further processed to eliminate or minimize the presence of interfering substances, as appropriate. If desired, a cell lysate can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like.

In some embodiments, a cell lysate can be prepared in which whole cellular organelles remain intact and/or functional. For example, a lysate can contain one or more of intact rough endoplasmic reticulum, intact smooth endoplasmic reticulum, or intact Golgi apparatus. Suitable methods for preparing lysates containing intact cellular organelles and testing for the functionality of the organelles are described in, e.g., Moreau et al. (1991) *J. Biol. Chem.* 266(7):4329-4333; Moreau et al. (1991) *J. Biol. Chem.* 266(7):4322-4328; Rexach et al. (1991) *J. Cell Biol.* 114 (2):219-229; and Paulik et al. (1999) *Arch. Biochem. Biophys.* 367(2):265-273.

Target molecules, as used herein, refer to any molecule containing a terminal alpha-1,2 mannose linkage or moiety where the underlying mannose is phosphorylated. In some embodiments, the target protein is a human glycoprotein. Suitable target proteins can include pathogen proteins such as tetanus toxoid or diptheria toxoid; viral surface proteins such as cytomegalovirus (CMV) glycoproteins B, H and gCIII, human immunodeficiency virus 1 (HIV-1) envelope glycoproteins, Rous sarcoma virus (RSV) envelope glycoproteins, herpes simplex virus (HSV) envelope glycoproteins, Epstein Barr virus (EBV) envelope glycoproteins, varicella-zoster virus (VZV) envelope glycoproteins, human papilloma virus (HPV) envelope glycoproteins, Influenza virus glycoproteins, and Hepatitis family surface antigen; lysosomal proteins (e.g., acid alpha glucosidase, alpha galatosidase, glucocerebrosidase, cerebrosidase, or galactocerebrosidase); insulin; glucagons; growth factors; cytokines; chemokines; and antibodies or fragments thereof. Growth factors include, e.g., vascular endothelial growth factor (VEGF), Insulin-like growth factor (IGF), bone morphogenic protein (BMP), Granulocyte-colony stimulating factor (G-CSF), Granulocyte-macrophage colony stimulating factor (GM-CSF), Nerve growth factor (NGF); a Neurotrophin, Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), Epidermal growth factor (EGF), Hepatocyte growth factor (HGF). Cytokines include, for example, interleukins such as IL-1 to IL-33 (e.g., IL-1, IL-2, IL-3, IL-4, IL-5, IL-6, IL-7, IL-8, IL-9, IL-10, IL-12, IL-13, or IL-15)). Chemokines include, e.g., 1-309, TCA-3, MCP-1, MIP-1α, MIP-1β, RANTES, C10, MRP-2, MARC, MCP-3, MCP-2, MRP-2, CCF18, MIP-1γ, Eotaxin, MCP-5, MCP-4, NCC-1, Ckβ10, HCC-1, Leukotactin-1, LEC, NCC-4, TARC, PARC, or Eotaxin-2. Also included are tumor glycoproteins (e.g., tumor-associated antigens), for example, carcinoembryonic antigen (CEA), human mucins, HER-2/neu, and prostate-specific antigen (PSA) [Henderson and Finn, *Advances in Immunology*, 62, pp. 217-56 (1996)].

In some embodiments, the target protein can be one associated with a lysosomal storage disorder, which target proteins include, e.g., acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neuraminidase, phosphotransferase, acid lipase, acid ceramidase, sphingomyelinase, thioesterase, cathepsin K, and lipoprotein lipase.

In some embodiments, the target proteins are fusion proteins in which the target protein is fused to another polypeptide sequence, or to a polymer, a carrier, an adjuvant, an immunotoxin, or a detectable (e.g., fluorescent, luminescent, or radioactive) moiety. For example, a target protein can be joined to a polymer such as polyethyleneglycol to increase the molecular weight of small proteins and/or increase circulation residence time.

In Vivo Methods of Demannosylating Glycoproteins

Genetically engineered cells described herein can be used to produce demannosylated target molecules. For example, a cell based method can include the steps of introducing into a fungal cell genetically engineered to include a nucleic acid encoding a mannosidase that is capable of hydrolyzing a terminal alpha-1,2 mannose linkage or moiety when the underlying mannose is phosphorylated, a nucleic acid encoding a target molecule, wherein the cell produces the target molecule containing demannosylated phosphorylated N-glycans. In some embodiments, the nucleic acids encoding the mannosidase and target molecule contain a secretion sequence such that the mannosidase and target molecule are co-secreted.

Genetically engineered cells described herein contain a nucleic acid encoding a mannosidase. Cells suitable for in vivo production of target molecules can be of fungal origin, including *Yarrowia lipolytica*, *Arxula adeninivorans*, methylotrophic yeast (such as a methylotrophic yeast of the genus *Candida*, *Hansenula*, *Oogataea*, *Pichia* or *Torulopsis*) or filamentous fungi of the genus *Aspergillus*, *Trichoderma*, *Neurospora*, *Fusarium*, or *Chrysosporium*. Exemplary fungal species include, without limitation, *Pichia anomala*, *Pichia bovis*, *Pichia canadensis*, *Pichia carsonii*, *Pichia farinose*, *Pichia fermentans*, *Pichia fluxuum*, *Pichia membranaefaciens*, *Pichia membranaefaciens*, *Candida valida*, *Candida albicans*, *Candida ascalaphidarum*, *Candida amphixiae*, *Candida Antarctica*, *Candida atlantica*, *Candida atmosphaerica*, *Candida blattae*, *Candida carpophila*, *Candida cerambycidarum*, *Candida chauliodes*, *Candida corydalis*, *Candida dosseyi*, *Candida dubliniensis*, *Candida ergatensis*, *Candida fructus*, *Candida glabrata*, *Candida fermentati*, *Candida guilliermondii*, *Candida haemulonii*, *Candida insectamens*, *Candida insectorum*, *Candida intermedia*, *Candida jeffresii*, *Candida kefyr*, *Candida krusei*, *Candida lusitaniae*, *Candida lyxosophila*, *Candida maltosa*, *Candida membranifaciens*, *Candida milleri*, *Candida oleophila*, *Candida oregonensis*, *Candida parapsilosis*, *Candida quercitrusa*, *Candida shehatea*, *Candida temnochilae*, *Candida tenuis*, *Candida tropicalis*, *Candida tsuchiyae*, *Candida sinolaborantium*, *Candida sojae*, *Candida viswanathii*, *Candida utilis*, *Oogataea minuta*, *Pichia membranaefaciens*, *Pichia silvestris*, *Pichia membranaefaciens*, *Pichia chodati*, *Pichia membranaefaciens*, *Pichia menbranaefaciens*, *Pichia minuscule*, *Pichia pastoris*, *Pichia pseudopolymorpha*, *Pichia quercuum*, *Pichia robertsii*, *Pichia saitoi*, *Pichia silvestrisi*, *Pichia strasburgensis*, *Pichia terricola*, *Pichia vanriji*, *Pseudozyma Antarctica*, *Rhodosporidium toruloides*, *Rhodotorula glutinis*, *Saccharomyces bayanus*, *Saccharomyces bayanus*, *Saccharomyces momdshuricus*, *Saccharomyces uvarum*, *Saccharomyces bayanus*, *Saccharomyces cerevisiae*, *Saccharomyces bisporus*, *Saccharomyces chevalieri*, *Saccharomyces delbrueckii*, *Saccharomyces exiguous*, *Saccharomyces fermentati*, *Saccharomyces fragilis*, *Saccharomyces marxianus*, *Saccharomyces mellis*, *Saccharomyces rosei*, *Saccharomyces rouxii*, *Saccharomyces uvarum*, *Saccharomyces willianus*, *Saccharomycodes ludwigii*, *Saccharomycopsis capsularis*, *Saccharomycopsis fibuligera*, *Saccharomycopsis fibuligera*, *Endomyces hordei*, *Endomycopsis fobuligera*. *Saturnispora saitoi*, *Schizosaccharomyces octosporus*, *Schizosaccharomyces pombe*, *Schwanniomyces occidentalis*, *Torulaspora delbrueckii*, *Torulaspora delbrueckii*, *Saccharomyces dairensis*, *Torulaspora delbrueckii*, *Torulaspora fermentati*, *Saccharomyces fermentati*, *Torulaspora delbrueckii*, *Torulaspora rosei*, *Saccharomyces rosei*, *Torulaspora delbrueckii*, *Saccharomyces rosei*, *Torulaspora delbrueckii*, *Saccharomyces delbrueckii*, *Torulaspora delbrueckii*, *Saccharomyces delbrueckii*, *Torulaspora delbrueckii*, *Saccharomyces delbrueckii*, *Torulaspora delbrueckii*, *Zygosaccharomyces mongolicus*, *Dorulaspora globosa*, *Debaryomyces globosus*, *Torulopsis globosa*, *Trichosporon cutaneum*, *Trigonopsis variabilis*, *Williopsis californica*, *Williopsis saturnus*, *Zygosaccharomyces bisporus*, *Zygosaccharomyces bisporus*, *Debaryomyces disporua*. *Saccharomyces bisporas*, *Zygosaccharomyces bisporus*, *Saccharomyces bisporus*, *Zygosaccharomyces mellis*, *Zygosaccharomyces priorianus*, *Zygosaccharomyces rouxiim*, *Zygosaccharomyces rouxii*, *Zygosaccharomyces barkeri*, *Saccharomyces rouxii*, *Zygosaccharomyces rouxii*,

*Zygosaccharomyces major, Saccharomyces rousii, Pichia anomala, Pichia bovis, Pichia Canadensis, Pichia carsonii, Pichia farinose, Pichia fermentans, Pichia fluxuum, Pichia membranaefaciens, Pichia pseudopolymorpha, Pichia quercuum, Pichia robertsii, Pseudozyma Antarctica, Rhodosporidium toruloides, Rhodosporidium toruloides, Rhodotorula glutinis, Saccharomyces bayanus, Saccharomyces bayanus, Saccharomyces bisporus, Saccharomyces cerevisiae, Saccharomyces chevalieri, Saccharomyces delbrueckii, Saccharomyces fermentati, Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis,* or *Zygosaccharomyces rouxii.* Exemplary filamentous fungi include various species of *Aspergillus* including, but not limited to, *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus,* or *Aspergillus versicolor.* Such cells, prior to the genetic engineering as specified herein, can be obtained from a variety of commercial sources and research resource facilities, such as, for example, the American Type Culture Collection (Rockville, Md.). Target molecules include proteins such as any of the target proteins described herein (see above).

Genetic engineering of a cell can include, in addition to an exogenous nucleic acid encoding a mannosidase, one or more genetic modifications such as: (i) deletion of an endogenous gene encoding an Outer CHain elongation (OCH1) protein; (ii) introduction of a recombinant nucleic acid encoding a polypeptide capable of promoting mannosyl phosphorylation (e.g, a MNN4 polypeptide from *Yarrowia lipolytica, S. cerevisiae, Ogataea minuta, Pichia pastoris,* or *C. albicans,* or PNO1 polypeptide from *P. pastoris*) to increasing phosphorylation of mannose residues; (iii) introduction or expression of an RNA molecule that interferes with the functional expression of an OCH1 protein; (iv) introduction of a recombinant nucleic acid encoding a wild-type (e.g., endogenous or exogenous) protein having a N-glycosylation activity (i.e., expressing a protein having an N-glycosylation activity); (v) introduction of a recombinant nucleic acid encoding a target molecule described above; or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., by site-directed mutagenesis or homologous recombination) or can be introduced randomly (for example, cells can be chemically mutagenized as described in, e.g., Newman and Ferro-Novick (1987) *J. Cell Biol.* 105(4):1587.

Genetic modifications described herein can result in one or more of (i) an increase in one or more activities in the genetically modified cell, (ii) a decrease in one or more activities in the genetically modified cell, or (iii) a change in the localization or intracellular distribution of one or more activities in the genetically modified cell. It is understood that an increase in the amount of a particular activity (e.g., promoting mannosyl phosphorylation) can be due to over-expressing one or more proteins capable of promoting mannosyl phosphorylation, an increase in copy number of an endogenous gene (e.g., gene duplication), or an alteration in the promoter or enhancer of an endogenous gene that stimulates an increase in expression of the protein encoded by the gene. A decrease in one or more particular activities can be due to overexpression of a mutant form (e.g., a dominant negative form), introduction or expression of one or more interfering RNA molecules that reduce the expression of one or more proteins having a particular activity, or deletion of one or more endogenous genes that encode a protein having the particular activity.

To disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis. A selectable marker can be removed from the genome of the host cell by, e.g., Cre-loxP systems (see below).

Alternatively, a gene replacement vector can be constructed in such a way as to include a portion of the gene to be disrupted, which portion is devoid of any endogenous gene promoter sequence and encodes none or an inactive fragment of the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression vectors can be autonomous or integrative. A recombinant nucleic acid (e.g., one encoding a mannosidase) can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362). Expression vectors can also include an autonomous replication sequence (ARS). For example, U.S. Pat. No. 4,837,148 describes autonomous replication sequences which provide a suitable means for maintaining plasmids in *Pichia pastoris*.

Integrative vectors are disclosed, e.g., in U.S. Pat. No. 4,882,279. Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding a protein having N-glycosylation activity) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., *Yarrowia lipolytica, Arxula adeninivorans, P. pastoris*, or other suitable fungal species) promoter, which enables them to be expressed in fungal cells. Suitable yeast promoters include, e.g., ADC1, TPI1, ADH2, hp4d, POX, and Gal10 (see, e.g., Guarente et al. (1982) *Proc. Natl. Acad. Sci. USA* 79(23):7410) promoters. Additional suitable promoters are described in, e.g., Zhu and Zhang (1999) *Bioinformatics* 15(7-8):608-611 and U.S. Pat. No. 6,265,185.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

It is understood that other genetically engineered modifications can also be conditional. For example, a gene can be conditionally deleted using, e.g., a site-specific DNA recombinase such as the Cre-loxP system (see, e.g., Gossen et al. (2002) *Ann. Rev. Genetics* 36:153-173 and U.S. Application Publication No. 20060014264).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreekrishna et al. (1987) *Gene* 59:115, the disclosures of each of which are incorporated herein by reference in their entirety. Electroporation and PEG1000 whole cell transformation procedures may also be used, as described by Cregg and Russel, Methods in Molecular Biology: *Pichia* Protocols, Chapter 3, Humana Press, Totowa, N.J., pp. 27-39 (1998).

Transformed fungal cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*) as described above. The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

In some embodiments, the genetically engineered fungal cell lacks the OCH1 gene or gene products (e.g., mRNA or protein) thereof, and is deficient in OCH1 activity. In some embodiments, the genetically engineered cell expresses a polypeptide capable of promoting mannosyl phosphorylation (e.g., a MNN4 polypeptide from *Yarrowia lipolytica, S. cerevisiae, Ogataea minuta, Pichia pastoris*, or *C. albicans*, or a PNO1 polypeptide from *P. pastoris*). For example, the fungal cell can express a MNN4 polypeptide from *Y. lipolytica* (Genbank® Acccession Nos: XM_503217, Genolevures Ref: YALI0D24101g). In some embodiments, the genetically engineered cell is deficient in OCH1 activity and expresses a polypeptide capable of promoting mannosyl phosphorylation.

Following demannosylation, the target molecule can be isolated. In some embodiments, the target molecule is maintained within the yeast cell and released upon cell lysis. In some embodiments, the target molecule is secreted into the culture medium via a mechanism provided by a coding sequence (either native to the exogenous nucleic acid or engineered into the expression vector), which directs secretion of the molecule from the cell. The presence of the uncapped and demannosylated target molecule in the cell lysate or culture medium can be verified by a variety of standard protocols for detecting the presence of the molecule. For example, where the altered target molecule is a protein, such protocols can include, but are not limited to, immunoblotting or radioimmunoprecipitation with an antibody specific for the altered target protein (or the target protein itself), binding of a ligand specific for the altered target protein (or the target protein itself), or testing for a specific enzyme activity of the altered target protein (or the target protein itself).

In some embodiments, following isolation, the demannosylated target molecule can be attached to a heterologous moiety, e.g., using enzymatic or chemical means. A "heterologous moiety" refers to any constituent that is joined (e.g., covalently or non-covalently) to the altered target molecule, which constituent is different from a constituent originally present on the altered target molecule. Heterologous moieties include, e.g., polymers, carriers, adjuvants, immunotoxins, or detectable (e.g., fluorescent, luminescent, or radioactive) moieties. In some embodiments, an additional N-glycan can be added to the altered target molecule.

Methods for detecting glycosylation of a target molecule include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Isolated mannoproteins can be further treated with one or more enzymes such as calf intestine phosphatase to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) *Glycobiology* 11(4):275-281 and Freire et al. (2006) *Bioconjug. Chem.* 17(2):559-564.

Cultures of Engineered Cells

This document also provides a substantially pure culture of any of the genetically engineered cells described herein. As used herein, a "substantially pure culture" of a genetically engineered cell is a culture of that cell in which less than about 40% (i.e., less than about : 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Metabolic Disorders

Demannosylated molecules can be used to treat a variety of metabolic disorders. A metabolic disorder is one that affects the production of energy within individual human (or animal) cells. Most metabolic disorders are genetic, though some can be "acquired" as a result of diet, toxins, infections, etc. Genetic metabolic disorders are also known as inborn errors of metabolism. In general, the genetic metabolic disorders are caused by genetic defects that result in missing or improperly constructed enzymes necessary for some step in the metabolic process of the cell. The largest classes of metabolic disorders are disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism disorders of mitochondrial function, disorders of peroxisomal function, and lysosomal storage disorders (LSDs).

Examples of metabolic disorders that can be treated through the administration of one or more demannosylated molecules (or pharmaceutical compositions of the same) can include hereditary hemochromatosis, oculocutaneous albinism, protein C deficiency, type I hereditary angioedema, congenital sucrase-isomaltase deficiency, Crigler-Najjar type II, Laron syndrome, hereditary Myeloperoxidase, primary hypothyroidism, congenital long QT syndrome, tyroxine binding globulin deficiency, familial hypercholesterolemia, familial chylomicronemia, abeta-lipoproteinema, low plasma lipoprotein A levels, hereditary emphysema with liver injury, congenital hypothyroidism, osteogenesis imperfecta, hereditary hypofibrinogenemia, alpha-1 antichymotrypsin deficiency, nephrogenic diabetes insipidus, neurohypophyseal diabetes insipidus, adenosine deaminase deficiency, Pelizaeus Merzbacher disease, von Willebrand disease type IIA, combined factors V and VIII deficiency, spondylo-epiphyseal dysplasia tarda, choroideremia, I cell disease, Batten disease, ataxia telangiectasias, ADPKD-autosomal dominant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adrenoleukodystrophy, Scott syndrome, Hermansky-Pudlak syndrome types 1 and 2, Zellweger syndrome, rhizomelic chondrodysplasia puncta, autosomal recessive primary hyperoxaluria, Mohr Tranebjaerg syndrome, spinal and bullar muscular atrophy, primary ciliary diskenesia (Kartagener's syndrome), giantism and acromegaly, galactorrhea, Addison's disease, adrenal virilism, Cushing's syndrome, ketoacidosis, primary or secondary aldosteronism, Miller Dieker syndrome, lissencephaly, motor neuron disease, Usher's syndrome, Wiskott-Aldrich syndrome, Optiz syndrome, Huntington's disease, hereditary pancreatitis, anti-phospholipid syndrome, overlap connective tissue disease, Sjögren's syndrome, stiff-man syndrome, Brugada syndrome, congenital nephritic syndrome of the Finnish type, Dubin-Johnson syndrome, X-linked hypophosphosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharidosis type IV, hereditary familial amyloidosis of Finish, Anderson disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented retinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. In addition, metabolic disorders can also include lysosomal storage disorders such as, but not limited to, Fabry disease, mucopolysaccharidosis I, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis (types II, III, and IV), cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

Symptoms of a metabolic disorder are numerous and diverse and can include one or more of, e.g., anemia, fatigue, bruising easily, low blood platelets, liver enlargement, spleen enlargement, skeletal weakening, lung impairment, infections (e.g., chest infections or pneumonias), kidney impairment, progressive brain damage, seizures, extra thick meconium, coughing, wheezing, excess saliva or mucous production, shortness of breath, abdominal pain, occluded bowel or gut, fertility problems, polyps in the nose, clubbing of the finger/toe nails and skin, pain in the hands or feet, angiokeratoma, decreased perspiration, corneal and lenticular opacities, cataracts, mitral valve prolapse and/or regurgitation, cardiomegaly, temperature intolerance, difficulty walking, difficulty swallowing, progressive vision loss, progressive hearing loss, hypotonia, macroglossia, areflexia, lower back pain, sleep apnea, orthopnea, somnolence, lordosis, or scoliosis. It is understood that due to the diverse nature of the defective or absent proteins and the resulting disease phenotypes (e.g., symptomatic presentation of a metabolic disorder), a given disorder will generally present only symptoms characteristic to that particular disorder. For example, a patient with Fabry disease can present a particular subset of the above-mentioned symptoms such as, but not limited to, temperature intolerance, corneal whirling, pain, skin rashes, nausea, or diarrhea. A patient with Gaucher syndrome can present with splenomegaly, cirrhosis, convulsions, hypertonia, apnea, osteoporosis, or skin discoloration.

In addition to the administration of one or more demannosylated molecules described herein, a metabolic disorder can also be treated by proper nutrition and vitamins (e.g., cofactor therapy), physical therapy, and pain medications.

Depending on the specific nature of a given metabolic disorder, a patient can present these symptoms at any age. In many cases, symptoms can present in childhood or in early adulthood. For example, symptoms of Fabry disease can present at an early age, e.g., at 10 or 11 years of age.

As used herein, a subject "at risk of developing a metabolic disorder" is a subject that has a predisposition to develop a disorder, i.e., a genetic predisposition to develop metabolic disorder as a result of a mutation in a enzyme such as acid alpha glucosidase, alpha galactosidase, alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neurominidase, phosphotransferase, acid lipase, acid ceramidase, sphinogmyelinase, thioesterase, cathepsin K, or lipoprotein lipase. Clearly, subjects "at risk of developing a metabolic disorder" are not all the subjects within a species of interest.

A subject "suspected of having a disorder" is one having one or more symptoms of a metabolic disorder such as any of those described herein.

Pharmaceutical Compositions and Methods of Treatment

A demannosylated target molecule can be incorporated into a pharmaceutical composition containing a therapeutically effective amount of the molecule and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing demannosylated molecules can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted altered N-glycosylation molecule production cells). See, e.g., U.S. Pat. Nos. 4,407,957, 5,798, 113, and 5,800,828. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984); microencapsulation (see, e.g., U.S. Pat. Nos. 4,352,883; 4,353,888; and 5,084,350); continuous release polymer implants (see, e.g., Sabel, U.S. Pat. No. 4,883,666); macroencapsulation (see, e.g., U.S. Pat. Nos. 5,284,761, 5,158,881, 4,976,859 and 4,968,733 and published PCT patent applications WO92/19195, WO 95/05452); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

A demannosylated molecule suitable for topical administration can be administered to a mammal (e.g., a human patient) as, e.g., a cream, a spray, a foam, a gel, an ointment, a salve, or a dry rub. A dry rub can be rehydrated at the site of administration. Such molecules can also be infused directly into (e.g., soaked into and dried) a bandage, gauze, or patch, which can then be applied topically. Such molecules can also be maintained in a semi-liquid, gelled, or fully-liquid state in a bandage, gauze, or patch for topical administration (see, e.g., U.S. Pat. No. 4,307,717).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a demannosylated molecule can be first administered at different dosing regimens. The unit dose and regimen depend on factors that include, e.g., the species of mammal, its immune status, the body weight of the mammal. Typically, levels of such a molecule in a tissue can be monitored using appropriate screening assays as part of a clinical testing procedure, e.g., to determine the efficacy of a given treatment regimen.

The frequency of dosing for a demannosylated molecule is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such molecules or pharmaceutical compositions thereof can be determined by known pharmaceutical procedures in, for example, cell cultures or experimental animals. These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the $ED_{50}$ with little or no toxicity. The dosage may vary within this range depending upon the dosage form employed and the route of administration utilized. For a pharmaceutical composition used as described herein (e.g., for treating a metabolic disorder in a subject), the therapeutically effective dose can be estimated initially from cell culture assays. A dose can be formulated in animal models to achieve a circulating plasma concentration range that includes the $IC_{50}$ (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of a demannosylated molecule is an amount of the molecule that is capable of producing a medically desirable result (e.g., amelioration of one or more symptoms of a metabolic disorder) in a treated subject. A therapeutically effective amount (i.e., an effective dosage) can includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

A molecule or pharmaceutical composition thereof described herein can be administered to a subject as a combination therapy with another treatment, e.g., a treatment for a metabolic disorder (e.g., a lysosomal storage disorder). For example, the combination therapy can include administering to the subject (e.g., a human patient) one or more additional agents that provide a therapeutic benefit to the subject who has, or is at risk of developing, (or suspected of having) a metabolic disorder (e.g., a lysosomal storage disorder). Thus, the compound or pharmaceutical composition and the one or more additional agents can be administered at the same time. Alternatively, the molecule can be administered first and the one or more additional agents administered second, or vice versa.

It will be appreciated that in instances where a previous therapy is particularly toxic (e.g., a treatment for a metabolic disorder with significant side-effect profiles), administration of a molecule described herein can be used to offset and/or lessen the amount of the previously therapy to a level sufficient to give the same or improved therapeutic benefit, but without the toxicity.

Any of the pharmaceutical compositions described herein can be included in a container, pack, or dispenser together with instructions for administration.

The following are examples of the practice of the invention. They are not to be construed as limiting the scope of the invention in any way.

EXAMPLES

Example 1

Generation of an huGAA Expression Strain

*Y. lipolytica* strain OXYY1589 was constructed that contained three copies of the human alpha glucosidase (also known as acid alpha glucosidase (GAA) or acid maltase EC3.2.1.3) and two copies of the *Y. lipolytica* MNN4 gene. The genotype of strain OXY1589 is as follows:

MatA, leu2-958, ura3-302, xpr2-322, gut2-744, ade2-844
POX2-Lip2pre-huGAA:URA3Ex::zeta
POX2-Lip2pre-huGAA:LEU2Ex::zeta
POX2-Lip2pre-hGM-CSF:GUTEx::zeta
YlMNN4-POX2-hp4d-YLMNN4:ADE2::PT targeted All transformations were carried out according to well established protocols with modifications for the different selective markers. In all cases (unless otherwise specified), a huGAA integration fragment was obtained by NotI restriction digestion in order to remove the kanamycin resistance gene from the expression plasmids. The resulting fragments were all separated by agarose gel electrophoresis followed by Qiagen column purification of the correct huGAA fragment. Strain OXYY1589 was constructed by first cloning human GAA (huGAA) into a *Y. lipolytica* expression vector and constructing a *Y. lipolytica* MNN4 tandem expression vector. Three stable integrative transformations were then performed in order to obtain the final huGAA production strain OXYY1589.

*Y. lipolytica* codon optimized huGAA expression vector: The nucleotide sequence encoding the 110 kDA human GAA (huGAA) precursor was chemically synthesized and codon optimized for *Y. lipolytica* expression. In the synthetic construct, the pre- and the pro-huGAA signal peptides were eliminated such that the protein starts at amino acid 57. The synthetic ORF of huGAA (FIG. 1A) is fused in frame at the 5' end to the 3'end of the *Y. lipolytica* LIP2 signal sequence (pre), followed by the coding sequence of two Xxx-Ala cleavage sites and flanked by BamHI and AvrII restriction sites for cloning in expression vector. The construct is under the control of the inducible POX2 promoter. The complete amino acid sequence of the fusion protein is shown on FIG. 1B.

A general scheme of an expression vector is presented in FIG. 2. The bacterial moiety was derived from the plasmid pHSS6, and comprises a bacterial origin of replication (ori) and the kanamycin-resistant gene conferring resistance to kanamycin (KanR). The integration cassette comprised a) the selection marker for transformation to *Yarrowia lipolytica* (URA3; LEU2; GUT2), b) the expression cassette composed of a promoter, c) a multiple cloning site (MCS) to insert huGAA in frame with signal sequence and d) the terminator of the LIP2 gene. The integration cassette was flanked by zeta sequences for stable non-homologous integration into the *Y. lipolytica* genome. Two NotI restriction sites enable the isolation of the expression cassette before transformation. Plasmids pRAN034, pRAN036 and OXYP183 were used to generate huGAA expression vectors pRAN058, pRAN059 and pRAN060, respectively, containing URA3, LEU2 and GUT2 transformation markers, respectively.

Tandem YlMNN4 expression vector: The YlMNN4 gene was cloned under control of the inducible pPOX2 promoter and the (semi)constitutive hp4d promoter. These two expression cassettes of YlMNN4 were subcloned into one vector as a tandem construct carrying flanking regions (PT) of the ADE2 gene for targeted integration into the ADE2 locus of the genome and the ADE2 gene as a selection marker.

Intermediate Strain OXYY1569: The first transformation was a co-transformation of the expression cassette purified from pRAN058 and pRAN059 vectors using URA3 and LEU2 marker to produce intermediate recombinant strain OXYY1569. OXYY1569 carries two expression constructs of huGAA under control of the pPOX2 promoter randomly integrated in the genome of strain G014.

OXYY1569 was selected as follows. PCR screening of genomic DNA was performed in order to confirm the integration of the foreign huGAA DNA into the genome of *Y. lipolytica*. Primers were designed to amplify a fragment of 2552 bp from huGAA nucleotide sequence. Southern blot analysis of the genomic DNA also was performed in order to confirm the integration of at least 2 copies of huGAA DNA. In particular, genomic DNAs from OXYY1569 clones were digested with Hind III and probed with huGAA DIG labeled specific probe.

In order to select a clone secreting high levels of huGAA, several randomly selected clones that were identified as positive in the PCR screening and Southern blot were grown in shake flasks under POX2 inducing conditions according to a standard procedure. In all cases, the culture supernatant was collected 72 h post-induction and screened in a standard Western blot and enzyme activity assay analysis. N-Glycan analysis of OXYY1569 indicated the predominant structure in OXYY1569 is $Man_8GlcNAc_2$.

Intermediate Strain OXYY1584: Recombinant strain OXYY1569 was transformed in order to integrate two copies of the *Y. lipolytica* MNN4 gene into its genome to produce OXYY1584. The transformation was performed with a SacII/XmaI derived expression cassette excised from plasmid OXYP1479B. The expression cassette was designed for targeted integration into the ADE2 locus of *Y. lipolytica* genome. The recombinant strain was selected after Southern blotting and glycan analysis to evaluate the strain behavior with respect to the increased phosphorylation. Genomic DNA of several arbitrary chosen transformants was SpeI digested and probed with MNN4 specific DIG labeled probe. Correct targeted integration of MNN4 expression cassette into the ADE2 locus of *Y. lipolytica* genome should give 4207 bp and 5683 bp bands. Southern blot positive clones were grown in a standard shake flask procedure. N-glycan analysis of secreted proteins was performed in order to select the intermediate clone OXYY1584. Compared to the parent stain OXXY1569, the predominant structures after MNN4 over-expression are $Man_8GlcNAc_2$ $(PMan)_1$ and $Man_8GlcNAc_2$ $(PMan)_2$.

Production strain OXYY1589: To generate the final prototrophic production strain OXYY1589, a third copy of huGAA was integrated into the genome of recombinant OXYY1584 strain. The transformation was performed with the Not I excised expression cassette from pRAN069. Transformants were first screened by PCR on gDNA for presence of the additional copy of huGAA. To evaluate huGAA production arbitrary selected PCR positive clones were further analyzed for expression after a standard shake flask cultivation. The clone expressing the highest level of huGAA (OXYY1589) was chosen after Western blot analysis and enzymatic activity assay. It also was reconfirmed that the conversion levels of M8 to MP2-M8 and MP-M8 N-glycans was not influenced by the presence of the additional huGAA expression cassette.

Example 2

Fed Batch Cultivation of Strain OXYY1589

To produce huGAA from strain OXYY1589 (Example 1), a fed batch process was established using a 10 L stirred tank, with a working volume of 6-8 liters. The process was divided in two phases:

1) Batch growth on glucose for biomass formation

2) Product formation by induction with help of a limited oleic acid feed.

Typically the batch phase was about 20 hours (h) and the production phase approximately 72 hours. At the end of the process, the culture broth was centrifuged and the supernatant was collected. The supernatant was used as starting material for the purification of the GAA (see Example 3).

The following parameters were controlled during the fermentation. Aeration was maintained at a constant value of 1.5 vvm air (volume per volume per minute). Dissolved oxygen (DO) was initially kept at 30%. The stirring was increased from 600 to 1200 rpm depending on the DO levels. Once it reached the maximum of 1200 rpm, the speed was kept constant and the DO-setpoint was set to 10%. To maintain 10% DO, oxygen was spiked into the reactor with a maximal percentage of 50%. Foam evolution was controlled by a foam probe. In case of foam detection, antifoam was added to the bioreactor. The pH was controlled by adding 14% (v/v) ammonia (base) or 10% phosphoric acid to maintain a constant value of pH 6.8. The temperature was kept constant at 28° C. throughout the whole process.

Biomass was monitored by measurement of optical density at 600 nm (OD600). The samples were diluted 2-1000 times in distilled water to obtain values in the linear range of the spectrophotometer. Product formation was detected by Western blot analysis and specific enzymatic activity tests.

Example 3

Purification of Recombinant huGAA (rhGAA)

The supernatant after cultivation (see Example 2) was clarified via depth filtration. The resulting material was then concentrated 20 times via TFF and diafiltered against 20 mM sodium phosphate pH 6 and 100 mM NaCl on a 10 kDa MWCO membrane (Millipore).

Purification of rhGAA was started by adding ammonium sulphate up to a concentration of 1 M. After centrifugation, the supernatant was loaded on a Toyopearl-Phenyl 650M (Tosoh Biosciences) packed XK16/40 column. A linear gradient from 1 to 0 M ammonium sulphate was applied for elution. Those fractions that contain rhGAA were then pooled and subjected to buffer exchange into 10 mM BIS-TRIS pH 6. Further purification was achieved via anion exchange chromatography on a source 30Q packed Tricorn 10/50 or XK25/20 column (GE Healthcare) using a linear salt gradient from 0 to 1 M NaCl. The resulting GAA-containing fractions were then concentrated before loading onto a final Hiload 16/60 superdex 200 gel filtration column (GE Healthcare) that was pre-equilibrated with 50 mM sodium phosphate pH 6 and 200 mM NaCl. Fractions were selected on the basis of specific activity and purity on Coomassie-stained SDS-PAGE gels and then combined and concentrated to a final concentration of 5-10 mg/ml. Protein concentration was done on 15 ml Amicon Ultra centrifugal devices (Millipore) with a molecular weight cut-off of 10 kDa.

The reactions for the qualitative screening for rhGAA were started by adding the reaction buffer consisting of 0.35 mM 4-MUG, 0.1% BSA and 100 mM sodium acetate pH 4 in a 10:1 or 20:1 volume proportion to 10 or 5 µl of elution fraction. All reactions were done in 96-well flat-bottom microtiter plates. After an incubation period of 30 minutes to 1 hour at 37° C., an equal volume of 100 mM glycine pH11 was added to stop the reaction and the release of the fluorogenic reaction product 4-methylumbelliferone was observed under UV-light. Specific activities (units/mg protein) were determined using a colorimetric assay with the synthetic substrate p-nitrophenyl-α-D-glucopyranoside (PNPG) that measures the enzymatic release of the yellow coloured p-nitrophenolate reaction product. The reactions were started by mixing 10 µl of enzyme solution and 90 µl of substrate reaction buffer (2 mM PNPG in 150 mM citrate-phosphate buffer pH4, 1% BSA) in reaction wells of a microtiter plate and were subsequently incubated at 37° C. After 1 to 2 hours an equal volume of stop buffer, 10% sodium carbonate pH 12, was added to quench the reaction and convert the released p-nitrophenol (PNP) to its ionized state. Background-corrected absorbances and p-nitrophenolate standards were measured at a wavelength of 405 nm and specific activities were calculated. Protein concentrations were determined with the bicinchoninic acid (BCA) method. One unit was defined as the amount of enzyme that catalyzes the conversion of 1 nmol of PNPG to 1 nmol PNP and D-glucose per min at 37° C. at a final substrate concentration of 2 mM in a citrate-phosphate buffer, pH 4.0.

Example 4

Expression of CcMan5 and CcMan4

CcMan4 and CcMan5 ORFs were cloned into the vector pLSAH36, which contains a DsbA signal sequence and results in the expression of a protein with an N-terminal polyhistidine tag. Expression of the proteins was performed in *E. coli* BL21 cells. Proteins residing in the periplasm were isolated and purified using a Talon column. The nucleotide sequences of the ORF of DsbA-CcMan5 and DsbA-CcMan4 are provided in FIG. 3 and FIG. 4. A graphical representation of the plasmids pLSAHCcMan5 and pLSAHCcMan4 is given in FIG. 5.

Example 5

De-Mannosylation of APTS-Labeled Phosphorylated N-Glycans with GH47 α-Mannosidases The GH47 α-1,2-mannosidase from *Hypocrea jecorina* (Hj) (anamorph: *Trichoderma reesei*) can sequentially cleave all 4 α-1,2 linked mannose sugars from a Man9GlcNAc2 oligosaccharide (Maras, M. et al., J. Biotechnol, 77: 255-263 (2000)). A similar activity is described for the α-1,2-mannosidase from *Aspergillus satoi* (As) (also known as *Aspergillus phoenicis*)(Ichishima E. et al., Biochem. J., 339: 589-597).

HjMan (Genbank nr AAF34579) was expressed in *Pichia pastoris* and purified as described in Maras, M. et al., J. Biotechnol, 77: 255-263 (2000). A commercial enzyme preparation of AsMan (Genbank nr BAA08634) is available from Prozyme-Glyco.

Figure 6:
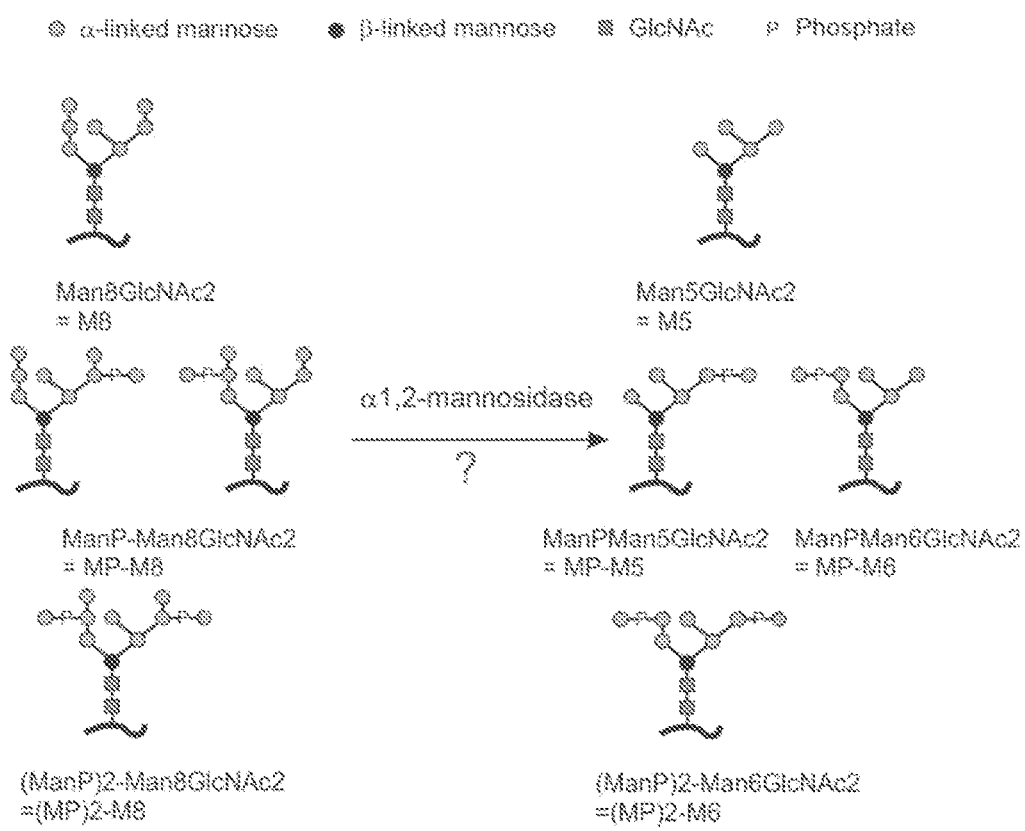
FIG. 6 is a schematic the potential final hydrolysis products, assuming that the α-1,2-mannosidases can also hydrolyze the terminal α-1,2-mannose if the underlying mannose is phosphorylated.
Figure 7:
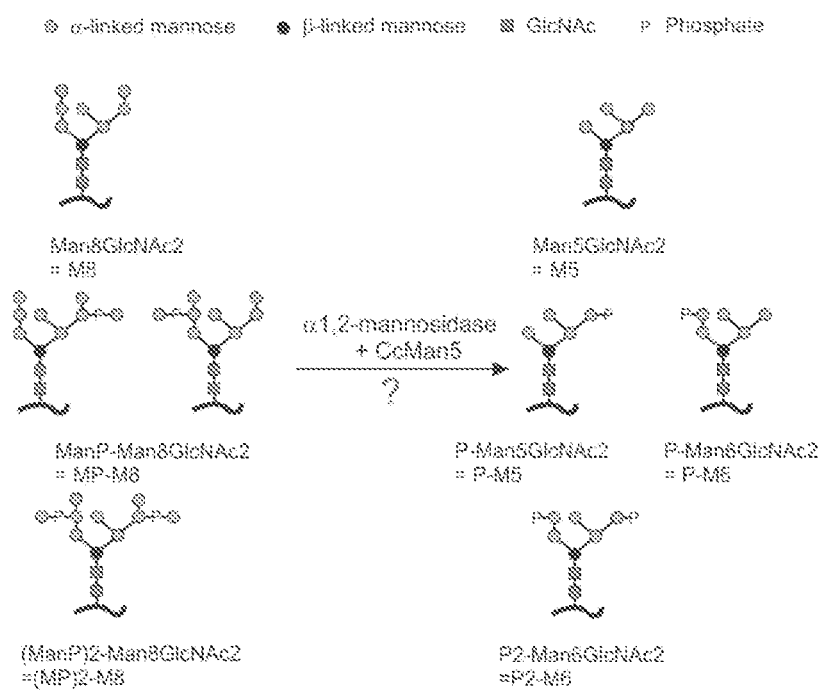
FIG. 7 is a schematic of the reaction products obtained using a phosphate uncapping enzyme.

The α-1,2-mannosidases from *H. jecorina* and *A. satoi* were tested on a mixture of 8-amino-1,3,6,-pyrenetrisulfonic acid (APTS)-labeled sugars derived from *Yarrowia lipolytica* cells overexpressing the MNN4 gene, containing $Man_8GlcNAc_2$ (M8), the monophosphorylated ManP-$Man_8GlcNAc_2$ (MP-M8) and/or the diphosphorylated $(ManP)_2$-$Man_8GlcNAc_2$ ((MP)2-M8) sugars. In FIG. 6, the potential final hydrolysis products are presented in a schematic presentation, assuming that the α-1,2-mannosidases can also hydrolyze the terminal α-1,2-mannose if the underlying mannose is phosphorylated. To be able to test the activity of the α-1,2-mannosidases on phosphorylated N-glycans with the phosphate residue uncapped (thus an oligosaccharide with a terminal phosphate present), the MNN4 sugars were treated with CcMan5, a GH92 enzyme from *Cellulosimicrobium cellulans* with phosphate uncapping activity (FIG. 7). CcMan5 removes the terminal mannose in a mannose-phospho-mannose diester linkage.

Unless otherwise stated all reactions with AsMan and HjMan on APTS-labeled N-glycans were performed overnight at 37° C. in an ammonium acetate buffer, 10 mM, pH 5.0 with 2 mM CaCl$_2$. The CcMan5 reaction was done at room temperature and pH 7.0, using a 10 mM HEPES buffer with 2 mM CaCl$_2$ added. To confirm the presence of phosphate uncapped glycans, or to be able to identify the structure of the fast-running glycans with a terminal phosphate, calf intestine phosphatase (CIP) was subsequently added to the reaction mixture. After phosphate hydrolysis neutral N-glycans are obtained which can be identified through the comparison with the electroferogram from the APTS-labeled N-glycans released from RNAseB (Man9-5GlcNAc2).

Figure 8:
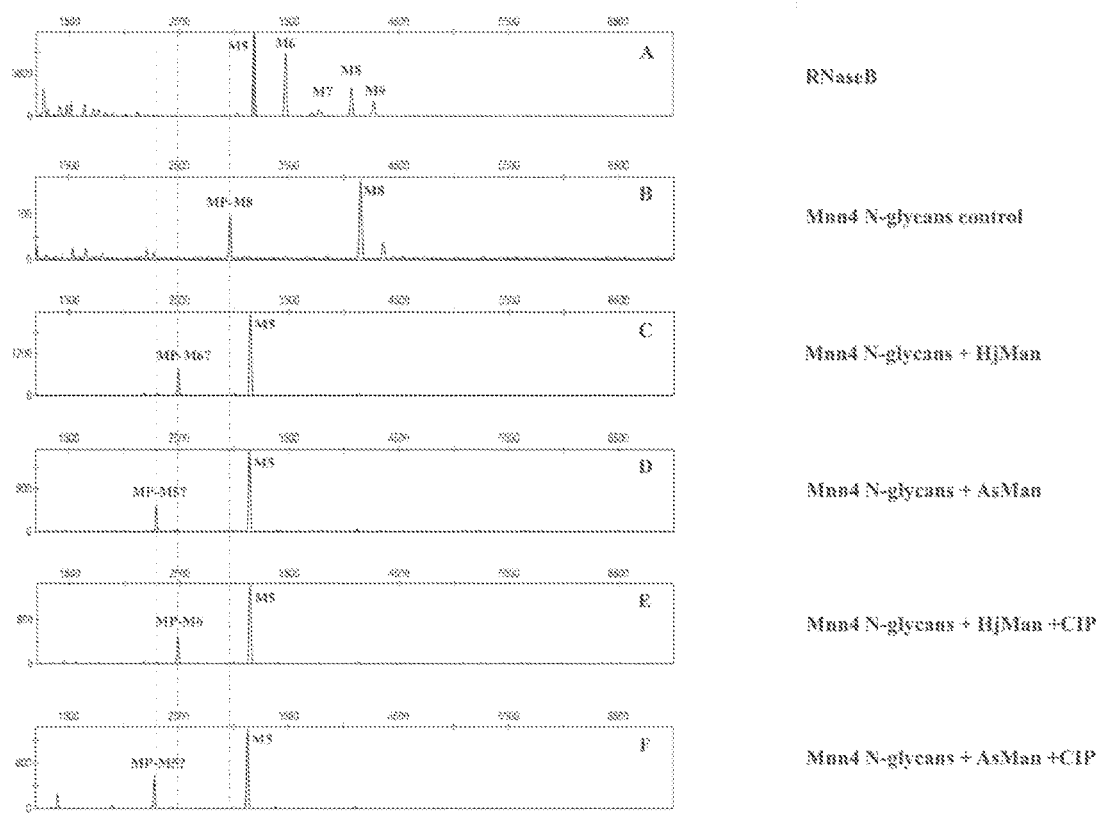
FIG. 8 contains the DSA-FACE electroferograms for the hydrolysis of a N-glycan preparation containing $Man_8GlcNAc_2$ and the monophosphorylated sugar ManP-$Man_8GlcNAc_2$ (Panel B) with HjMan and AsMan.

In FIG. 8, the DSA-FACE electroherograms are presented for the hydrolysis of a N-glycan preparation containing Man$_8$GlcNAc$_2$ and the monophosphorylated sugar ManP-Man$_8$GlcNAc$_2$ (Panel B) with HjMan and AsMan. Man$_8$GlcNAc$_2$ was hydrolyzed to Man$_5$GlcNAc$_2$ by both α-1,2-mannosidases, while a difference was observed for the hydrolysis of ManP-Man$_8$GlcNAc$_2$. HjMan most likely released two α-1,2-linked mannoses (ManP-Man$_6$GlcNAc$_2$ in panel C). The slightly faster running peak that appeared after AsMan treatment suggested the release of three α-1,2-linked mannoses and thus the formation of ManP-Man$_5$GlcNAc$_2$ (Panel D). The newly formed products did not disappear after treatment with calf intestine phosphatase (CIP), confirming that the phosphates are still mannose-capped (Panel E and F).

Figure 9A:
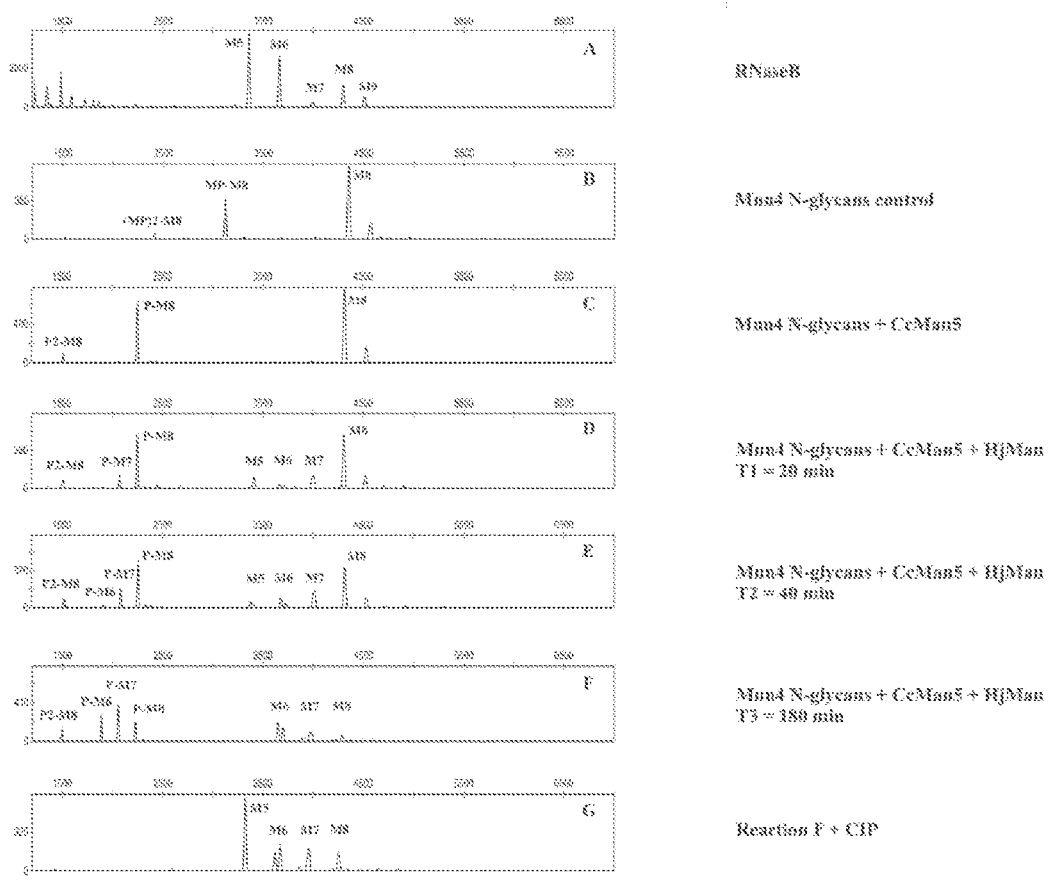
FIGS. 9A and 9B are DSA-FACE electroferograms for the hydrolysis of a N-glycan preparation containing $Man_8GlcNAc_2$ and the monophosphorylated sugar ManP-$Man_8GlcNAc_2$ (Panel B) with HjMan (9A) and AsMan (9B), where the MNN4 sugars were first treated with the phosphate uncapping enzyme CcMan5.
Figure 9B:
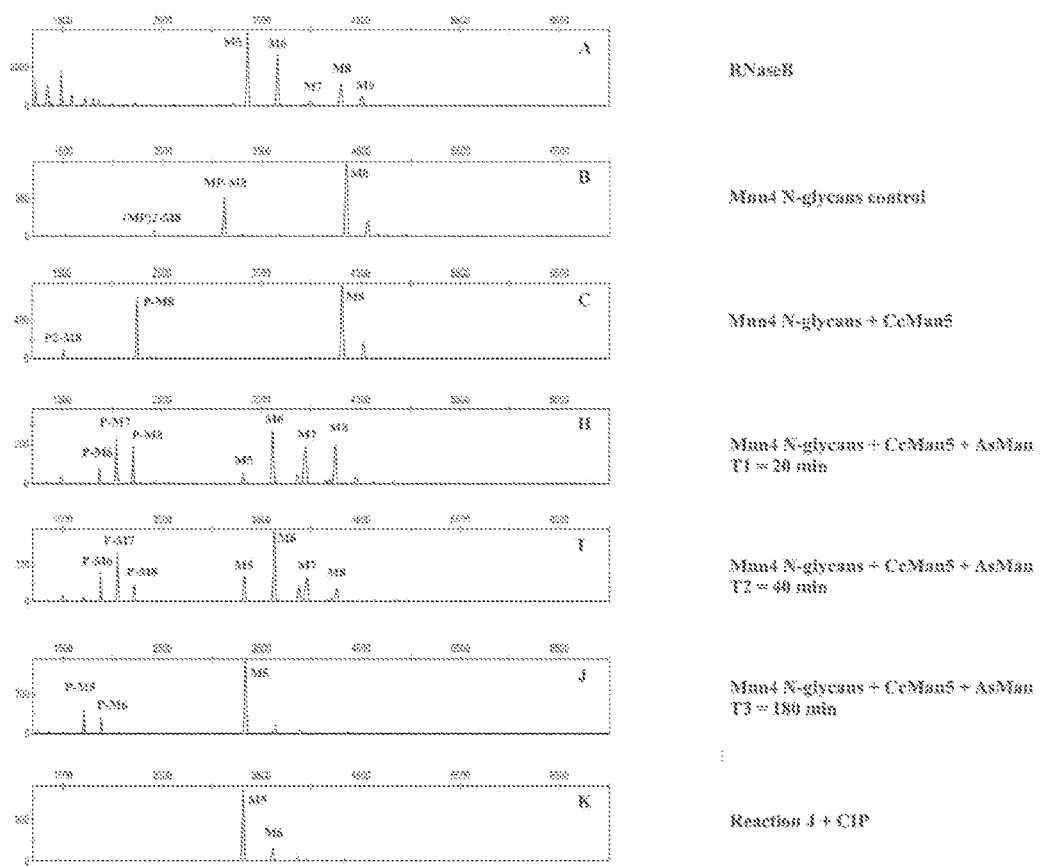

To confirm that the fast running peak in panel E is ManP-Man6GlcNAc2 and the one in panel D is ManP-Man$_5$GlcNAc$_2$ (FIG. 8), the experiment with HjMan and AsMan was repeated on MNN4 sugars which were first treated with the phosphate uncapping enzyme CcMan5 (yielding P-Man$_8$GlcNAc$_2$, panel C in FIG. 8). After incubation with the α-1,2-mannosidases for 20, 40 and 180 minutes at 37° C. the reaction was stopped by heating the reaction mixture at 100° C. for 3 minutes. Next a CIP treatment was performed. The results with HjMan are presented in FIG. 9A. HjMan sequentially cleaved P-Man$_8$GlcNAc$_2$ to P-Man$_7$GlcNAc$_2$ and P-Man$_6$GlcNAc$_2$ (Panel D to F). AsMan can sequentially removed three α-1,2-linked mannoses, resulting in the formation of P-Man$_7$GlcNAc$_2$, P-Man$_6$GlcNAc$_2$ and P-Man$_5$GlcNAc$_2$. See FIG. 9B.

The above results (FIGS. 9A and 9B), together with the overnight α-1,2-mannosidase digestion of MNN4 glycans (FIG. 8) could only be explained if only the α-1,6 arm (the right arm of the N-glycans (schematically presented in FIGS. 6A and 6B) is phosphorylated. Only the *A. satoi* α-1,2-mannosidase is capable of hydrolyzing the terminal α-1,2-mannose if the underlying mannose is phosphorylated (phosphate residue capped with a mannose residue or uncapped). HjMan only removes the two α-1,2-linked mannoses from the non-phosphorylated α-1,3 arm.

Figure 10:
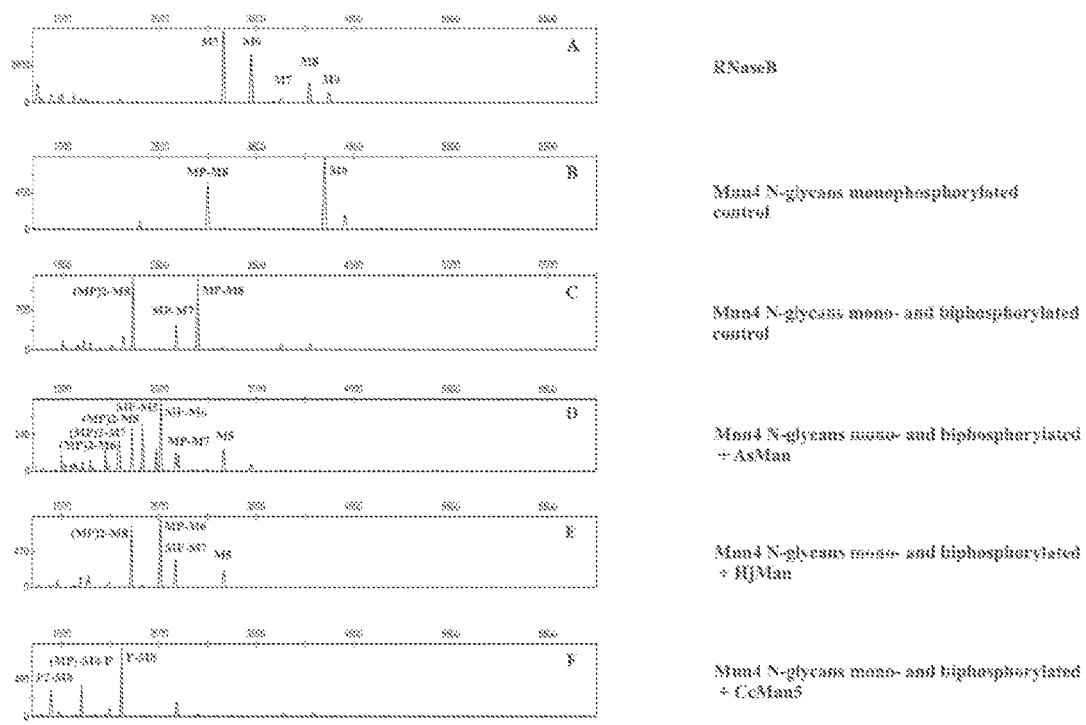
FIG. 10 contains DSA-FACE electroferograms for the hydrolysis of a MNN4 preparation using either AsMan or HjMan.

The fact that AsMan can remove a terminal α-1,2-mannose if the underlying mannose is phosphorylated and HjMan cannot, is also confirmed when a MNN4 preparation composed of monophosphorylated ManP-Man$_8$GlcNAc$_2$ and diphosphorylated (ManP)$_2$-Man$_8$GlcNAc$_2$ (FIG. 10, panel C) is used. AsMan can hydrolyze (ManP)$_2$-Man$_8$GlcNAc$_2$, as was observed from the appearance of two extra fast-running peaks in panel D (most likely (ManP)$_2$-Man$_7$GlcNAc$_2$ and (ManP)$_2$-Man$_6$GlcNAc$_2$). HjMan did not hydrolyze (ManP)$_2$-Man$_8$GlcNAc$_2$ (FIG. 10, panel E).

Example 6

De-Mannosylation with GH47 α-Mannosidases of Glycoproteins with a High Degree of Phosphorylated N-Glycans Expressed in a *Yarrowia lypolytica* Strain The human lysosomal α-glucosidase huGAA was expressed in *Y. lipolytica* strain OXYY1589 to yield a glycoprotein with a high degree of phosphorylated N-glycan structures. The huGAA was purified as described in Example 3.

Figure 11:
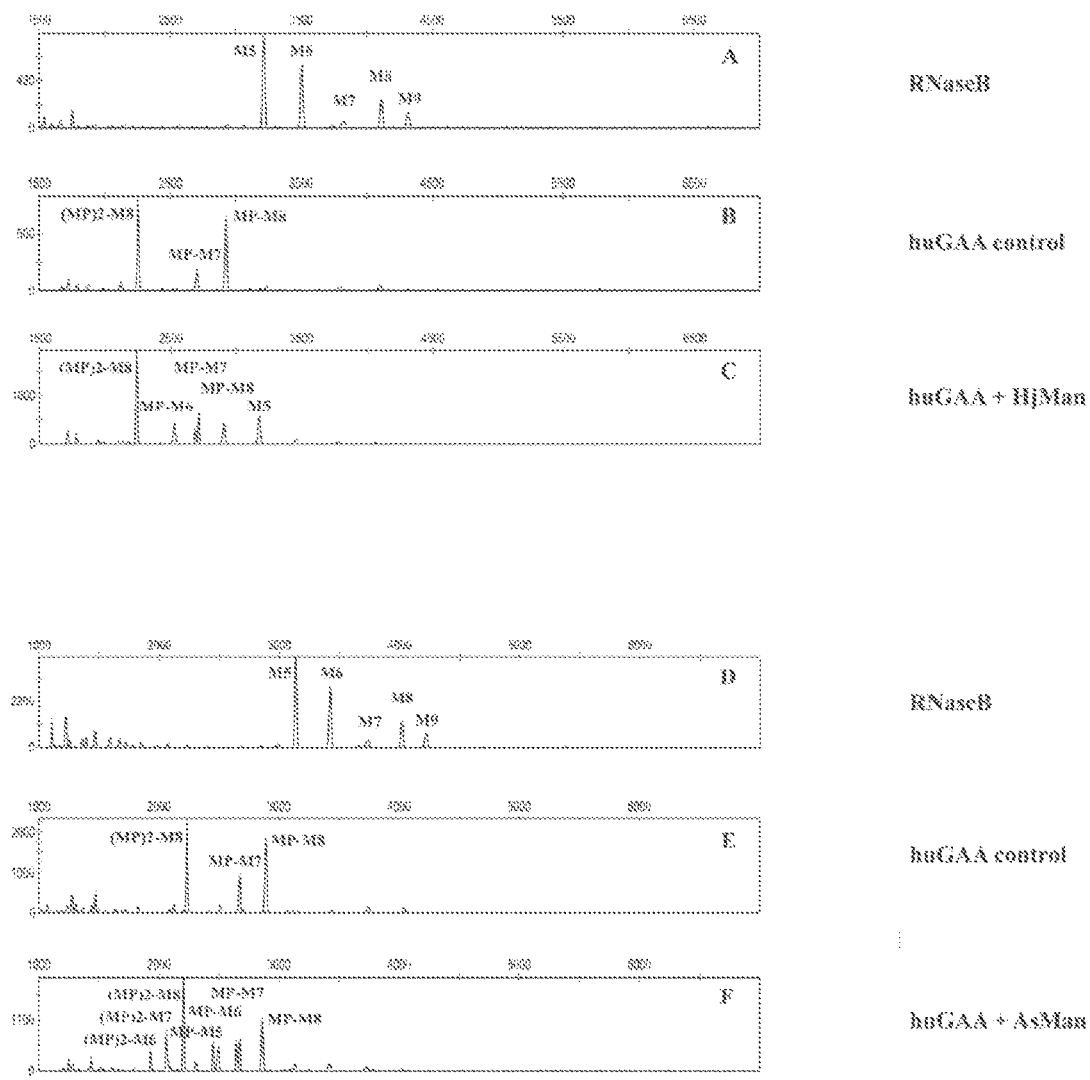
FIG. 11 contains the N-glycan profiles before and after the α-1,2-mannosidase treatment.

HjMan and AsMan were added to a solution of huGAA in 100 mM ammonium acetate, pH 5.0 with 2 mM CaCl2. The reaction mixture was incubated overnight at room temperature. The N-glycans were released with PNGaseF, labelled with APTS and subsequently analysed on DSA-FACE, essentially as described in Laroy W. et al., Nature Protocols, 1: 397-405 (2006). The N-glycan profiles before and after the α-1,2-mannosidase treatment are shown in FIG. 11. The N-glycan mixture released from purified huGAA was composed mainly of ManP-Man$_8$GlcNAc2 and (ManP)$_2$-Man$_8$GlcNAc$_2$ (FIG. 11, panels B and E). A peak running slightly faster than ManP-Man$_8$GlcNAc$_2$ could be assigned to ManP-Man$_7$GlcNAc$_2$. Only very minor amounts of Man$_8$GlcNAc$_2$ and Man$_7$GlcNAc$_2$ were present. After incubation of huGAA with HjMan the conversion of ManP-Man$_8$GlcNAc$_2$ to ManP-Man$_7$GlcNAc$_2$ and ManP-Man$_6$GlcNAc$_2$ was observed, while (ManP)$_2$-Man$_8$GlcNAc$_2$ was not hydrolyzed (FIG. 11, panel C). The electroferogram in panel D shows the sugars obtained after treatment of huGAA with AsMan. AsMan hydrolyzed (ManP)$_2$-Man$_8$GlcNAc$_2$ with the formation of (ManP)$_2$-Man$_7$GlcNAc$_2$ and (ManP)$_2$-Man$_6$GlcNAc$_2$ at the left side of the electroferogram and next to ManP-Man$_7$GlcNAc$_2$ and ManP-Man$_6$GlcNAc$_2$. ManP-Man$_5$GlcNAc$_2$ was also formed from the hydrolysis of ManP-Man$_8$GlcNAc$_2$. These data confirm that the α-1,6 arm is phosphorylated in the ManP-Man$_8$GlcNAc$_2$ structure and that also on the glycoprotein level AsMan can hydrolyze the terminal α-1,2-mannose if the underlying mannose is phosphorylated. The HjMan activity was limited to the release of α-1,2-linked mannoses from the neutral Man8GlcNAc2 N-glycans or to the removal of the two α-1,2-linked mannoses on the non-phosphorylated α-1,3 arm in ManP-Man$_8$GlcNAc$_2$.

Example 7

Figure 12A:
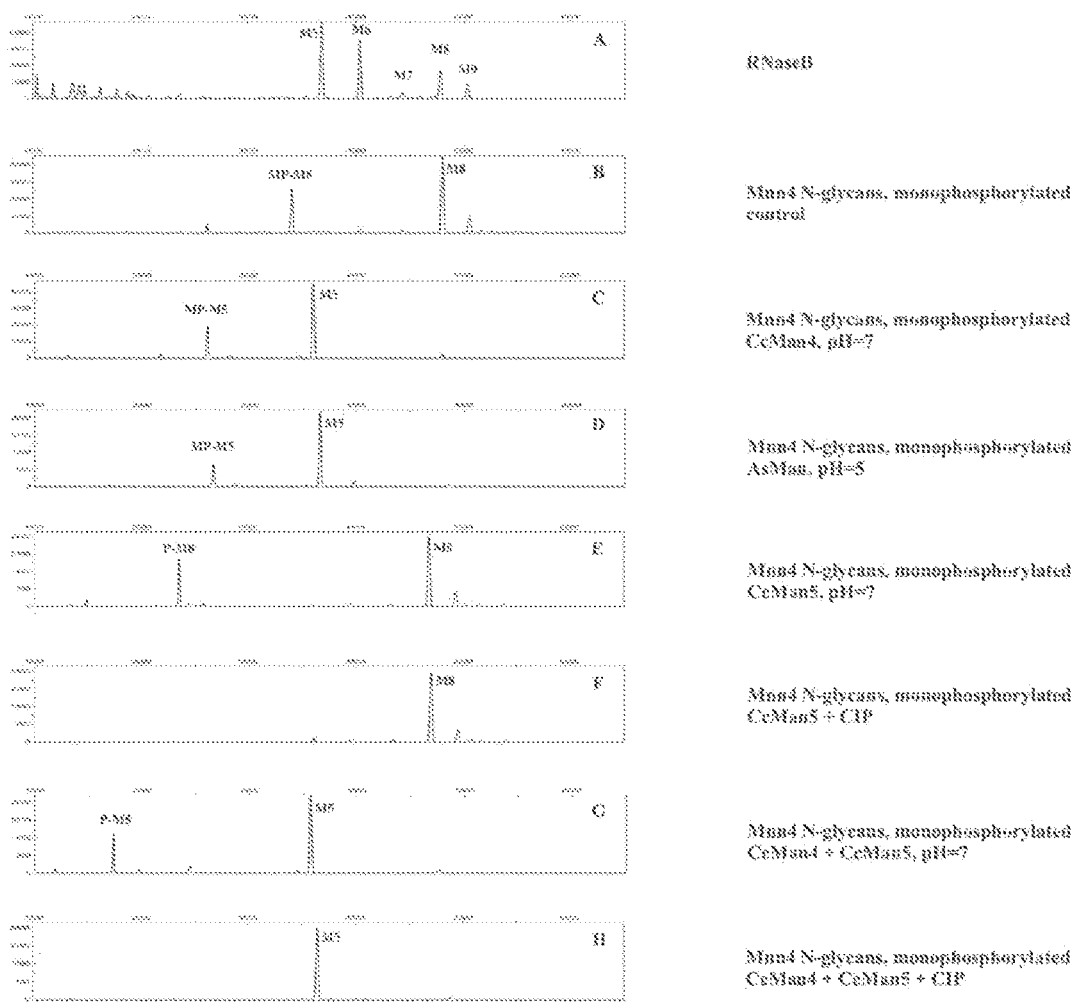
FIGS. 12A and 12B are DSA-FACE electroferograms of the activity of the periplasmic solution on (APTS)-labeled N-glycans derived from a MNN4 overexpressing strain.
Figure 12B:
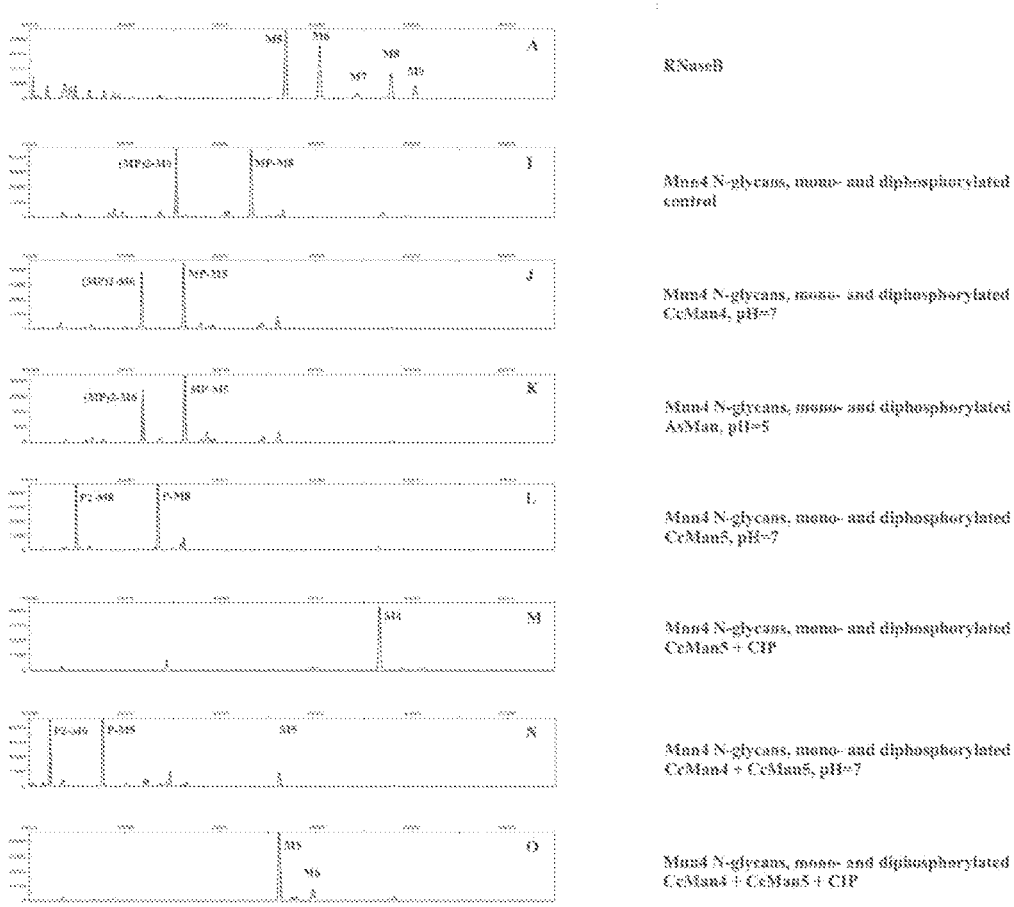

De-Mannosylation of APTS-Labeled Phosphorylated N-Glycans with GH92 α-Mannosidases CcMan4 and CcMan5 were expressed in *E. coli* and different cell fractions were isolated as described in Example 4. The activity of the periplasmic solution was tested on (APTS)-labeled N-glycans derived from a MNN4 overexpressing strain and analyzed on DSA-FACE (FIG. 12). The N-glycans were incubated overnight at room temperature with CcMan4, CcMan5 or with a mixture of both enzymes in a 10 mM HEPES buffer, pH 7.0 with 2 mM CaCl$_2$. A control experiment with AsMan was included, and was performed as described in example 5. In the experiment shown in FIG. 12A, a MNN4 fraction was used containing mainly $Man_8GlcNAc_2$ (M8) and monophosphorylated $ManP-Man_8GlcNAc_2$ (MP-M8) (Panel B). CcMan4 hydrolyzed $Man_8GlcNAc_2$ and $ManP-Man_8GlcNAc_2$ to $Man_5GlcNAc_2$ and $ManP-Man_5GlcNAc_2$, respectively (panel C). The same reaction products were obtained with AsMan (panel D and example 5). CcMan5 did not hydrolyze the glycosidic linkage between two α-1,2 mannoses (thus no shift of the $Man_8GlcNAc_2$ peak), but uncapped the phosphate in $ManP-Man_8GlcNAc_2$, yielding the fast-running peak $P-Man_8GlcNAc_2$ (Panel E). After incubation of this reaction mixture with CIP only a peak corresponding with $Man_8GlcNAc_2$ is observed (Panel F). A mixture of CcMan4 and CcMan5 hydrolyzed $Man_8GlcNAc_2$ and $ManP-Man_8GlcNAc_2$ to $Man_5GlcNAc_2$ and $P-Man_5GlcNAc_2$, respectively (Panel G). Therefore only a peak corresponding with $Man_5GlcNAc_2$ is observed after CIP treatment (Panel H). CcMan4 also hydrolyzed the diphosphorylated $(ManP)_2-Man_8GlcNAc_2$ to $(ManP)_2-Man_6GlcNAc_2$ (FIG. 12B, panel J), as was also observed with AsMan (panel K and example 5). A mixture of CcMan4 and CcMan5 produced $P2-Man_6GlcNAc_2$ and $P-Man_5GlcNAc_2$ (Panel N).

CcMan4 is thus an α-1,2-mannosidase capable of also hydrolyzing the terminal α-1,2-mannose if the underlying mannose is phosphorylated. It can be used in combination with the phosphate uncapping enzyme CcMan5.

Example 8

Figure 13:
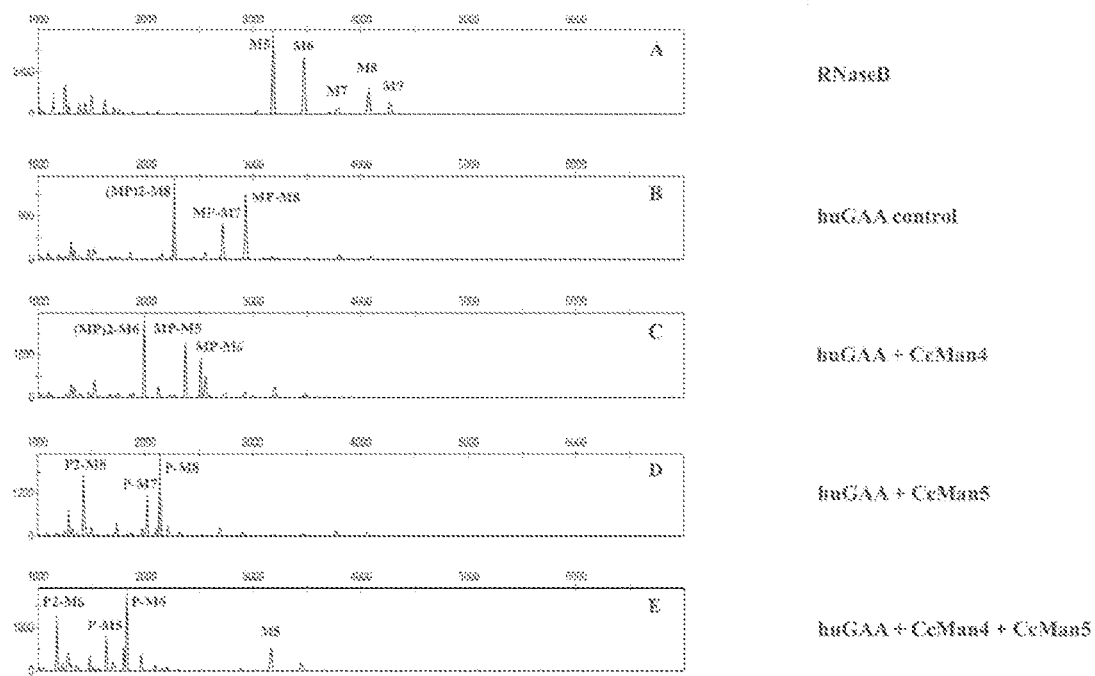
FIG. 13 is the DSA-FACE electroferogram analysis of the activity of CcMan4 and CcMan5 after incubating with huGAA expressed in *Y. lipolytica*.

De-Mannosylation with GH92 α-Mannosidases of Glycoproteins with a High Degree of Phosphorylated N-Glycans Expressed in a *Yarrowia lypolytica* strain CcMan4 and CcMan5 were incubated with huGAA expressed in *Y. lipolytica*. The analysis was performed as described in Example 6. A 100 mM HEPES buffer, pH 7.0 with 2 mM $CaCl_2$ was used for both CcMan4 and CcMan5 in an overnight assay at room temperature. The DSA-FACE analysis is presented in FIG. 13. The N-glycan mixture released from purified huGAA was mainly composed of $ManP-Man_8GlcNAc_2$ and $(ManP)_2-Man_8GlcNAc_2$ (Panel B). A peak running slightly faster than $ManP-Man_8GlcNAc_2$ could be assigned to $ManP-Man_7GlcNAc_2$.

CcMan4 de-mannosylated the huGAA glycoprotein. In the electroferogram (Panel C) peaks corresponding with $(ManP)_2-Man_6GlcNAc_2$, $ManP-Man_5GlcNAc_2$ and $ManP-Man_6GlcNAc_2$ were observed. In combination with CcMan5 the phosphate uncapped products $P2-Man_6GlcNAc_2$, $P-Man_5GlcNAc_2$ and $P-Man_6GlcNAc_2$ were formed as shown in panel E.

Example 9

Figure 14:
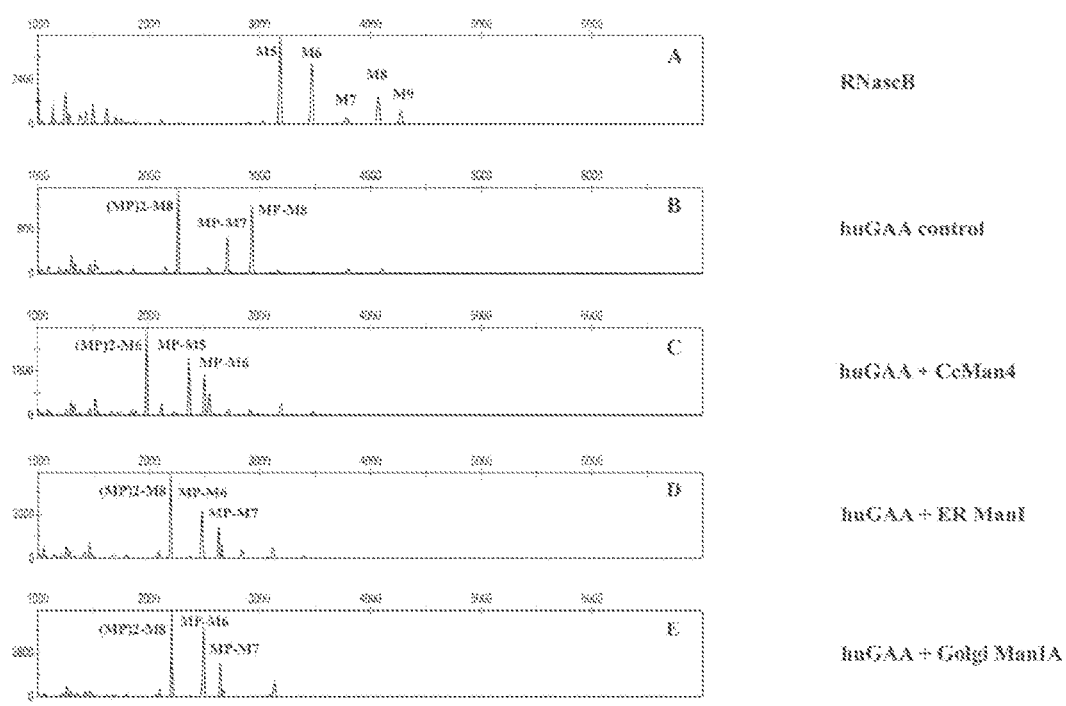
FIG. 14 is the DSA-FACE electroferogram analysis of the activity of recombinantly expressed ERManI or GolgiManIA after incubating with huGAA expressed in *Y. lipolytica*.

Additional Examples of De-Mannosylation with GH47 α-Mannosidases of Glycoproteins with a High Degree of Phosphorylated N-Glycans Expressed in a *Yarrowia lypolytica* Strain ERManI and GolgiManIA are two class I α-1,2-mannosidases belonging to family GH47. Recombinantly expressed ERManI and GolgiManIA were incubated overnight at room temperature with huGAA expressed in *Y. lipolytica*. The analysis was performed as described in Example 6 and FIG. 10. A 100 mM HEPES buffer, pH 7.0 with 2 mM $CaCl_2$ was used for ERManI, while the incubation with GolgiManIA is performed in a 100 mM MES buffer, pH 6.0 with 2 mM $CaCl_2$. The DSA-FACE analysis is presented in FIG. 14.

Both ERManI and GolgiManIA could de-mannosylate the huGAA glycoprotein, but their activity was limited to the hydrolysis of $ManP-Man_8GlcNAc_2$ to $ManP-Man_6GlcNAc_2$ (Panels D and E respectively). This result was also obtained with the GH 47 α-1,2-mannosidase from *H. Jecorina* (HjMan, FIG. 11, panel C), while the GH47 α-1,2-mannosidase from *A. satoi* (AsMan, FIG. 11, panel F) and the GH92 CcMan4 (FIG. 12, panel C) trimmed $(ManP)_2-Man_8GlcNAc_2$ and $ManP-Man_8GlcNAc_2$ to $(ManP)_2-Man_6GlcNAc_2$ and $ManP-Man_5GlcNAc_2$, respectively.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for demannosylating phosphorylated N-glycans on a glycoprotein, said method comprising contacting in vitro a recombinant glycoprotein comprising a terminal alpha-1,2 mannose linkage in which the underlying mannose is phosphorylated with a mannosidase that hydrolyzes a terminal alpha-1,2 mannose linkage when the underlying mannose is phosphorylated, wherein the contacting results in hydrolysis of the terminal alpha-1,2 mannose linkage, to produce a demannosylated glycoprotein, wherein the mannosidase is:
   (a) a wild-type glycoside hydrolase (GH)92 family polypeptide or a wild-type GH47 family polypeptide;
   (b) a deletion variant that is the polypeptide of (a) but lacks up to twenty amino acid segments, each segment consisting of two amino acids;
   (c) a deletion variant that is the polypeptide of (a) or the variant of (b) but lacks up to twenty single, non-contiguous amino acids of the polypeptide of (a) or the variant of (b); or
   (d) a substitution variant that is the polypeptide of (a), the variant of (b), or the variant of (c), but with no more than 10 conservative substitutions.

2. The method of claim 1, wherein said mannosidase is from *Aspergillus satoi*.

3. The method of claim 1, wherein said mannosidase is from *Cellulosimicrobium cellulans*.

4. The method of claim 1, wherein the mannosidase comprises SEQ ID NO:5.

5. The method of claim 1, wherein the mannosidase is of the GH47 family.

6. The method of claim 1, wherein the mannosidase comprises the amino acid sequence encoded by SEQ ID NO:4.

7. The method of claim 1, wherein the mannosidase is of the GH92 family.

8. The method of claim 1, wherein the method further comprises isolating the demannosylated glycoprotein.

9. The method of claim 1, wherein the glycoprotein is a human protein.

10. The method of claim 1, wherein the glycoprotein is a pathogen protein, a lysosomal protein, a growth factor, a cytokine, a chemokine, an antibody or antigen-binding fragment thereof, or a fusion protein.

11. The method of claim 10, wherein the lysosomal protein is a lysosomal enzyme.

12. The method of claim 10, wherein the lysosomal enzyme is associated with a lysosomal storage disorder (LSD).

13. The method of claim 12, wherein the LSD is Fabry's disease, mucopolysaccharidosis I, Farber disease, Gaucher disease, GM1-gangliosidosis, Tay-Sachs disease, Sandhoff disease, GM2 activator disease, Krabbe disease, metachromatic leukodystrophy, Niemann-Pick disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis, cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

* * * * *